US007267666B1

(12) United States Patent
Duchon et al.

(10) Patent No.: US 7,267,666 B1
(45) Date of Patent: *Sep. 11, 2007

(54) ANGIOGRAPHIC INJECTOR SYSTEM WITH MULTIPLE PROCESSOR REDUNDANCY

(75) Inventors: Douglas J. Duchon, Chanhassen, MN (US); James P. Smith, Watertown, MN (US); Katherine H. Anderson, Golden Valley, MN (US); Robert F. Wilson, Roseville, MN (US); Jiyan Liu, Maplewood, MN (US)

(73) Assignee: Acist Medical Systems, Inc., Eden Prairie, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 08/966,088

(22) Filed: Nov. 7, 1997

Related U.S. Application Data

(63) Continuation-in-part of application No. 08/957,801, filed on Oct. 24, 1997, and a continuation of application No. 08/946,293, filed on Oct. 7, 1997, now Pat. No. 5,800,397, and a continuation of application No. 08/426,148, filed on Apr. 20, 1995, now abandoned.

(51) Int. Cl.
*A61M 1/00* (2006.01)
(52) U.S. Cl. .................................. 604/151; 128/DIG. 1
(58) Field of Classification Search ................ 604/151, 604/154, 155, 156, 65, 67; 128/DIG. 1; 404/268, 262
See application file for complete search history.

(56) References Cited

U.S. PATENT DOCUMENTS

| | | | | |
|---|---|---|---|---|
| 3,623,474 A | * | 11/1971 | Heilman | ...................... 604/155 |
| 3,701,345 A | * | 10/1972 | Heilman et al. | ............ 604/155 |
| 3,731,679 A | | 5/1973 | Wilhelmson et al. | |
| 3,739,943 A | | 6/1973 | Wilhelmson et al. | |
| 4,006,736 A | * | 2/1977 | Kranys et al. | ......... 128/DIG. 1 |

(Continued)

FOREIGN PATENT DOCUMENTS

EP     0 384 155 A2    1/1990

(Continued)

OTHER PUBLICATIONS

European Search Report for EP 05076973.6 dated Nov. 3, 2005.

*Primary Examiner*—Jerome Donnelly
*Assistant Examiner*—Fenn C. Mathew
(74) *Attorney, Agent, or Firm*—Kramer Levin Naftalis & Frankel LLP

(57) ABSTRACT

An angiographic injector system and a method of controllably delivering medical fluid to a patient from an angiographic injector system are disclosed. A multiple processor control system is used to actively control the injection process and to monitor sensed functions of the system. The multiple processors provide dual redundancy safety circuits for critical control functions such as syringe motor drive speed and current. A motor/servo-amplifier nested control function is also disclosed. A unique method and apparatus are disclosed for establishing injection parameter default values just prior to an injection procedure that are based on physiological values of the patient to be treated. The injector system uses an interactive display panel that presents sequenced set-up screens to the user and which enables the user to select injection procedures, parameters and other modes of operation directly through the interactive panel.

20 Claims, 42 Drawing Sheets

U.S. PATENT DOCUMENTS

| | | | |
|---|---|---|---|
| 4,512,764 A | 4/1985 | Wunsch | |
| 4,559,037 A * | 12/1985 | Franetzki et al. | 604/151 |
| 4,624,661 A | 11/1986 | Arimond | |
| 4,650,465 A * | 3/1987 | Langer et al. | 604/65 |
| 4,812,724 A * | 3/1989 | Langer et al. | 318/599 |
| 4,854,324 A * | 8/1989 | Hirschman et al. | 128/DIG. 1 |
| 4,908,017 A | 3/1990 | Howson et al. | |
| 4,966,579 A | 10/1990 | Polaschegg | |
| 5,104,374 A | 4/1992 | Bishko et al. | |
| 5,254,101 A | 10/1993 | Trombley, III | |
| 5,336,167 A * | 8/1994 | Sullivan et al. | 604/65 |
| 5,342,298 A * | 8/1994 | Michaels et al. | 128/DIG. 1 |
| 5,372,112 A * | 12/1994 | Ohtaka et al. | 123/17 |
| 5,472,403 A * | 12/1995 | Cornacchia et al. | 600/4 |
| 5,569,181 A | 10/1996 | Heilman et al. | |
| 5,687,717 A * | 11/1997 | Halpern et al. | 600/300 |
| 5,720,024 A * | 2/1998 | Saito et al. | 395/180 |
| 5,739,508 A | 4/1998 | Uber, III | |
| 5,795,333 A | 8/1998 | Reilly et al. | |
| 5,800,387 A * | 9/1998 | Duffy et al. | 604/65 |
| 5,806,519 A | 9/1998 | Evans, III et al. | |
| 5,808,203 A | 9/1998 | Nolan, Jr. et al. | |
| 5,840,026 A | 11/1998 | Uber, III et al. | |
| 5,843,037 A | 12/1998 | Uber, III | |
| 5,868,710 A * | 2/1999 | Battiato et al. | 604/123 |
| 5,873,861 A | 2/1999 | Hitchins et al. | |
| 5,885,216 A | 3/1999 | Evans, III et al. | |
| 5,920,054 A | 7/1999 | Uber, III | |
| 5,928,197 A * | 7/1999 | Niehoff | 604/155 |
| 5,947,935 A | 9/1999 | Rhinehart et al. | |
| RE36,648 E | 4/2000 | Uber, III et al. | |
| 6,096,011 A | 8/2000 | Trombley, III et al. | |
| 6,149,627 A | 11/2000 | Uber, III | |
| 6,197,000 B1 | 3/2001 | Reilly et al. | |
| 6,306,117 B1 | 10/2001 | Uber, III | |
| 6,317,623 B1 | 11/2001 | Griffiths et al. | |
| 6,339,718 B1 | 1/2002 | Zatezalo et al. | |
| RE37,602 E | 3/2002 | Uber, III et al. | |
| 6,385,483 B1 | 5/2002 | Uber, III et al. | |
| 6,397,098 B1 | 5/2002 | Uber, III et al. | |
| 6,402,717 B1 | 6/2002 | Reilly et al. | |
| 6,440,107 B1 | 8/2002 | Trombley, III et al. | |
| 6,442,418 B1 | 8/2002 | Evans, III et al. | |
| 6,471,674 B1 | 10/2002 | Emig et al. | |
| 6,475,192 B1 | 11/2002 | Reilly et al. | |
| 6,520,930 B2 | 2/2003 | Critchlow et al. | |
| 6,643,537 B1 | 11/2003 | Zatezalo et al. | |
| 6,652,489 B2 | 11/2003 | Trocki et al. | |
| 6,673,033 B1 | 1/2004 | Sciulli et al. | |
| 6,699,219 B2 | 3/2004 | Emig et al. | |
| 6,731,971 B2 | 5/2004 | Evans, III et al. | |
| 6,733,477 B2 | 5/2004 | Cowan et al. | |
| 6,733,478 B2 | 5/2004 | Reilly et al. | |
| 6,743,202 B2 | 6/2004 | Hirschman et al. | |
| 6,889,074 B2 | 5/2005 | Uber, III et al. | |
| 6,901,283 B2 | 5/2005 | Evans, III et al. | |
| 6,939,302 B2 | 9/2005 | Griffiths et al. | |

FOREIGN PATENT DOCUMENTS

| | | |
|---|---|---|
| EP | 0384155 | 8/1990 |
| EP | 384155 B1 * | 7/1994 |
| WO | WO96/20745 | 7/1996 |
| WO | WO96/20745 A | 7/1996 |
| WO | WO96/32887 | 10/1996 |

* cited by examiner

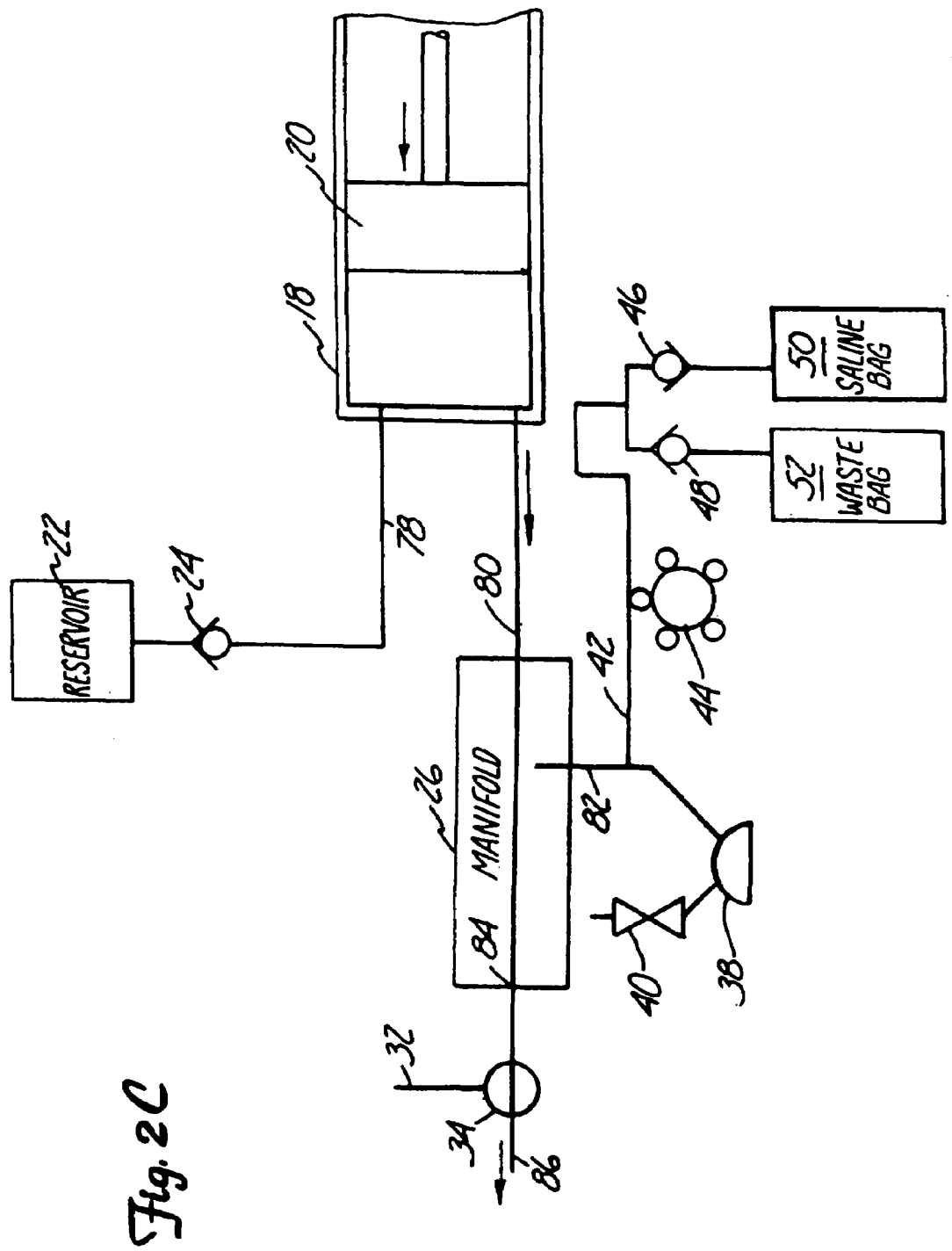

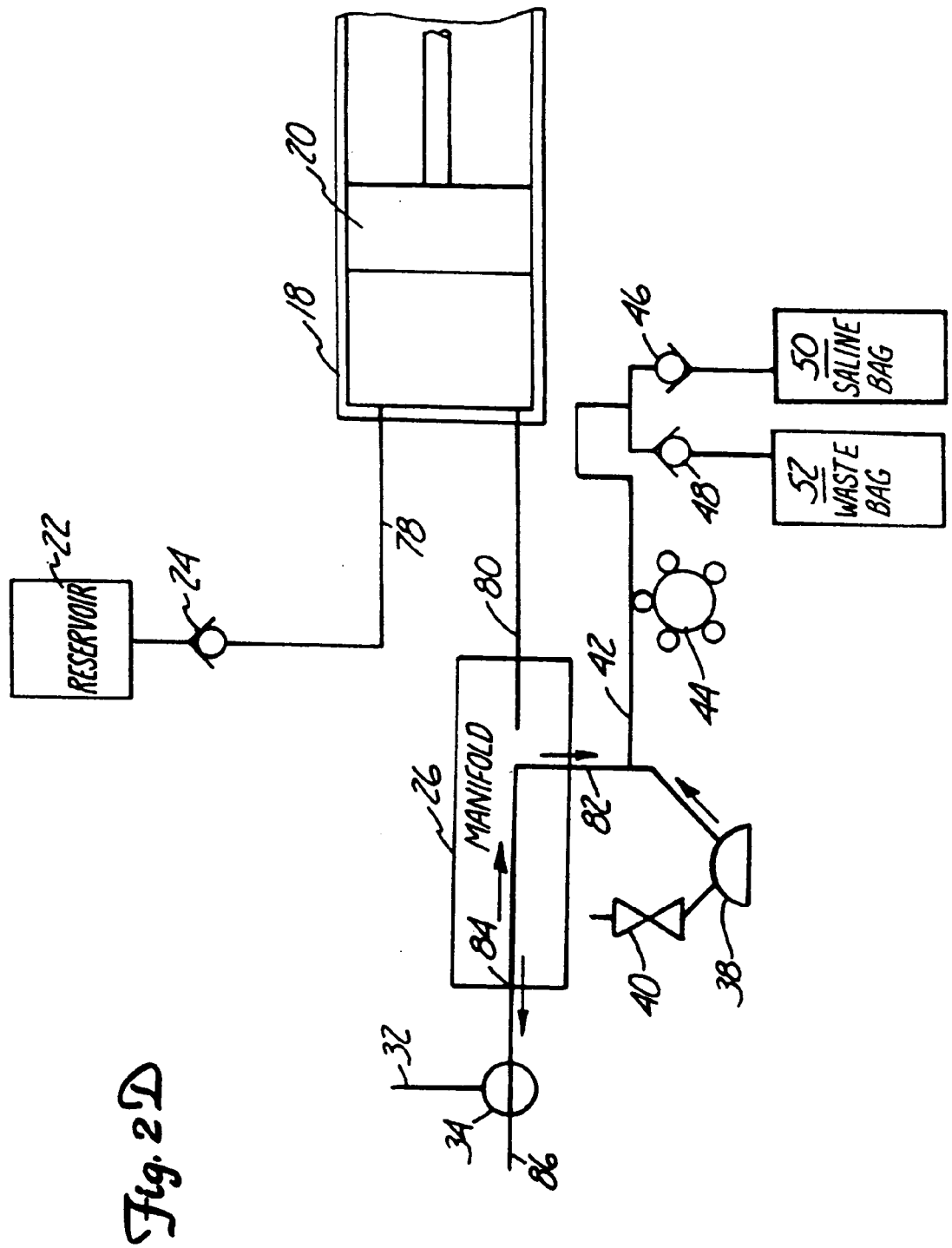

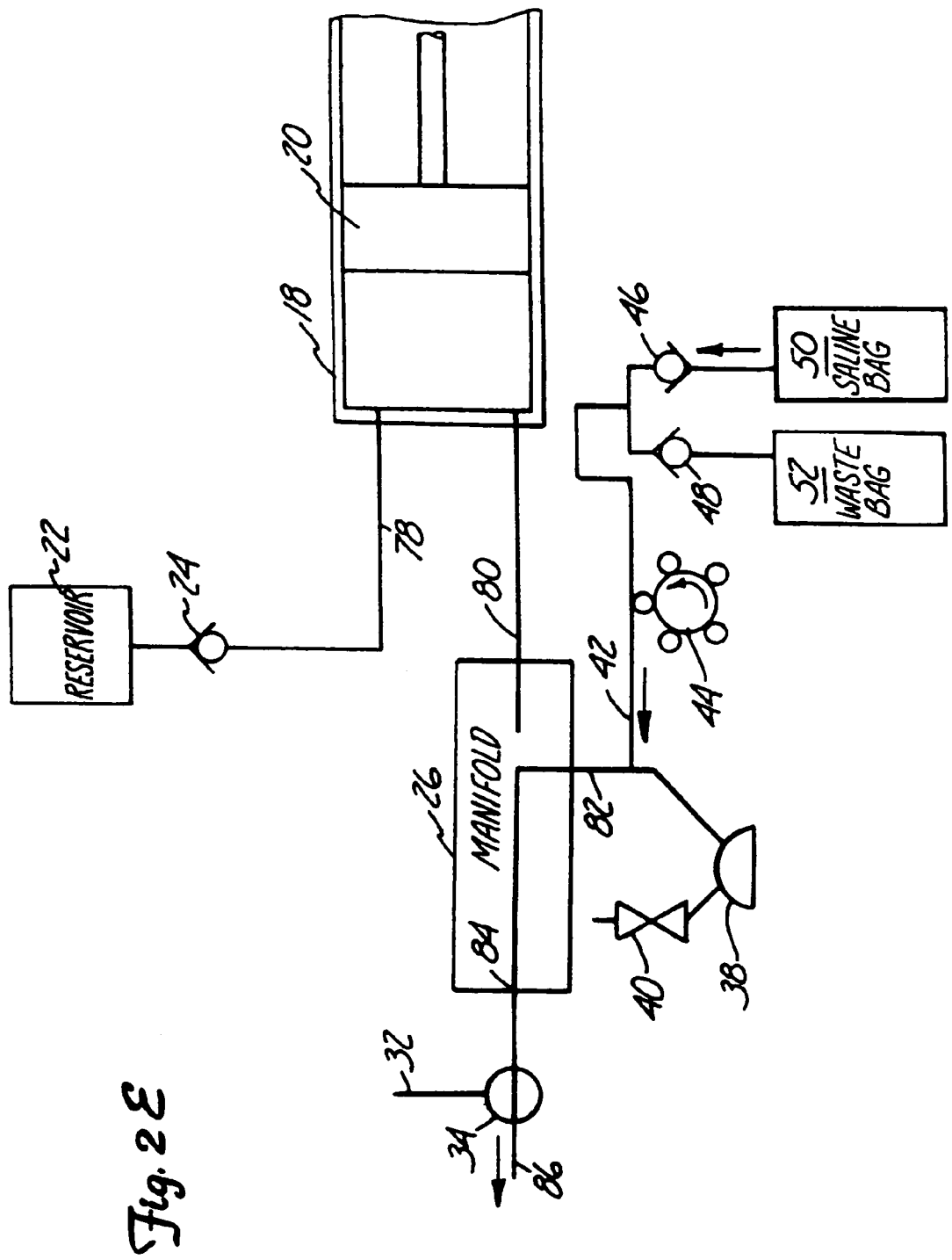

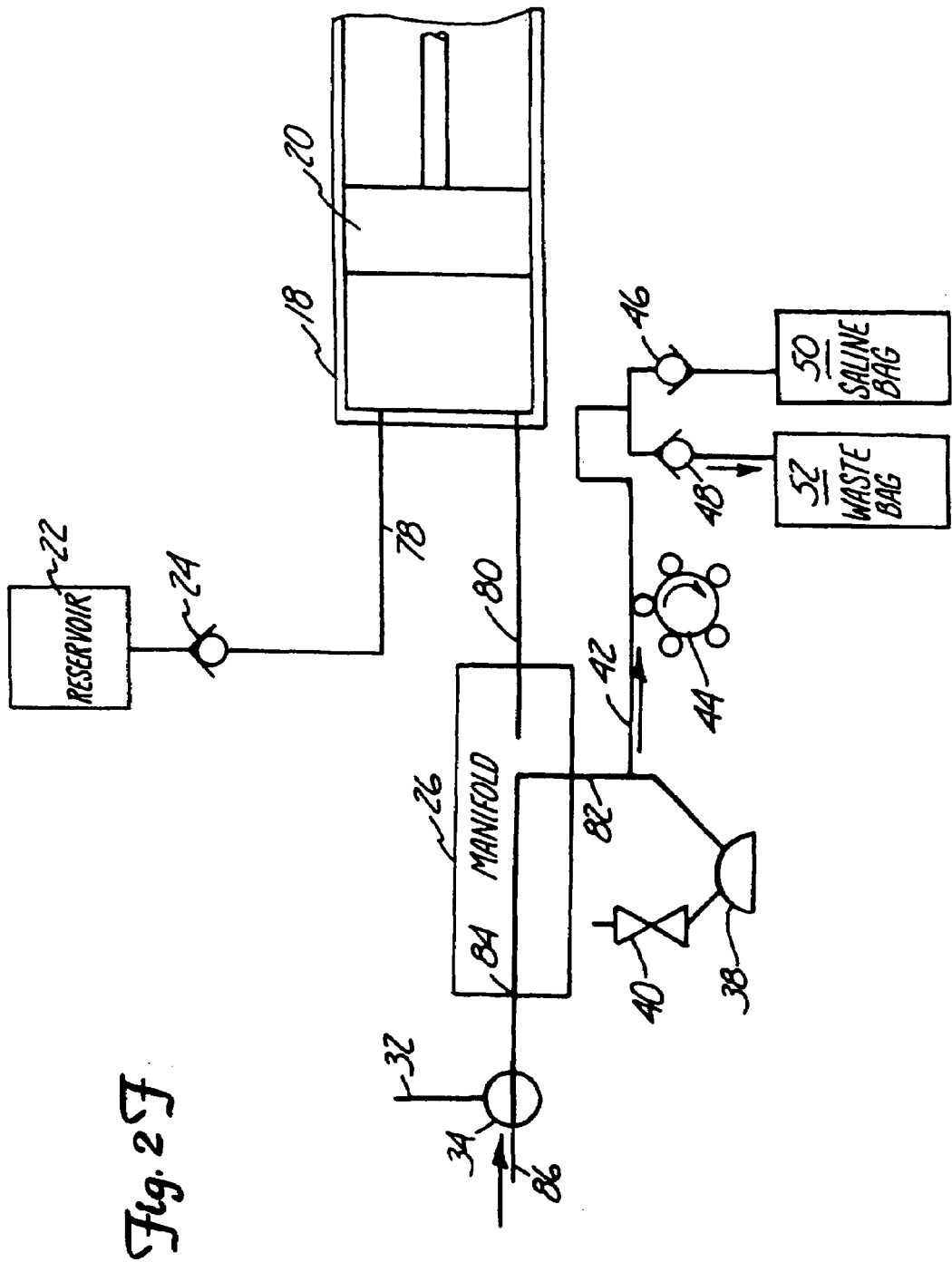

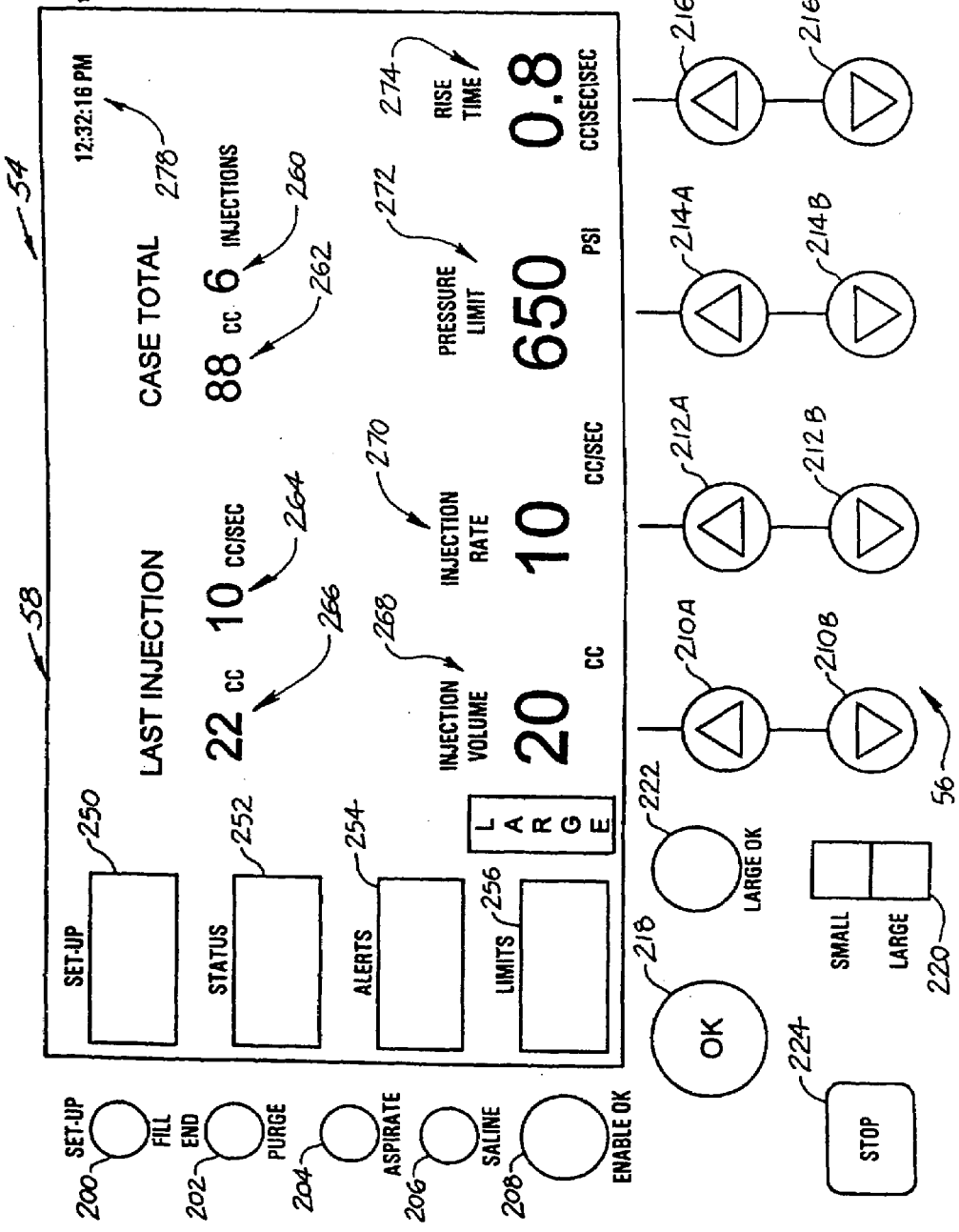

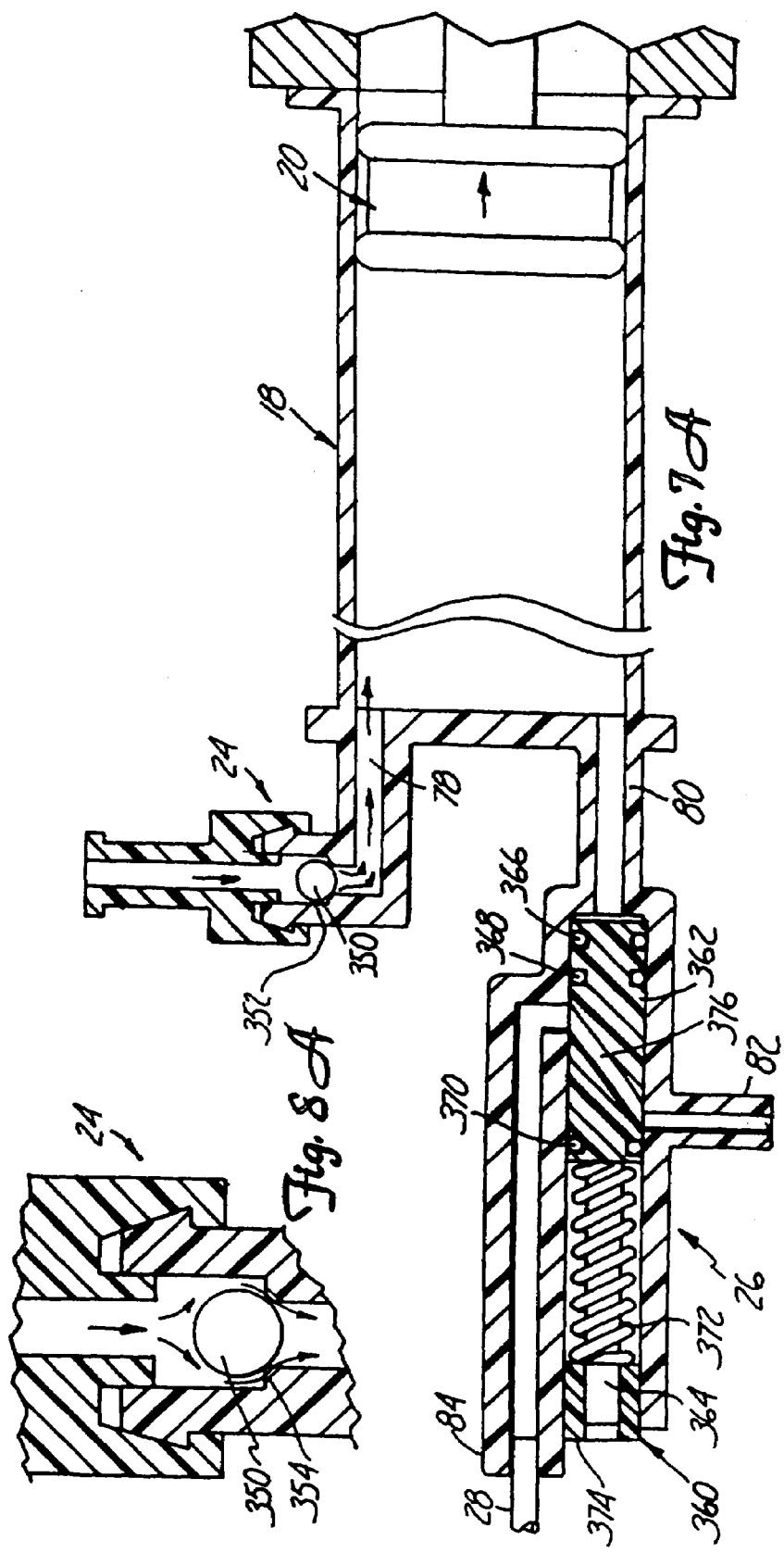

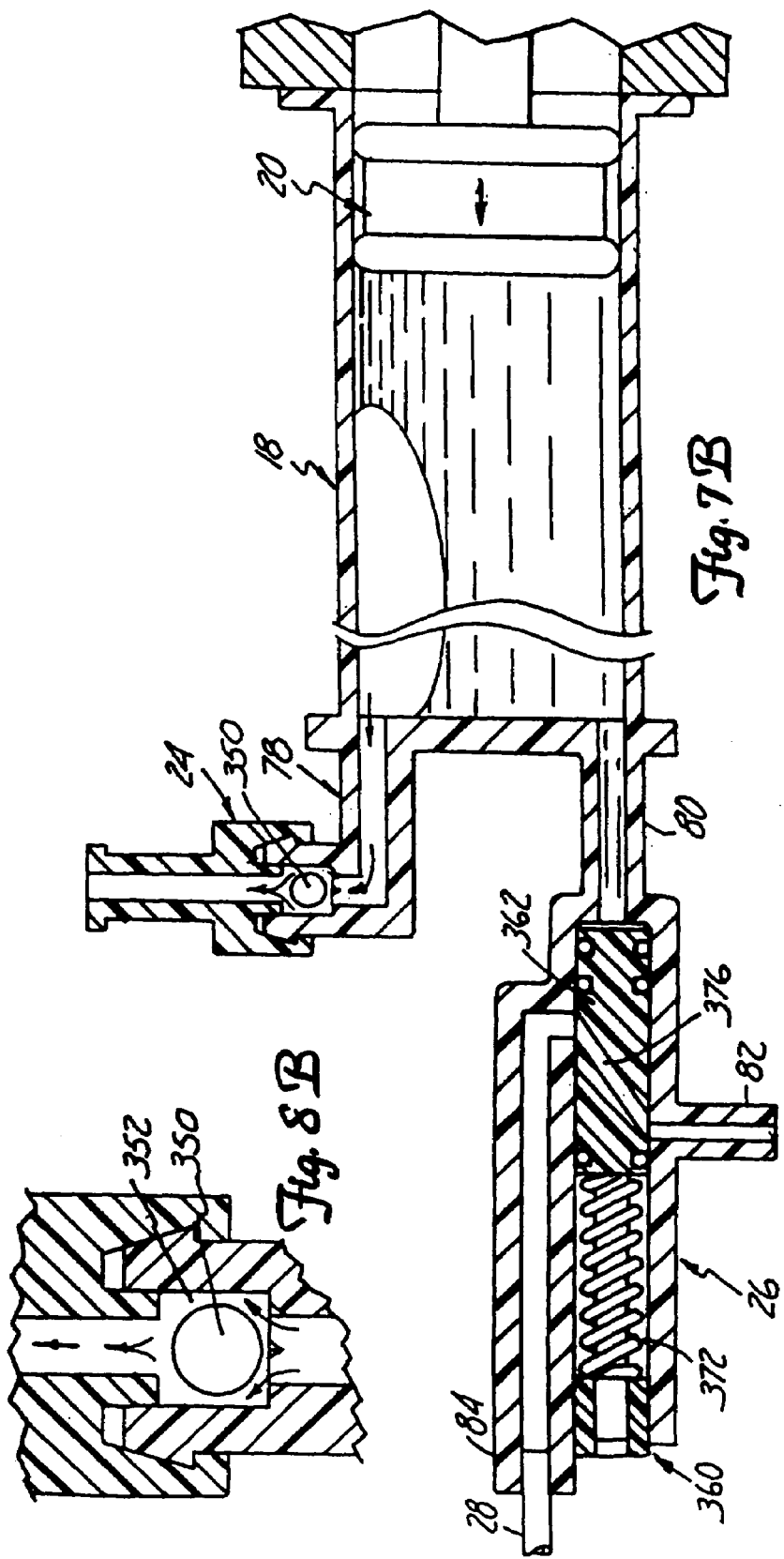

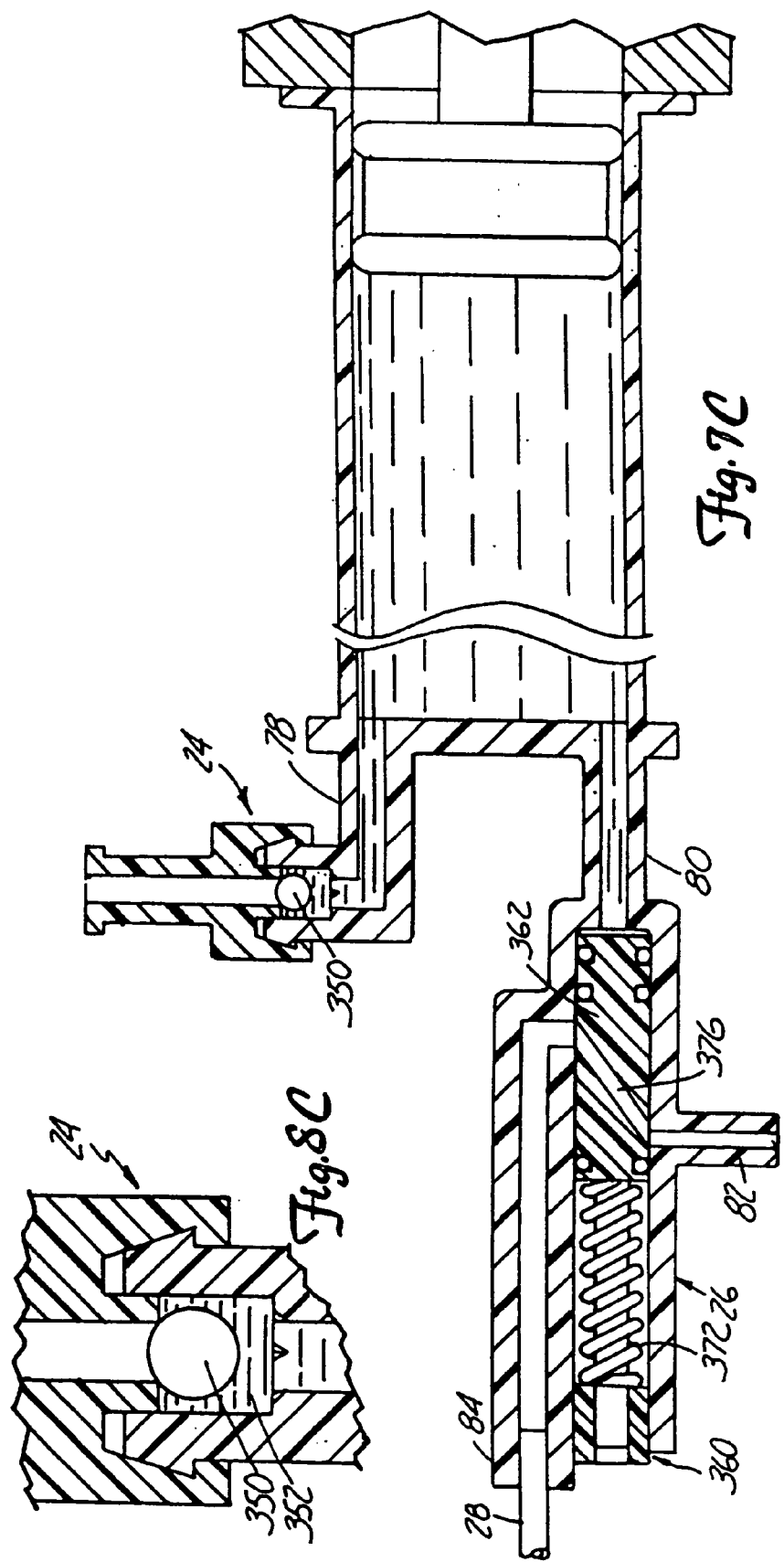

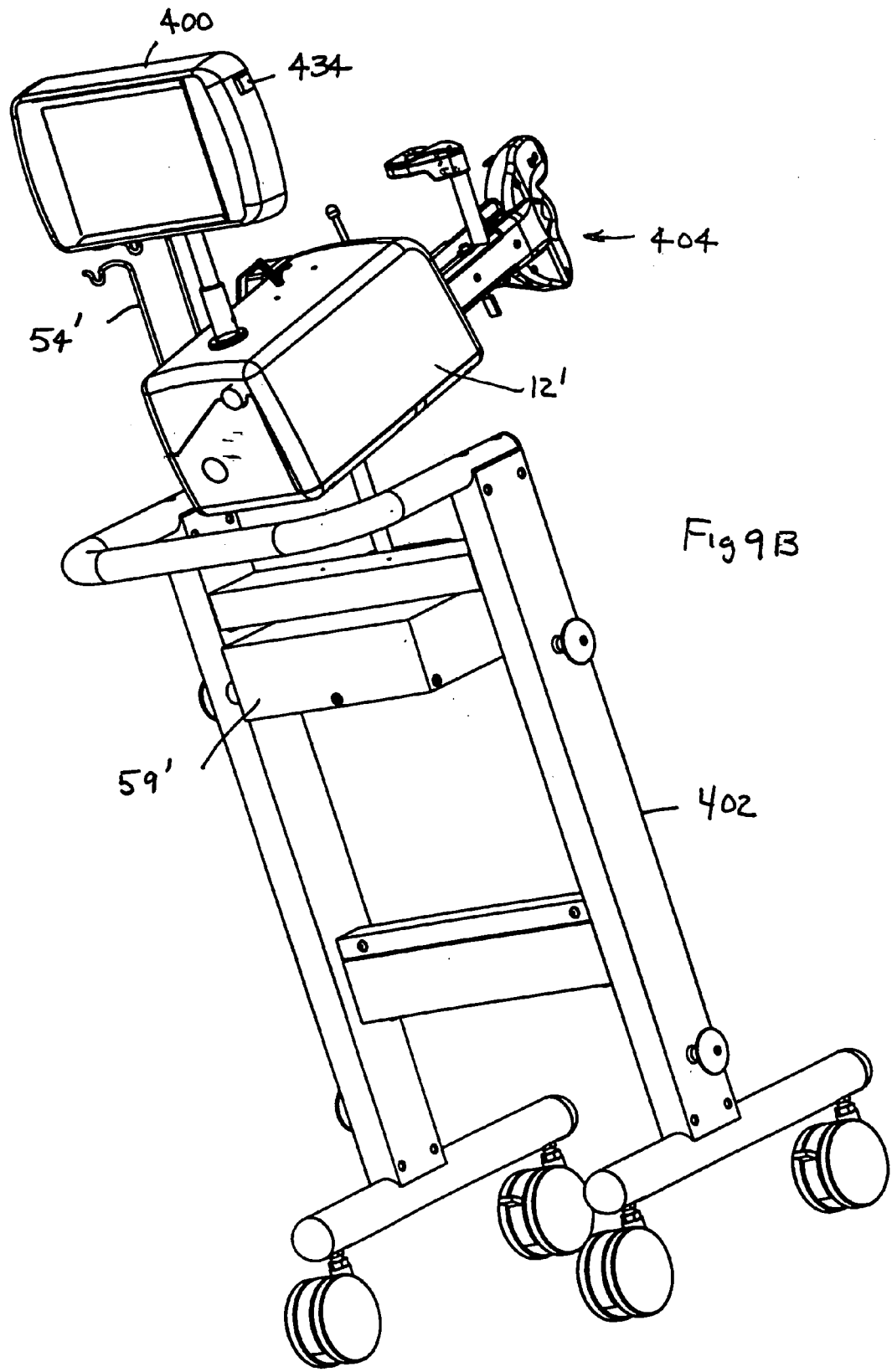

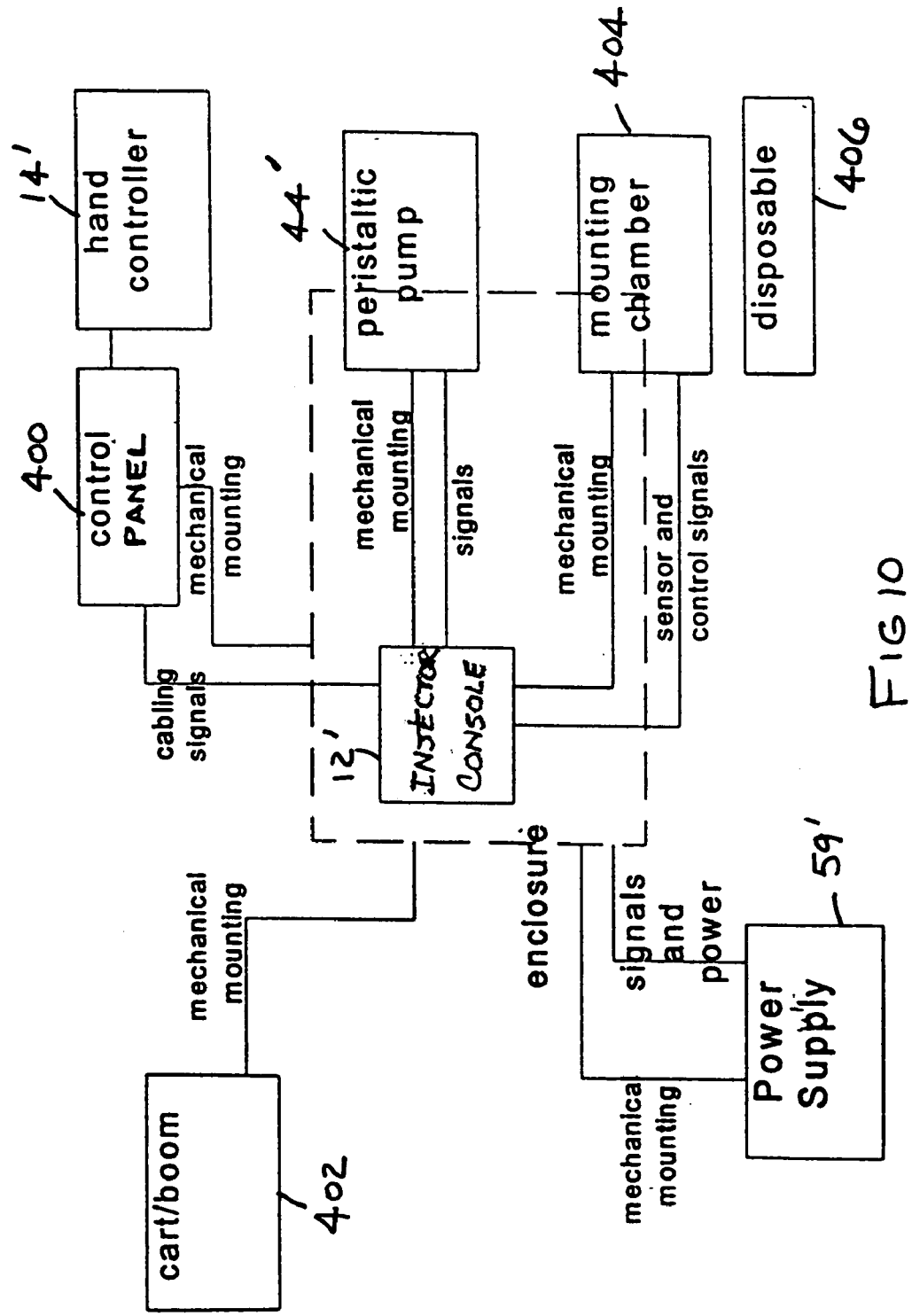

PowerUp Screen    FIG 14
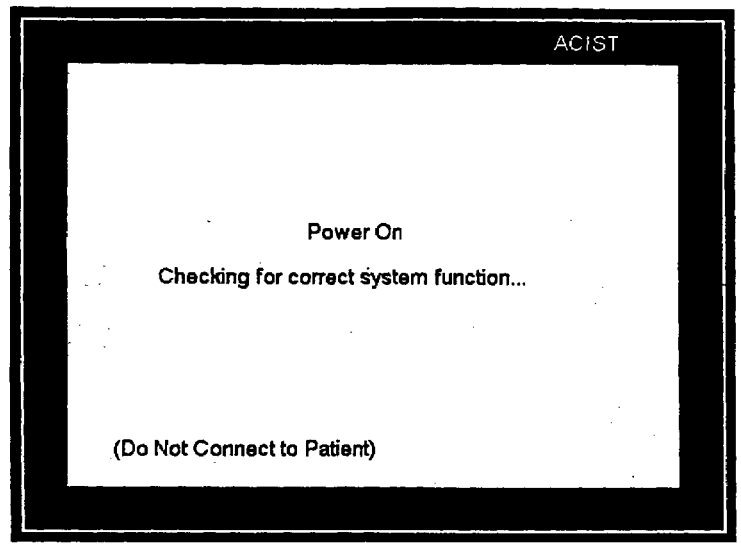
Fig. 15    Back Calibration
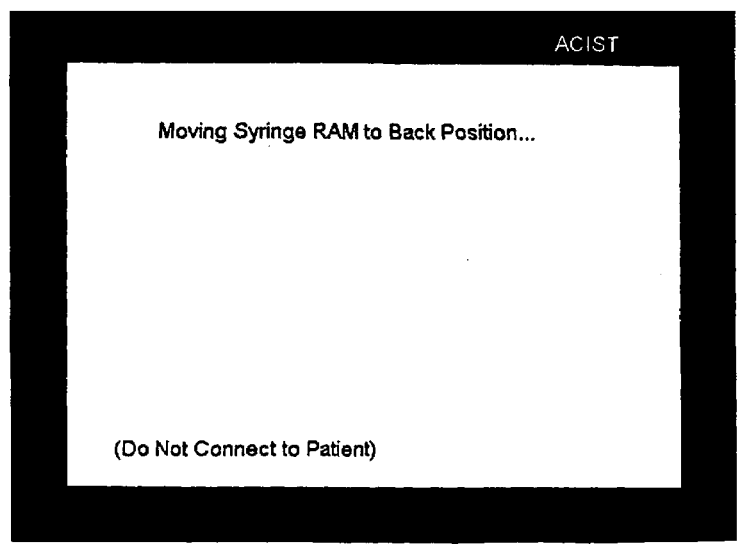

Fig. 16  Check Screen
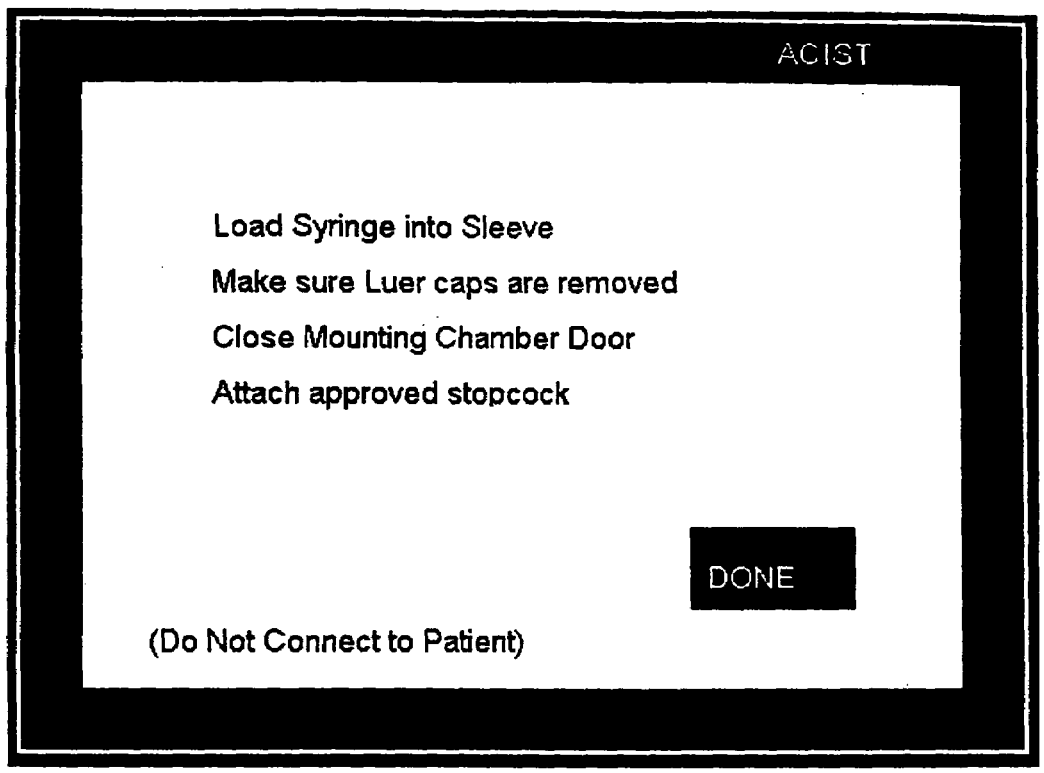
Fig. 17  Forward Calibration
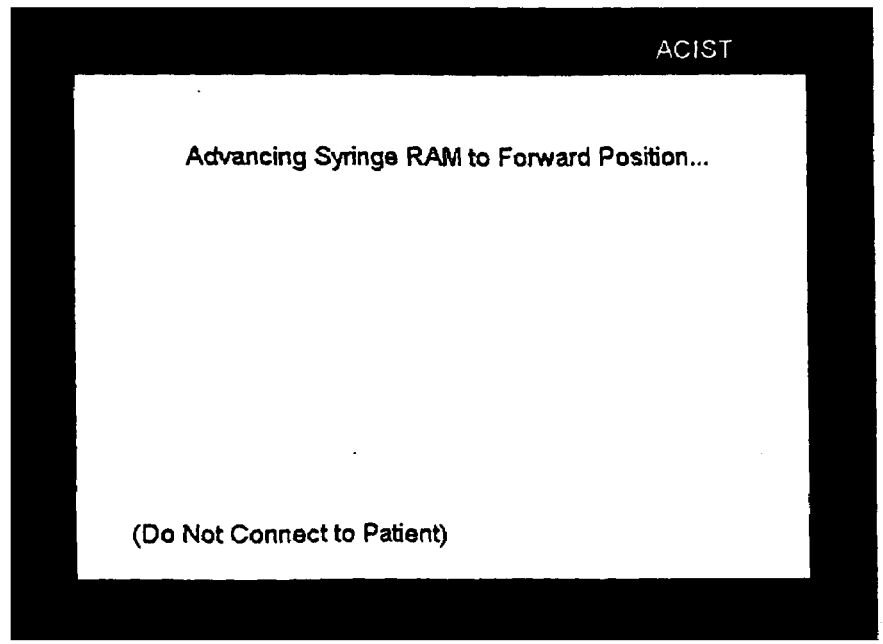

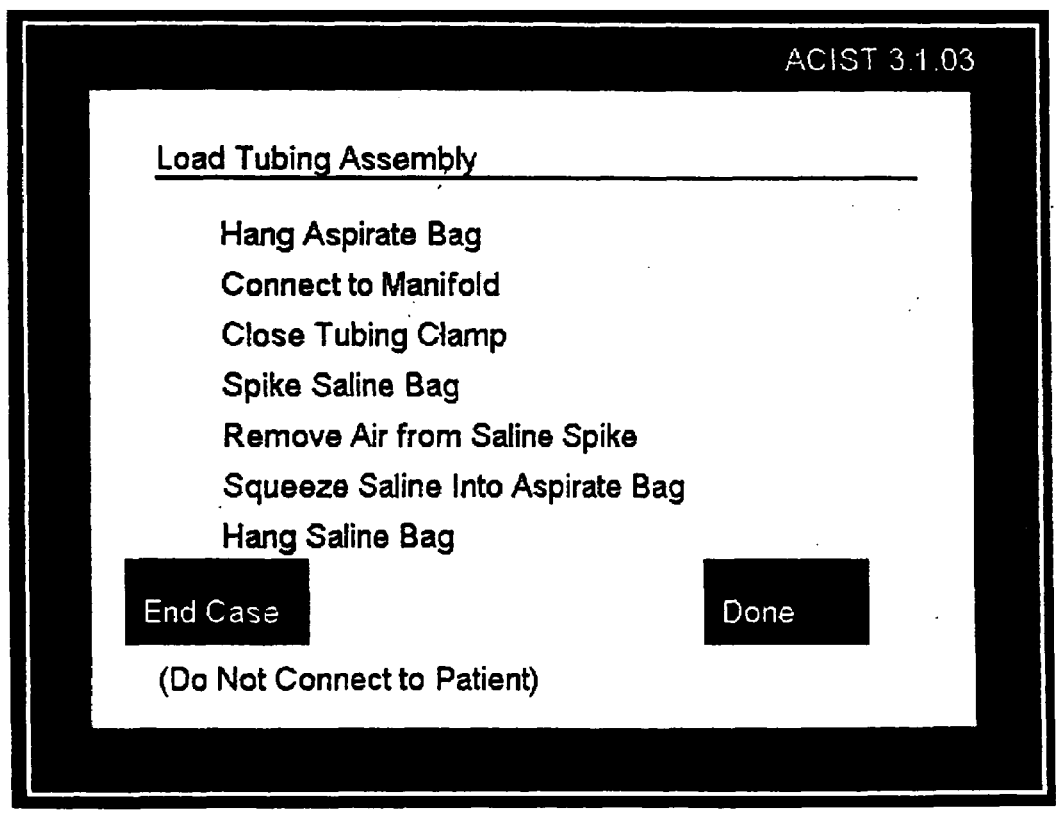
Fig 18  Instruction Screen 1

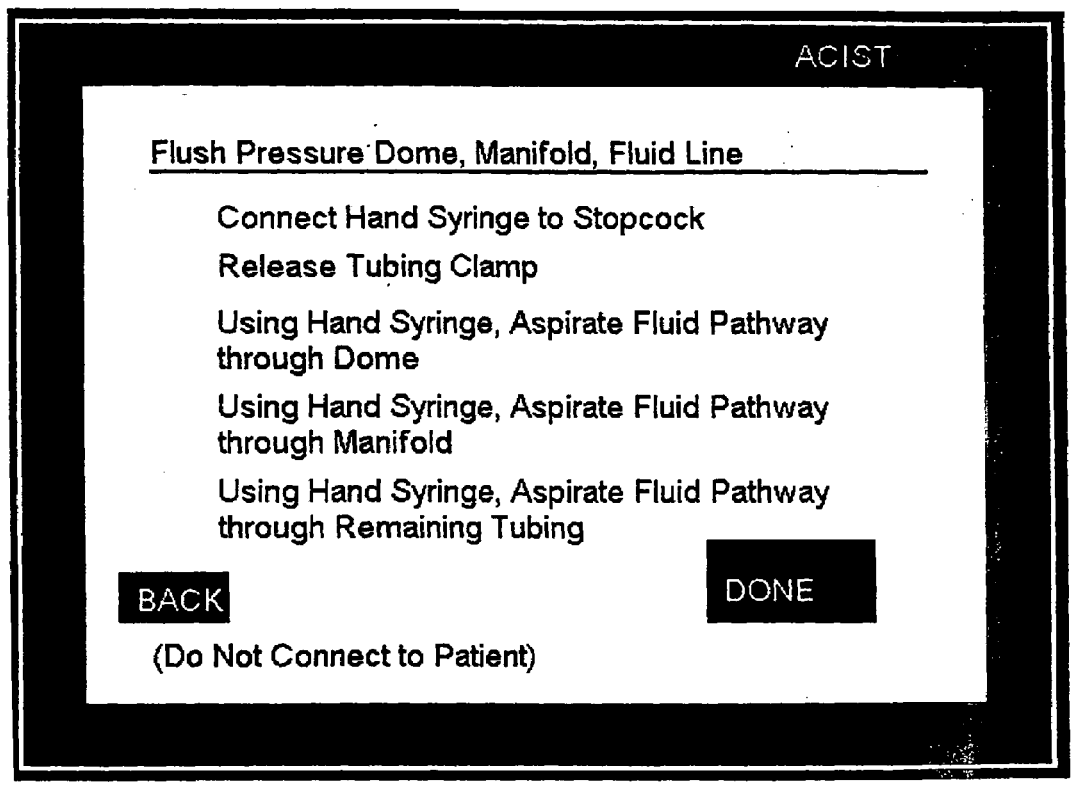
Fig 19  Instruction Screen 2

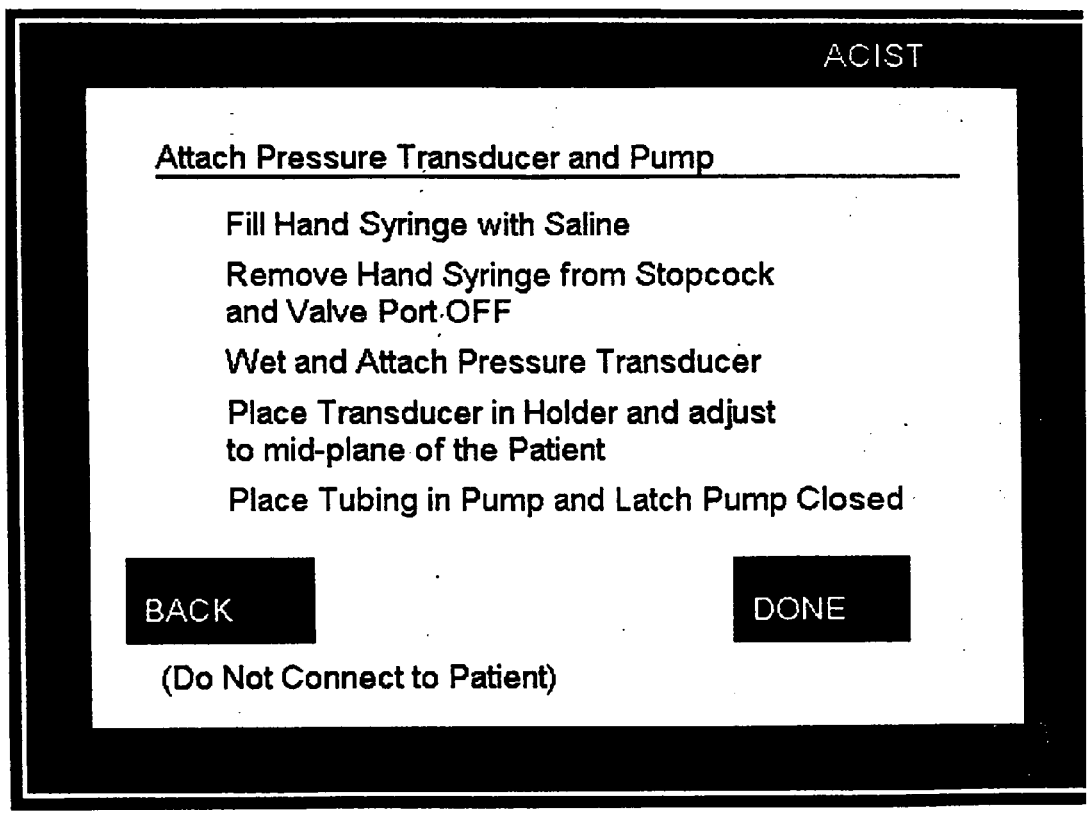
Fig. 20  Instruction Screen 3

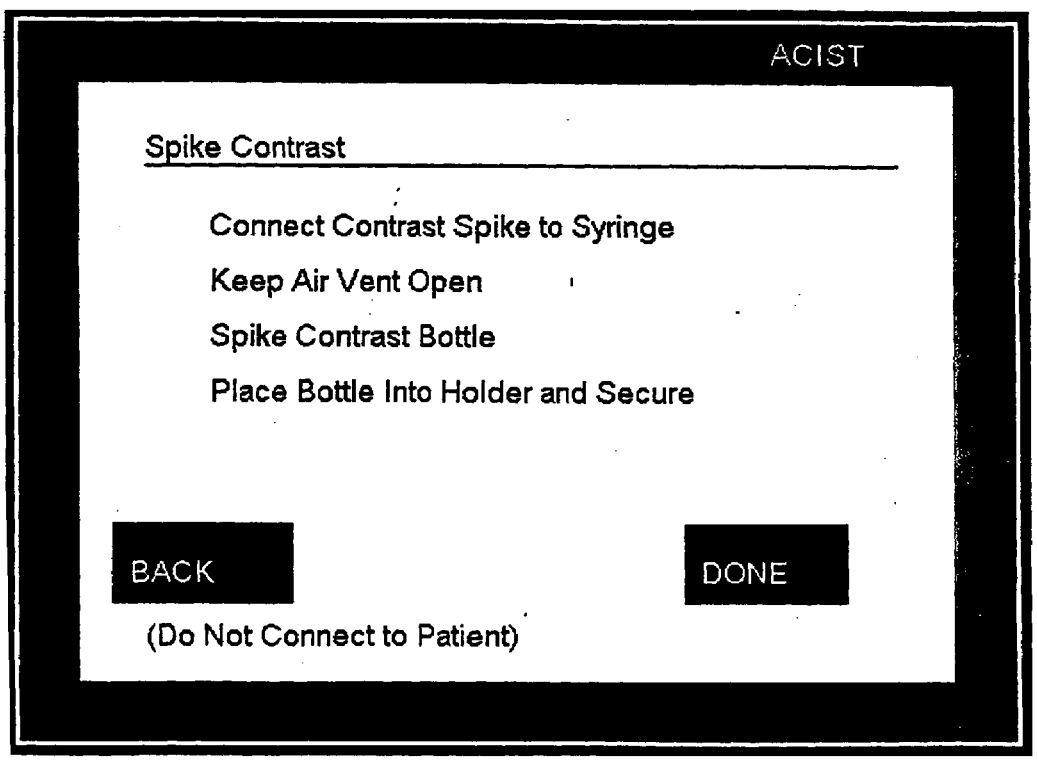
Fig 21  Instruction Screen 4

Fig 22  Ready to Fill Syringe
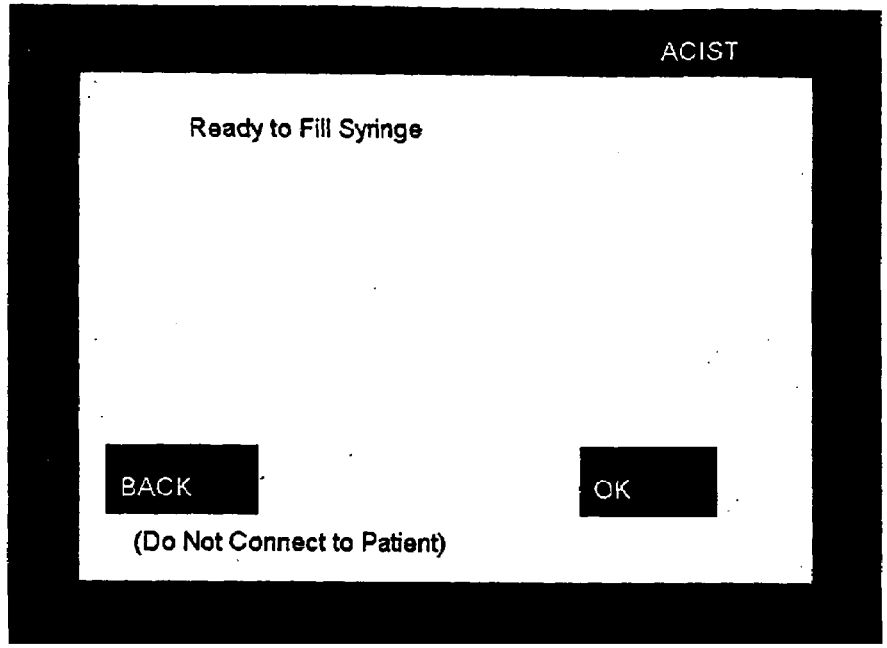
Fig 23  Filling
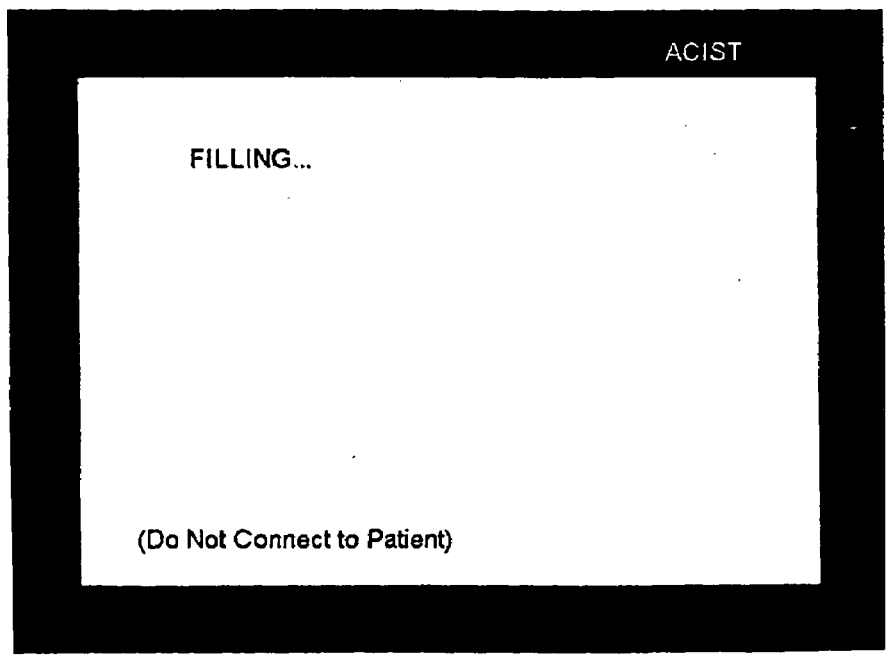

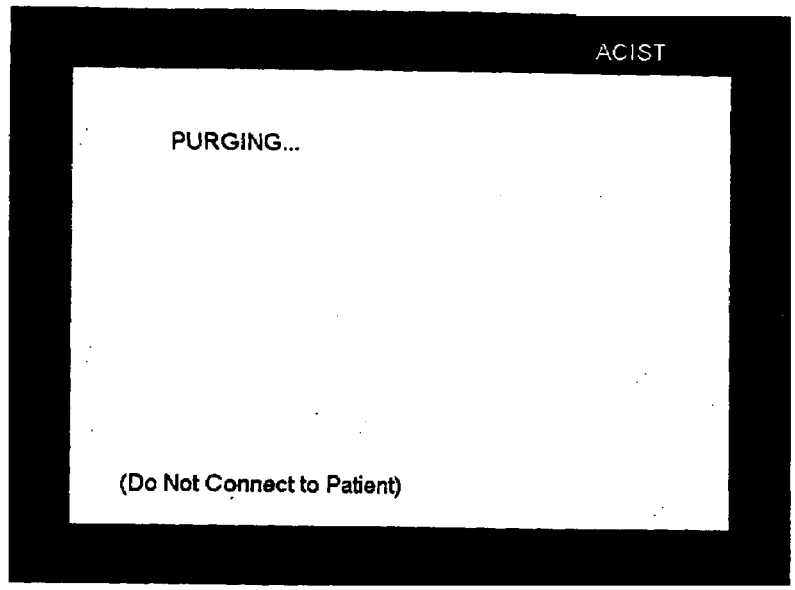
Fig 24  Purging
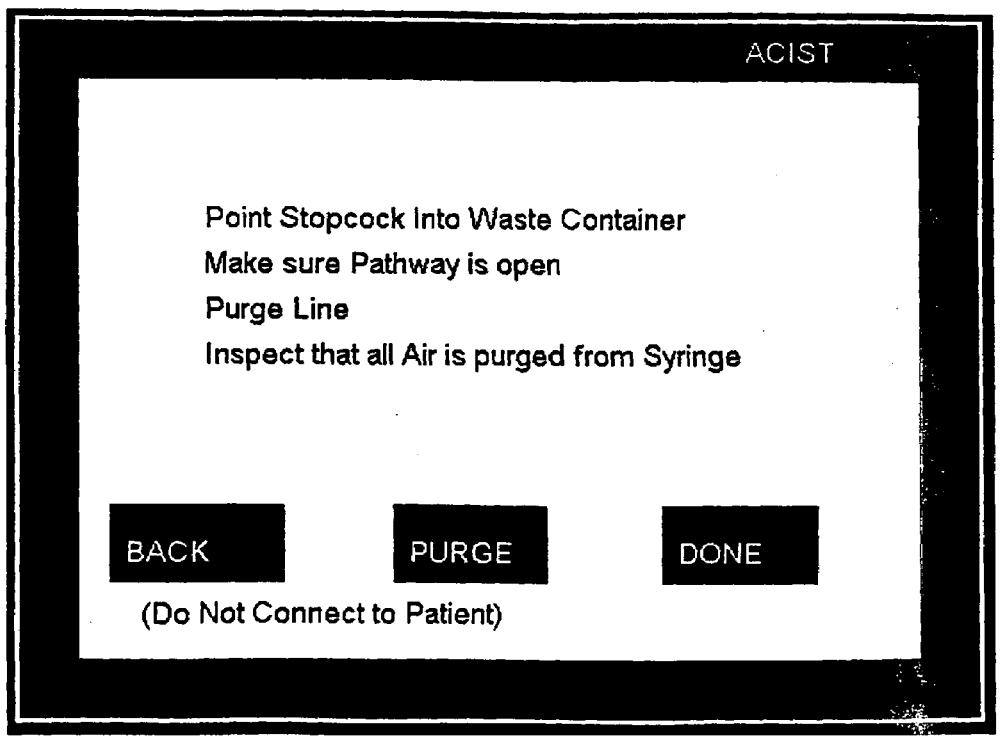
Fig 25  Line Purge

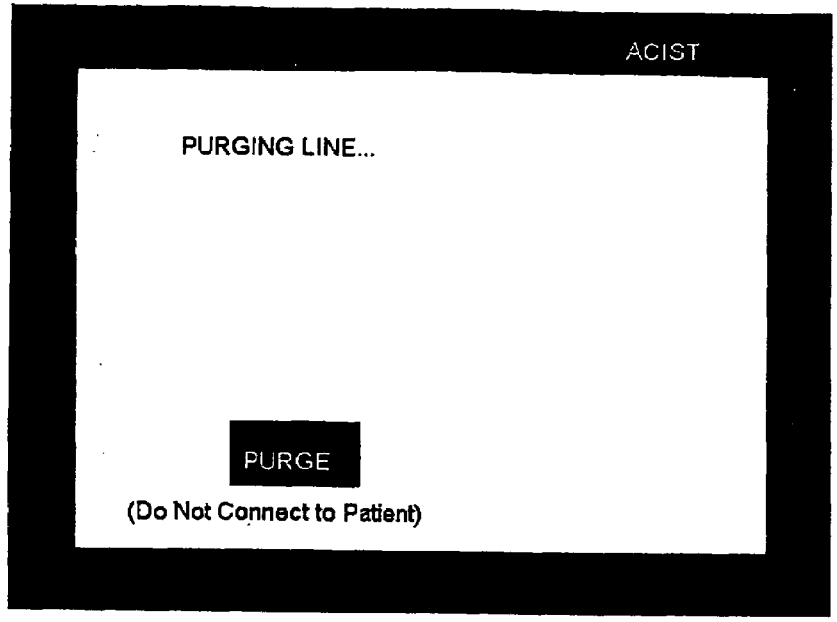
Fig 26  Purging Line
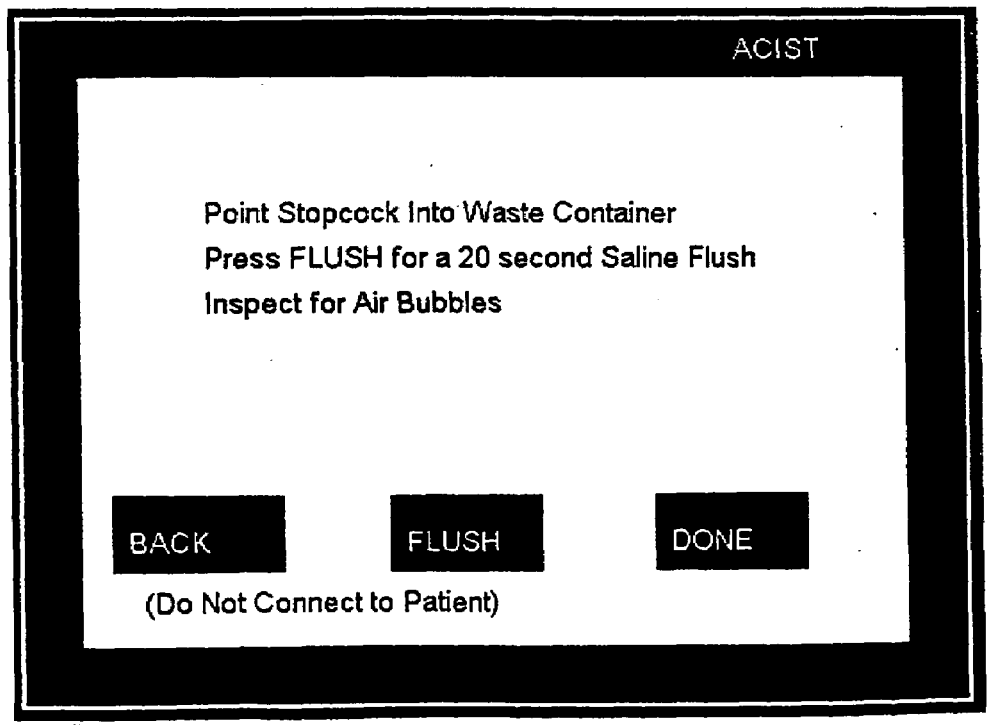
Fig. 27  Flush Screen

Fig 28  Flushing Screen
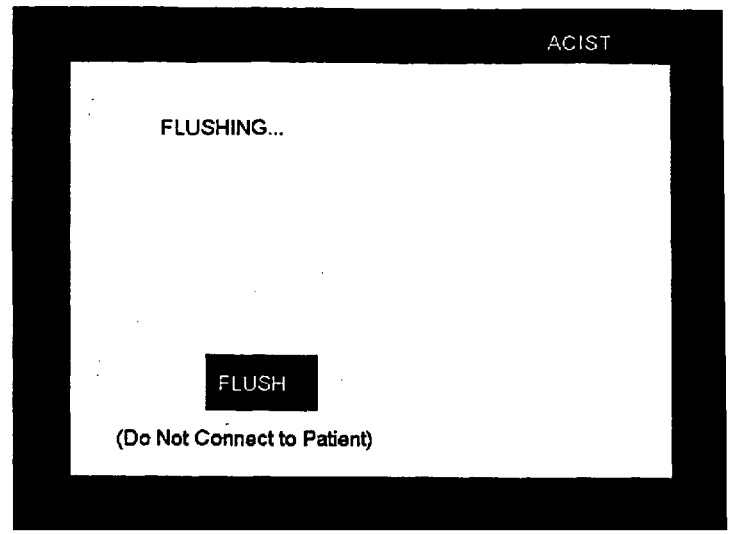
Fig 29  Final Startup Screen
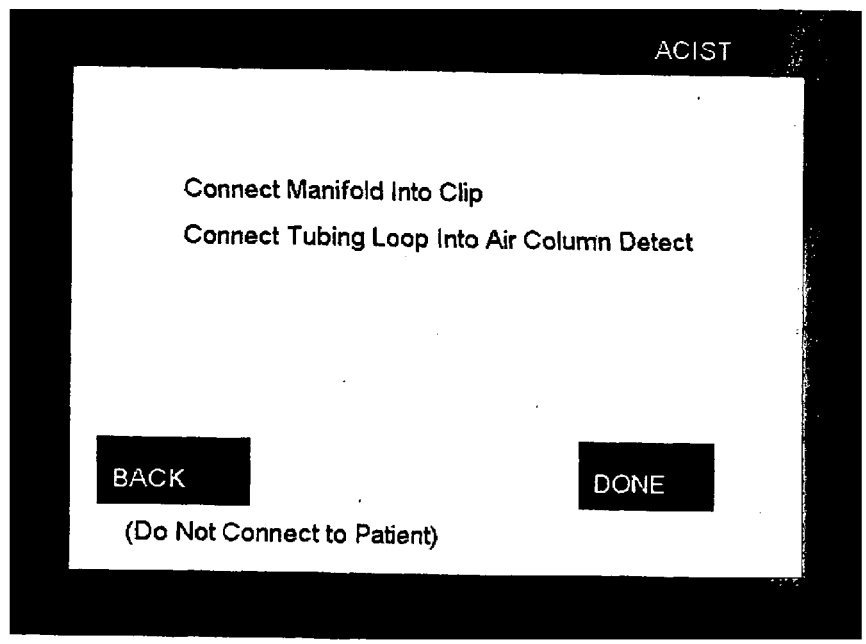

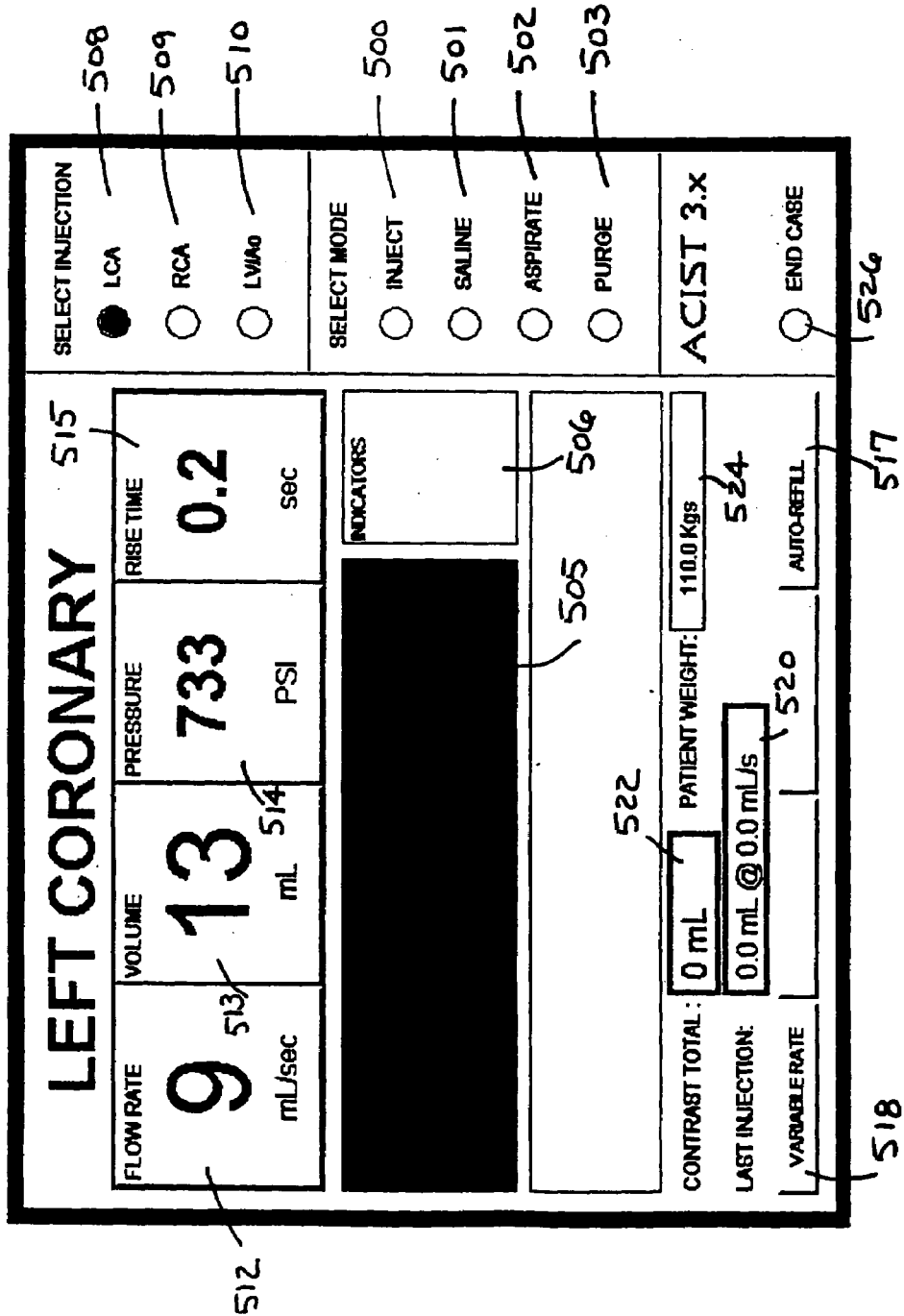

Left Coronary

| Flow Rate | Volume | Pressure | Rise Time |
|---|---|---|---|
| 9 mL/sec | 13 mL | 733 psi | 0.2 sec |

Purging... Purge
Volume (mL)
Indicators

Contrast Total: 0mL    Patient Weight: 110.0 Kgs
Last Injection: 0.0mL @ 0.0mL/s
Variable Rate          Manual Refill Select Injection
- ⊘ LCA
- ○ RCA
- ○ LV/Ao Select Mode
- ○ Inject
- ○ Saline
- ○ Aspirate
- ○ Purge ACIST 3.x
○ End Case

FIG. 34

Left Coronary

| Flow Rate | Volume | Pressure | Rise Time |
|---|---|---|---|
| 7 mL/sec | 12 mL | 500 psi | 0.2 sec |

Refilling Purge
Volume (mL)
Indicators

Contrast Total: 47mL    Physician: DR. Wilson
Last Injection: 8.0mL @ 4.0mL/s
Variable Rate          Manual Refill Select Injection
- ⊘ LCA
- ○ RCA
- ○ LV/Ao Select Mode
- ○ Inject
- ○ Saline
- ○ Aspirate
- ○ Purge ACIST 1.0
○ Display
○ End Case

FIG. 35

ANGIOGRAPHIC INJECTOR SYSTEM WITH MULTIPLE PROCESSOR REDUNDANCY

CROSS-REFERENCE TO RELATED APPLICATIONS

This application is a continuation-in-part of U.S. patent application Ser. No. 08/957,801 filed on Oct. 24, 1997, pending entitled ANGIOGRAPHIC INJECTOR SYSTEM WITH AUTOMATIC HIGH/LOW PRESSURE SWITCHING which is a continuation-in-part of U.S. patent application Ser. No. 08/946,293, filed on Oct. 7, 1997, now U.S. Pat. No. 5,800,397 which is a file wrapper continuation application of U.S. patent application Ser. No. 08/426,148 filed on Apr. 20, 1995, now abandoned which are all herein incorporated by reference. This application also incorporates by reference the contents of the following U.S. patent applications: Ser. No. 08/957,228, entitled Dual Port Syringe, filed on Oct. 24, 1997; Ser. No. 08/965,583, entitled Pneumatic Controller and Method, filed on Nov. 6, 1997; and Design application Ser. No. 29/078,023; entitled Hand-Held Pneumatic Control Device, filed on Nov. 6, 1997; all three of which are owned by a common assignee of this application.

FIELD OF THE INVENTION

This invention relates generally to angiography and/or particularly to an improved injector system for injecting medical fluids such as radiographic contrast fluids into living organisms.

BACKGROUND OF THE INVENTION

Angiography is a procedure used in the treatment of cardiovascular conditions including abnormalities or restrictions in blood vessels towards, the network of passageways through which blood travels in a human or animal body. During angiography, a radiographic contrast material is injected through a catheter into a vein or artery, which then passes to vascular structures in fluid communication with the vein or artery. When X-rays are passed through the region of the body into which the material is injected, they are absorbed by the contrast material, providing radiographic images of the desired vascular structure(s). The images can be recorded on film or video tape and/or displayed on a fluoroscope monitor. The images can be used for many purposes, as for example, diagnostics and for operative procedures such as angioplasty, wherein a balloon is inserted into a vascular system and inflated to open a stenosis.

The contrast material can be injected into the catheter by either manual or automated injection systems. While the apparatus for injecting the contrast material can vary, most current systems include a syringe operatively connected with the catheter. The syringe has a chamber for holding the contrast material and a plunger reciprocally moveable within the chamber. The contrast material is suctioned into the chamber when the plunger is moved to create a partial vacuum within the chamber. A reversal of the plunger direction first forces air out of the chamber and then delivers the contrast material to the catheter at a rate and volume determined by the speed of movement of the plunger.

In a manual system the user or operator loads the syringe and ejects air from the chamber before connecting the syringe to the catheter. The user of a manual system adjusts the rate and volume of injection by altering the manual force applied to the plunger. The maximum injection pressure for manual systems is typically limited to 150 p.s.i. (i.e. the maximum pressure that can be applied by the human hand), and the maximum quantity of fluid is about 12 cc. Such manual systems typically do not accommodate any safety features such as the restriction or prevention of injections outside of predetermined injection parameters (such as rate or pressure), and generally do not include active sensors or alarms to detect air bubbles or other hazards.

Angiography can include the injection of fluids other than the contrast material. For example, a saline flush and/or the injection of fluid medications may be desired. One of the most commonly used manual injection systems includes a valve mechanism having a plurality of manually activated valves that the operator selectively opens and closes to direct flow of the desired fluids into or out of fluid channels connected to the syringe or catheter. When the operator aspirates or injects the contrast fluid into or out of the syringe chamber, the fluid flows through the path of least resistance as directed by the relative positions of the valves. When changing the valve positions, one or more fluids may be selectively injected.

A number of motorized and automated injection systems have appeared in the art, to address the limitations and dangers associated with the manual injection systems. Most such automated systems use a syringe with a linear actuator whose movement is regulated by an electronically controlled motor. For a description of such typical systems, the reader is referred to U.S. Pat. No. 4,812,724 issued on Mar. 14, 1989 and to U.S. Pat. No. 4,854,324 issued on Aug. 8, 1989. Such automated injection systems are generally fixed rate injection systems, wherein an operator enters a parameter representing the desired fixed volume of contrast material and the desired fixed rate of injection into the system. Such systems typically include an initial specified rate of flow increase leading to a final rate of injection, until the entire volume of contrast material is injected. There is no interactive control between the operator and the system, except to start or stop the injection. Any change of flow rate must occur by stopping the injector and resetting the parameters. The automated nature of such machines, however, offers the addition of injection speed and volume limit control features that were not available with the earlier manual injection systems.

Since the optimal flow rate can vary considerably between patients, the lack of ability of such prior art systems to vary the rate of injection during an injection procedure can result in suboptimal quality of angiographic studies. In cardiovascular systems, the rate and volume of contrast injection depends on the volume and flow rate within the blood vessel or other cardiovascular chamber being injected. In many or most cases, these parameters are not known precisely and can change rapidly during the injection procedure as the patient's cardiovascular system conditions change in response to such things as, for example, drugs, illness or normal physiology. Consequently, the initially selected volume or flow rate parameters for an injection of contrast material may be insufficient to outline a desired structure on an X-ray image, thereby necessitating another injection. Conversely, an excessive flow rate may injure the cardiovascular vessel being injected, cause the catheter to be displaced relative to the patent or lead to toxic effects (such as abnormal heart rhythm) from contrast material overdose. Our prior cross-referenced applications, hereby fully incorporated by reference, address the prior art's lack of ability to vary the injection parameters during an injection procedure.

While the prior automated systems have significantly improved the accuracy and reliability of angiography injection procedures, the known systems have not been as user friendly as desired, have not had automated capability to determine default injection parameters unique to the physiology or other values of the patent to be treated, and have not incorporated pro-active safety features in their system designs.

All automated systems necessarily require some type start-up procedure to be conducted prior to initializing an injection procedure with the system on a patient. Heretofore, such automated systems have not been particularly user friendly, but have required the operator or set-up technicians using the system to follow a set-up setup and initialization procedure according to instructions in a user manual. Besides the nuisance factor associated with the care and handling of such manuals, it is possible to mistake a manual of one injector with that of another or to use an outdated manual that does not include the most current initialization procedures and/or parameters. A further shortcoming of prior automated systems is that such systems do not maintain and display to the operator the actual real-time injection parameters existing at any instant of the injection procedure, or the cumulative amount of contrast material that has been administered to a patient from the beginning of the injection procedure, to the present. Heretofore, accumulating and maintaining a record of such cumulative information for an injection procedure has been a responsibility of the operator.

Known automated injection systems typically require entry of the following injection parameters: the volume of contrast material to be injected, the flow rate of injection, the maximum permitted injection pressure and the rate of change of injection flow rate (i.e. the rise time). Since the three parameters of flow, volume and duration are related, if any two are known, the third can be calculated. Known systems either require the operator to determine the desired parameters for an injection procedure, or allow the operator to recall parameters that the operator has stored in the system's memory from a prior procedure. Some injection systems also include stored default settings for the parameters associated with different types of injection procedures that can be used by the operator. A deficiency of such prior systems, however, is that such default and stored parameter values are arbitrarily determined and are not generally determined using unique properties or values or characteristics of the patient being treated.

Known automated injection systems also have not incorporated pro-active safety features in their system designs. While a microprocessor has been used in prior systems for providing primary automated control of the syringe plunger movement, back-up safety systems for checking on the multiprocessor's effectiveness have not been of a pro-active nature, but have been of a type that simply have the capability of interrupting or stopping an injection if the safety system determined that the injection procedure is being performed outside of one or more of the predetermined injection parameters. The present invention addresses these and other deficiencies of known automated angiographic injection systems.

SUMMARY OF THE INVENTION

This invention provides an automated angiographic injection system that is extremely flexible and user friendly and which provides real-time instantaneous injection parameter information to the operator. The system features a liquid crystal display screen that displays a sequence of start-up instructions to the operator without requiring additional manuals or hard copy instructions during such procedures. User communication with the system's microprocessor(s) is readily and accurately permitted through touch-responsive pads on the visual display. Since the system microprocessor(s) always includes the most updated system intelligence, there is no chance of operator error as a result of using outdated manuals. As the injection procedure progresses, the system microprocessor(s) instantaneously communicates with the operator, providing the operator with real-time information including the instantaneous value of the injection parameters and the cumulative volume of contrast material that has been injected into the patient. Such information prevents administration of toxic doses of the contrast material to the patient that might otherwise occur as a result of successive injections during an extended diagnostic or treatment procedure.

This invention further employs an injection parameter determination procedure that calculates the preferred injection parameter default values before the initiation of each injection procedure. The preferred injection parameter default values are calculated using algorithms that use physiological values or information such as weight, age, wellness, cardiovascular peculiarities, etc. that are unique to the patient being treated. Such determination procedure enables the factoring in of changes that may have occurred to the patient since the patient's last injection procedure, and does not simply rely on outdated previous memory-stored information on the patient. According to one aspect of the invention, such algorithmically determined parameters are employed in either an automated fixed rate or operator initiated variable rate injection mode of operation to optimally deliver the contrast material to the patient.

This invention further contemplates the system incorporating a plurality of active intelligence systems such as microprocessors, for providing simultaneous servicing of system sensors and dual redundancy safety feature for critical safety injection procedures. Such system enables redundant active decision-making capability that does not simply require termination of a function in the event of errant signals generated by one microprocessor. According to one aspect of the invention an injector system is provided that simultaneously uses an embedded core operating system particularly configured for sensing and hardware control, along with a personal computer (PC) based operating system that readily provides operator interface capabilities, for providing a multiple redundant intelligence control system.

According to yet a further aspect of the invention, control of the prime mover of the contrast material injecting syringe plunger is accurately and efficiently achieved with a commercially available servo amplifier and the use of unique nested control loops.

According to one aspect of the invention there is provided a method of controllably delivering medical fluid from an angiographic injection apparatus to a patient, comprising: (a) providing the angiographic injection apparatus with a fluid delivery mechanism for injecting the medical fluid into a patient; and (b) controlling the medical fluid injection from the fluid delivery mechanism with at lest two computers operatively connected with said fluid delivery mechanism. According to preferred configurations of the invention one of the computers is preferably of a PC-type and one is preferably of an embedded core type. Such control of the injection procedure with at least two computers provides independent dual redundancy control of key operative functions of the delivery mechanism by separate ones of the computers.

According to yet a further aspect of the invention there is provided an angiographic injector system, comprising: (a) a device for injecting a medical fluid into a patient; (b) drive means operatively connected with said device for causing the device to inject the medical fluid; and (c) a plurality of computers operatively connected with the drive means for actively controlling the drive means. According to a further feature of the invention, the computers actively control the drive means to control key injection parameters of the device including such parameters as flow rate and volume of the medical fluid. According to a preferred configuration of the invention, the injection device comprises a syringe having a moveable piston and the drive means includes a motor operatively connected to move the piston. In such configuration, the computer(s) actively monitor operable parameters of the motor such as motor speed and motor current to provide dual redundancy safety control circuits for the system.

According to yet a further aspect of the invention, there is provided a control system for use in combination with an angiographic injection system of the type having a syringe apparatus for discharging a medical fluid into a patient, a syringe control network operatively connected to the syringe apparatus for causing the syringe apparatus to controllably discharge said fluid, comprising: at least two computers of a type having independent intelligence processing capability, operatively connected to the syringe control network for monitoring operation of the syringe apparatus and the syringe control network, for independently providing control signals to the syringe control network.

According to yet a further aspect of the invention there is provided a method for injection of medical fluid into a patient, comprising the steps of: (a) providing an angiographic injection machine; (b) entering at least one patient value into the machine prior an injection; (c) calculating within the machine at least one injection parameter in response to said entered patient value; and (d) displaying the calculated injection parameter to a user of the machine prior to the injection. The invention further includes the step of entering the calculated injection parameter into the machine as a default value for the injection parameter, which is usable by the machine in performing an injection, and further the step of actually performing an injection with the machine, using the entered injection parameter. According to a preferred algorithm determination, the patient value used in determining the calculated injection parameter is patient weight, and the determined injection parameter can include injection flow rate of the medical fluid, volume of the medical fluid, rise time of the injection flow rate and a pressure limit for the medical fluid during an injection procedure.

According to yet a further aspect of the invention there is provided an angiographic injector system, comprising: (a) a device for injecting a medical fluid into a patient; (b) control means operatively connected with the device for controllably causing the device to inject the medical fluid in response to at least one injection parameter; (c) input means suitable for receiving an input signal corresponding to a patient physiological value and for providing a patient value signal in response thereto; (d) calculating means operatively connected to receive the patient value signal and for determining a patient related injection parameter in response thereto; and (e) display means operatively connected with the calculating means for displaying the patient related injection parameter external of the injection system. Such injection system further contemplates means operatively connected with the calculating means and with the control means for delivering the patient related injection parameter to the control means, wherein the control means controls the device at least partially in response to the patient related injection parameter.

According to yet a further aspect of the invention there is provided an angiographic injector system, comprising: (a) a device for injecting a medical fluid into a patient; (b) drive means operatively connected with a device for causing the device to inject the medical fluid; (c) at least one computer operatively connected with the drive means for actively controlling the drive means to cause the device to controllably inject the medical fluid; (d) a user interface display operatively coupled with the computer for receiving input signals from a user and for displaying information to the user; and (e) means operatively connecting the user interface display with the computer to provide the input signals to the computer and for providing information from the computer to the display. According to yet a further aspect of the invention, the user interface display includes a touch pad overlying a visual display screen which is preferably of a liquid crystal type. According to one aspect of the invention, the computer provides the information to the user interface display in a manner configured to display a sequence of interactive set-up screens to a user. The computer also provides data for displaying real time output parameters related to the injection procedure of a system such as an accumulated injection volume or the instantaneous flow rate occurring during an injection. According to yet a further aspect of the invention, the user interface display includes selectable input receptors activatable by a user to select different injection procedures such as for the study of the left coronary, the right coronary or the left ventricle and aorta portion of a human anatomy. The selectable input receptors may also be used to select different injection parameters or to select either fixed rate or variable rate injection modes of operation. According to yet a further aspect of the invention, the drive means can include a motor with a servo-amplifier drive for controlling the device and a nested control loop circuit for providing accurate operative control of the motor.

BRIEF DESCRIPTION OF THE DRAWINGS

Referring to the Drawings, wherein like numbers represent like parts throughout the several views:

FIG. 4 illustrates front panel controls and displayes of a preferred embodiment of the injector system of the present invention;

FIGS. 7A-7D illustrate the operation of the inlet check valve and manifold during contrast fill, air purge, and patient inject operations;

FIGS. 8A-8C illustrate operation of the inlet check valve in greater detail;

FIGS. 9A and 9B are perspective views illustrating a second embodiment configuration of an angiographic injector system of the present invention;

FIG. 10 is a mechanical block diagram illustrating the mounting configuration of the portions of the system disclosed in FIG. 9;

FIG. 14 is an illustration of a Power Up screen of the display of the system of FIG. 11;

FIG. 15 is an illustration of a Back screen of the display of the system of FIG. 11;

FIG. 16 is an illustration of a Check Screen screen of the display of the system of FIG. 11;

FIG. 17 is an illustration of a Forward screen of the display of the system of FIG. 11;

FIG. 18 is an illustration of a First Start-Up Instruction screen of the display of the system of FIG. 11;

FIG. 19 is an illustration of a Second Start-Up Instruction screen of the display of the system of FIG. 11;

FIG. 20 is an illustration of a Third Start-Up Instruction screen of the display of the system of FIG. 11;

FIG. 21 is an illustration of a Fourth Start-Up Instruction screen of the display of the system of FIG. 11;

FIG. 22 is an illustration of a Ready to Fill Syringe screen of the display of the system of FIG. 11;

FIG. 23 is an illustration of a Syringe Filling Notice screen of the display of the system of FIG. 11;

FIG. 24 is an illustration of a Purging Notice screen of the display of the system of FIG. 11;

FIG. 25 is an illustration of a Line Purge Instruction screen of the display of the system of FIG. 11;

FIG. 26 is an illustration of a Purging Line Notice screen of the display of the system of FIG. 11;

FIG. 27 is an illustration of a Final Saline Flush Instruction screen of the display of the system of FIG. 11;

FIG. 28 is an illustration of a Saline Flushing Notice screen of the display of the system of FIG. 11;

FIG. 30 is an illustration of the MAIN display screen of the system of FIG. 11;

FIG. 32 is an illustration of the MAIN display screen of FIG. 30 illustrating the keypad that is displayed when the Fixed Rate mode of operation is selected;

FIG. 33 is an illustration of the MAIN display screen of FIG. 30 illustrating the keypad that is displayed when the Variable Rate mode of operation is selected;

FIG. 34 is an illustration of the MAIN display screen of FIG. 30, illustrating operation in a Manual Purging mode;

FIG. 35 is an illustration of the MAIN display screen of FIG. 30, illustrating operation in a Manual Refilling mode;

DETAILED DESCRIPTION OF THE PREFERRED EMBODIMENT

Figure 1:
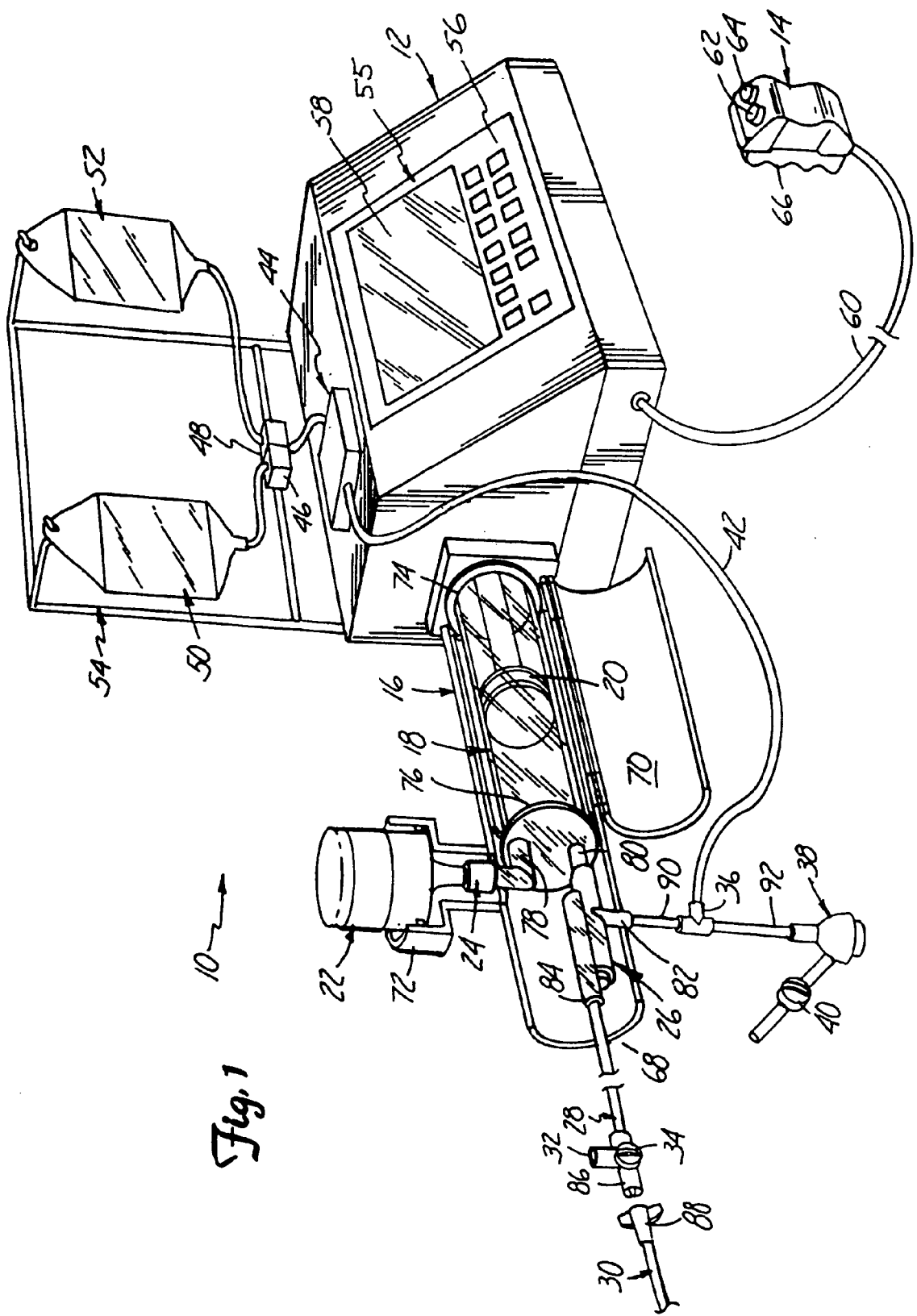
FIG. 1 is a perspective view illustrating a preferred embodiment of an angiographic injector system of the present invention.

As will be appreciated upon a more detailed description herein, the principles of this invention can be applied to many different physical configurations of automated angiographic injector systems. An example of one such system, as described in more detail in U.S. patent application Ser. No. 08/426,149 referenced above and herein fully incorporated by reference, will be generally described below. It will be understood that while specific angiographic system(s) will be described with respect to preferred embodiments of the invention, the principles of this invention are not limited to use in the preferred embodiments described. Referring to the Drawings, FIG. 1 shows an angiographic injector system 10 for injecting radiographic contrast material into a blood vessel under interactive physician control. System 10 includes main console 12, hand held remote control 14, syringe holder 16, syringe body 18, syringe plunger 20, radiographic material reservoir (bottle) 22, one-way valve 24, manifold 26, high pressure tube 28, catheter 30, patient medication port 32, three-way stop-cock 34, T-connector 36, pressure transducer 38, stop-cock 40, tubing 42, peristaltic pump 44, saline check valve 46, waste check valve 48, saline bag 50, waste bag 52, and bag support rack 54.

Console 12 houses the electrical controls for system 10, together with the motors which drive piston 20 and peristaltic pump 44. On the front surface of console 12, user interface 55 provides control switches 56 and display 58 through which the user may enter control settings and monitor the operational state of system 10. The console can be free-standing, preferably configured for mounting on a transport cart assembly.

Electrical power is provided to all electrical components of the system by an appropriate power supply which also provides electrical safety isolation from the main power source. The power supply can be located within the console 12, but is preferably mounted separately therefrom either on a wall or on a mounting cart.

Remote control 14 is connected to console 12 by cable 60 (although in other embodiments remote control 14 may be connected by a wireless connection such as an RF, infrared optic, or ultrasonic link). Remote control 14 is, in the embodiment shown in FIG. 1, a hand-held control which includes reset and saline push button switches 62 and 64, respectively, and flow rate control lever or trigger 66. By squeezing trigger 66, the user can provide a command signal to console 12 to provide a continuously variable injection rate.

Syringe holder 16 projects from the left hand side of console 12. Syringe holder 16 is preferably a clear material, and includes a half cylindrical back shell 68, a half cylindrical front door 70 (which is shown in open position in FIG. 1), and reservoir holder 72.

Syringe 18 is a transparent or translucent plastic cylinder having its open end 74 connected to console 12. Closed end 76 of syringe 18 contains two ports: upper port 78 and lower port 80.

Plunger 20 is movable within syringe body 18. Plunger 20 is connected to, and driven by a motor located within console 12.

Radiographic contrast material reservoir 22 is connected through one-way check valve 24 to upper port 78. Radiographic contrast material is drawn from reservoir 22 through check valve 24 and upper port 78 into the pumping chamber defined by syringe body 18 and plunger 20. Check valve 24 is preferably a weighted one-way valve which permits air to flow from syringe body 18 back into reservoir 22, but will not permit radiographic contrast material to flow from syringe body 18 to reservoir 22. This permits automatic purging of air from the system, as will be described in more detail later.

Lower port 80 of syringe body 18 is connected to manifold 26. Manifold 26 includes a spring biased spool valve which normally connects transducer/saline port 82 and patient port 84. When radiographic contrast material is to be injected, the pressure of the radiographic material causes the spool valve to change states so that lower port 80 is connected to patient port 84.

High pressure tube 28 is a flexible tube which connects patient port 84 to catheter 30. Three-way stop-cock 34 is located at the distal end of tube 28. Rotatable luer lock connector 86 is connected to stop-cock 34 and mates with luer connector 88 at the proximal end of catheter 30. Stopcock 34 either blocks flow between tube 28 and catheter 30, permits flow, or connects medication port 32 to catheter 30.

In addition to injecting radiographic material into a patient through catheter 30, system 10 also permits other related functions to be performed. A device for delivering the patient medication (not shown in FIG. 1) may be connected to medication port 32 when medication is to be delivered through catheter 30 to the patient.

When catheter 30 is in place in the patient, and an injection of radiographic contrast material is not taking place, pressure transducer 38 monitors the blood pressure through the column of fluid which extends from catheter 30, tube 28, patient port 84, manifold 26, transducer/saline port 82, tubing 90, T-connector 36, and tubing 92. Transducer 38 has an associated stop-cock 40 which allows transducer 38 to be exposed to atmospheric pressure and also allows for removal/expulsion of trapped air so the dome chamber of transducer 38 can be flushed with saline.

Peristaltic pump 44 supplies saline solution from bag 50 through saline check valve 46, tubing 42, T-connector 36 and tubing 90 to saline port 82. When peristaltic pump 44 is operating to supply saline solution, the saline solution is supplied through manifold 26 to patient port 84 and then through tube 28 to catheter 30.

Peristaltic pump 44 also operates in an opposite direction to draw fluid from catheter 30 and through tube 28, manifold 26, tubing 90, T-connector 36 and tubing 42 to waste check valve 48 and then into waste collection bag 52.

In a preferred embodiment of the present invention, syringe body 18, manifold 26, tube 28, catheter 30, T-connector 36, tubing 42, check valves 46 and 48, bags 50 and 52, and tubing 90 and 92 are all disposable items. They must be installed in system 10 each time an angiography procedure is to be performed with a new patient. Once system 10 is set up with all the disposable items installed, door 70 is closed, and syringe body 18 filled with contrast material and purged of air, the user (typically a physician) enters into system 10 the safety parameters that will apply to the injection of radiographic contrast material. These safety parameters typically include the maximum amount of radiographic contrast material to be injected during any one injection, the maximum flow rate of the injection, the maximum pressure developed within syringe body 18, and the maximum rise time or acceleration of the injection. To actuate an injection of contrast material, the user operates remote control 14 by squeezing trigger 66. Within the preset safety parameters, system 10 causes the flow rate of the injection to increase as the force or distance of travel of trigger 66 is increased.

Typically, the user will meter the amount and rate of contrast material injected based upon continuous observation of the contrast outflow into the structure being injected using fluoroscopy or other imaging methods. System 10 allows the user to tailor the contrast injections to the needs of the patient, thereby maximizing the quality of the procedure, increasing the safety, and reducing the amount of contrast material required to perform the fluoroscopic examination.

Figure 2A:
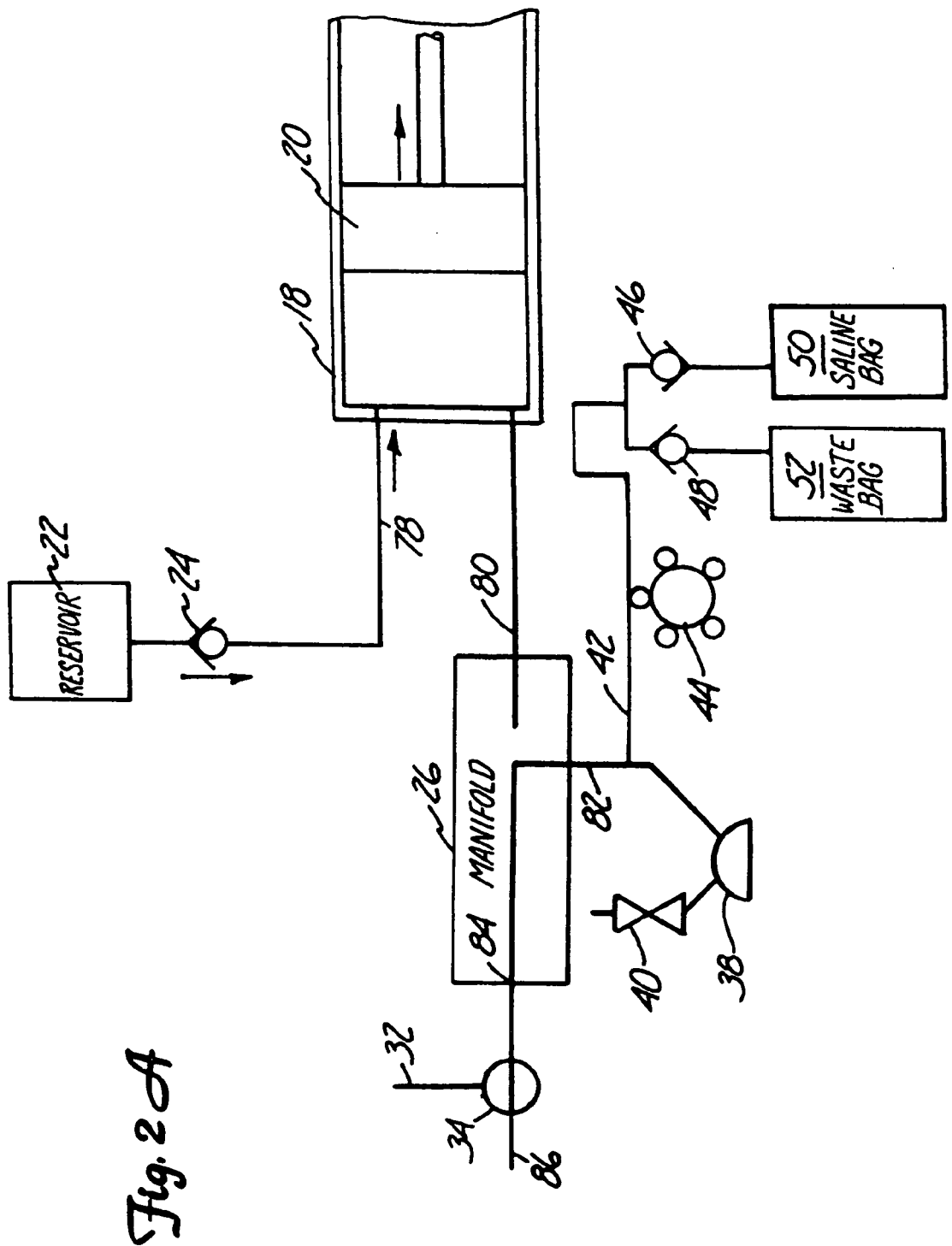
FIGS. 2A-2 are diagrams illustrating operations of the system of FIG. 1.

FIGS. 2A-2G are diagrams illustrating fluid flow paths during seven different operations of system 10. Those operational are contrast fill (FIG. 2A), air purge (FIG. 2B), patient inject (FIG. 2C), patient pressure (FIG. 2D), saline flush (FIG. 2E), aspirate waste (FIG. 2F), and medicate patient (FIG. 2G).

The contrast fill operation illustrated in FIG. 2A involves the filling of syringe body 18 with radiographic contrast material from reservoir (contrast media supply) 22. The contrast fill operation is performed during initial set up of system 10, and may be repeated during operation of system 10 whenever syringe body 18 is running low on radiographic contrast material.

Plunger 20 is retracted, which creates a vacuum within syringe body 18 which draws contrast material from reservoir 22 through check valve 24 into syringe body 18 through upper port 78.

The Contrast Fill operation typically will result in some air being drawn into or remaining within syringe body 18. It is important, of course, to prevent air from being injected into the patient through catheter 30. That is the purpose of the Air Purge operation shown in FIG. 2B. Also, the location of two ports at different elevations allows for a greater amount of safety in preventing air bubbles in the injection.

During the Air Purge operation, plunger 20 travels forward to expel trapped air within syringe body 18. The air, being lighter than the contrast material, gathers near the top of syringe body 18. As plunger 20 moves forward, the air is expelled from syringe body 18 through upper port 78 and one-way valve 24. In the embodiment illustrated in FIG. 2B, one-way valve 24 is a weighted one-way valve which allows flow of radiographic contrast material from reservoir 22 to upper port 78, but will not allow radiographic contrast material to flow in the opposite direction from upper port 78 to reservoir 22. Valve 24 will, however, allow air to flow from port 78 to reservoir 22. As soon as radiographic contrast material begins flowing out of syringe body 18 through upper port 78 to valve 24, valve 24 closes to prevent any further flow toward reservoir 22.

Valve 24 can also, in alternative embodiments, can be a solenoid actuated or motor driven valve operated under control of the electric circuitry within console 12. In either case, valve 24 is capable to withstanding the relatively high pressures to which it will be subjected during the inject operation. Preferably, valve 24 is capable of withstanding static fluid pressures up to about 1200 p.s.i.

FIG. 2C illustrates the Patient Inject operation. Plunger 20 travels forward under the interactive control of the user, who is controlling trigger 66 of remote control 14. The movement of Plunger 20 creates hydraulic pressure to force contrast material out of syringe body 18 through lower port 80 and through manifold 26 and high pressure tube 28 into catheter 30. As shown in FIG. 2C, syringe lower port 80 and patient port 84 are connected for fluid flow during the patient inject operation.

Figure 2B:
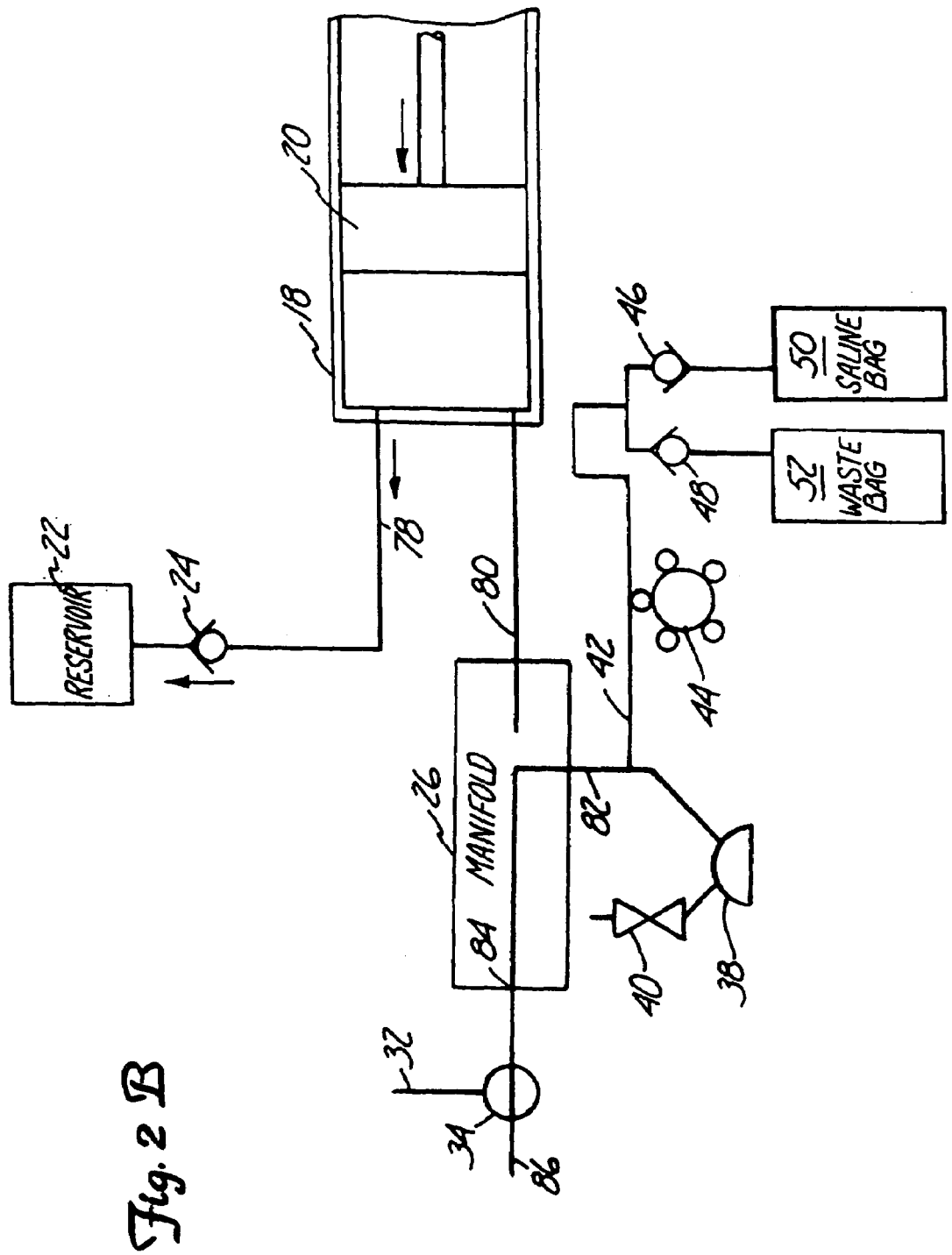

Manifold 26 contains a valve which controls the routing of fluid connections between patient port 84 and either syringe bottom port 80 or transducer/saline port 82. In one embodiment of the present invention, manifold 26 includes a spool valve which is spring biased so that patient port 84 is normally connected to transducer/saline port 82 (as illustrated in FIGS. 2A and 2B). When the pressure at syringe bottom port 80 builds with the movement of plunger 20 forward, the bias force against the spool valve is overcome so that syringe bottom port 80 is connected to patient port 84, and transducer/saline port 82 is disconnected the valve within manifold 26 protects pressure transducer 38 from being exposed to the high pressure generated by the patient inject operation.

The spool valve opens automatically during the patient inject operation in response to increase pressure exerted on it from the syringe lower port 80. The spool valve closes and returns to its original position allowing for connection of patient port 84 to transducer 38 when a slight vacuum is applied by retraction of plunger 20 at the end of each Patient Inject operation In an alternative embodiment, the valve within manifold 26 is an electromechanical or motor driven valve which is actuated at appropriate times to connect either syringe lower port 80 or transducer/saline port 82 to patient port 84. The actuator mechanism is controlled by console 12. Once again in this alternative embodiment, the valve protects pressure transducer 38 from being exposed to high pressure.

FIG. 2D illustrates the Patient Pressure operation. System 10 allows for reading of the patient's blood pressure, which is monitored through catheter 30. Patient blood pressure can be monitored through the use of pressure transducer 38 at any time except during the patient inject, saline flush, and waste aspirate operations. The pressure reading being produced by pressure transducer 38 may be normalized by manually opening stop-cock 40 and closing stop-cock 34 to expose pressure transducer 38 to atmospheric pressure.

During the Saline Flush operation illustrated in. FIG. 2E, saline solution is used to flush all of the internal lines, pressure transducer chamber 38, tube 28, and catheter 30. As shown in FIG. 2E, peristaltic pump 44 is operating in a direction which causes saline solution to be drawn from bag 50 through check valve 46 and through tubing 42 to saline port 82. Manifold 26 connects saline port 82 to patient port 84 so that saline solution is pumped out of patient port 84 and through tube 28 and catheter 30.

During the Aspirate Waste operation, patient port 84 is again connected to saline port 82. During this operation, peristaltic pump 44 is operating in the opposite direction from its rotation during the saline flush operation. As a result, patient fluids are aspirated from patient port 84 to saline port 82 and then through tubing 42 and check valve 48 into waste collection bag 52. Peristaltic pump 44 acts as a valve pinching/occluding tubing 42 and preventing back flow to/from saline and waste containers 50 and 52 in conjunction with check valves 46 and 48.

With catheter 30 in place within the patient, it may be desirable to supply patient medication. System 10 allows for that option by providing patient medication port 32. As shown in FIG. 2G, when stop-cock 34 is open, a medication source connected to port 32 will be connected to patient port 84, and thereby to catheter 30. During the medicate patient operation, peristaltic pump 44 and plunger 20 are not moving.

Figure 3A:
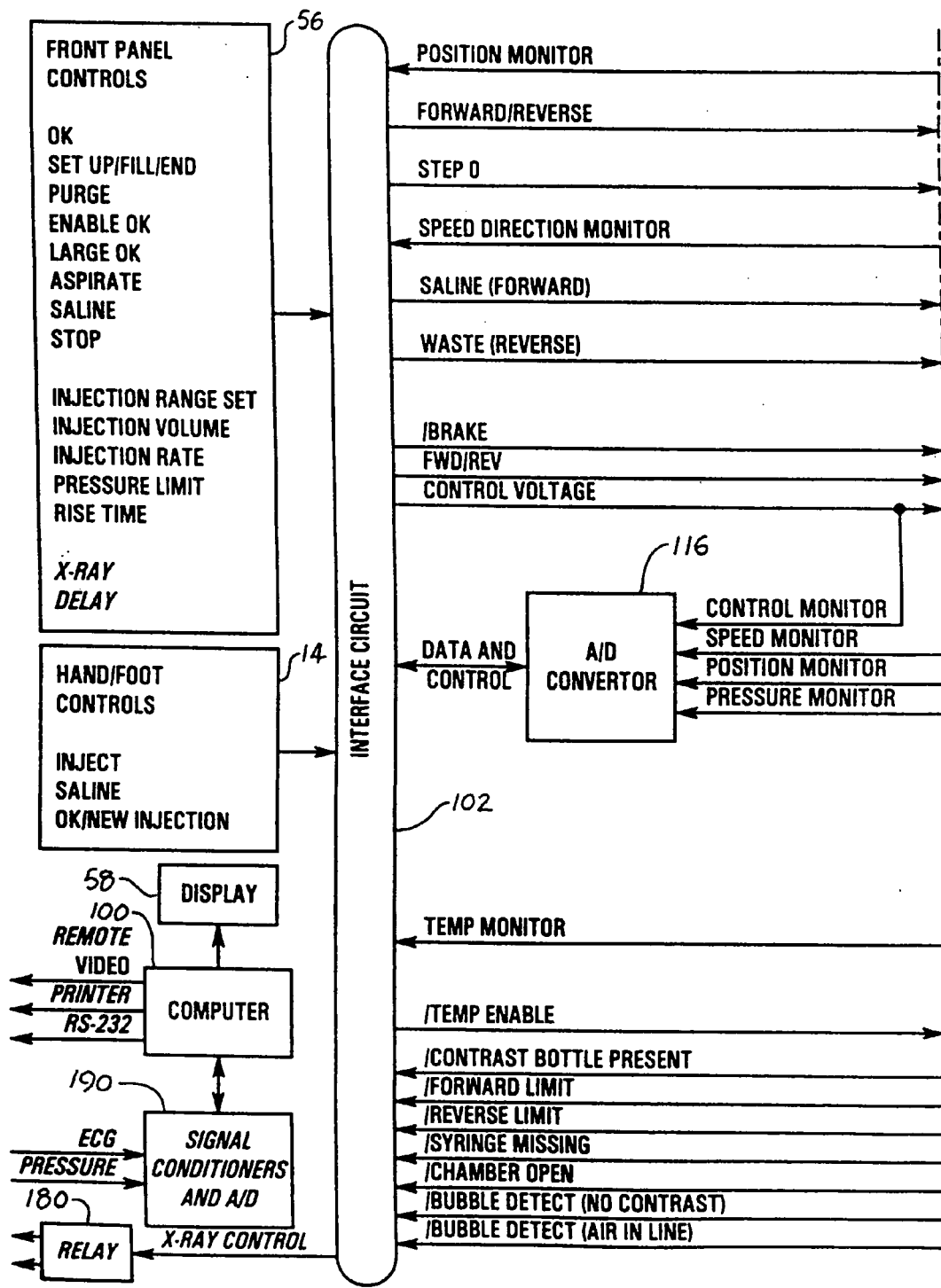
FIGS. 3A and 3B are electrical block diagrams of the control system of the injector system of FIG. 1.
Figure 3B:
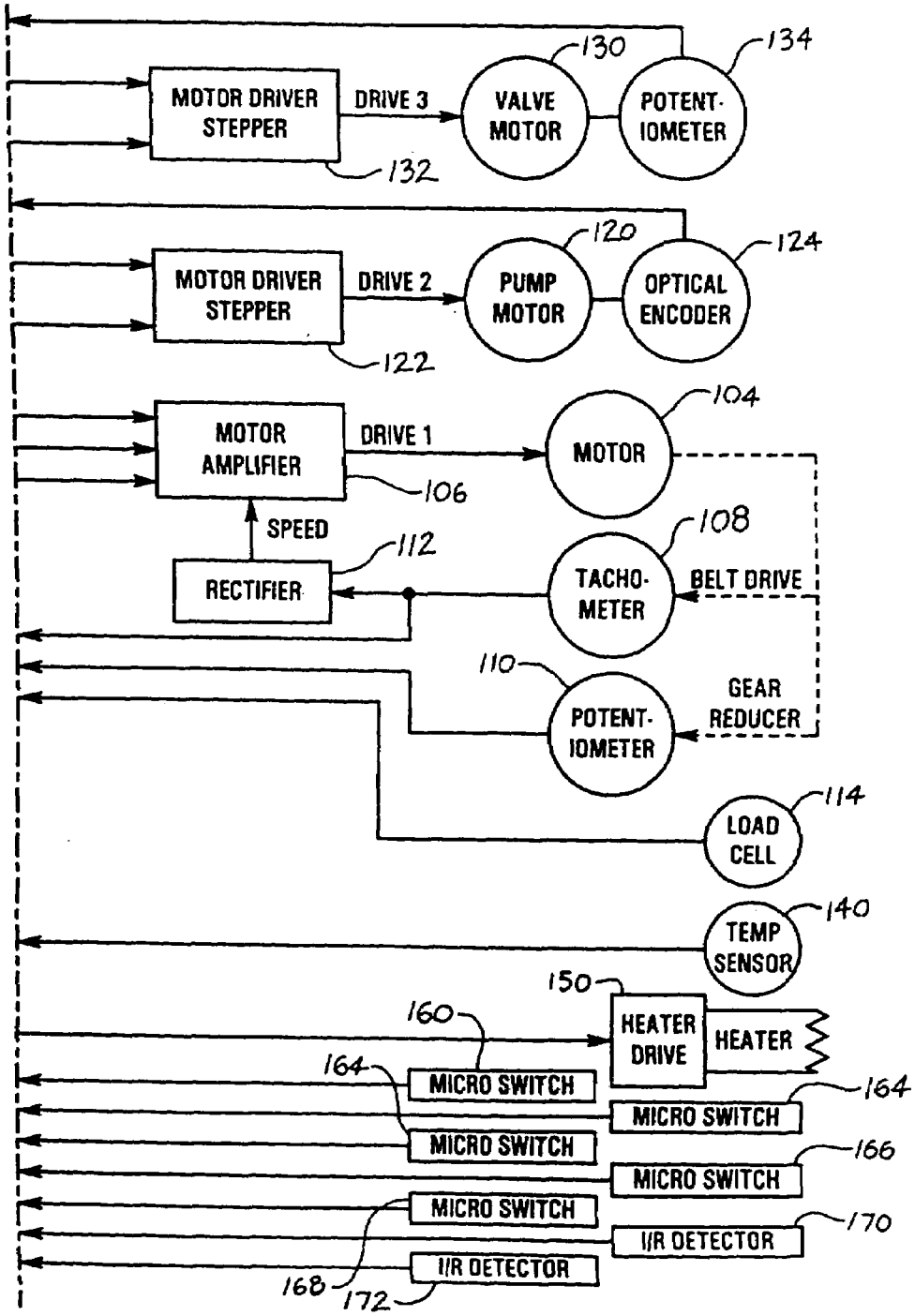

FIGS. 3A and 3B are electrical block diagrams of a control system that has been used with above-described angiographic injector system. The electrical control system of FIGS. 3A and 3B includes a single digital computer 100, which receives input signals from remote control 14 and front panel controls 56 through interface 102, and provides signals to display 58 to display operation data, alerts, status information and operator prompts. A subsequent preferred embodiment will describe an improved electrical control system; however the single computer system is being described herein to complete the functional description of an angiographic injector system that incorporates the components of the angiographic injector system 10 described above.

Computer 100 controls the motion of plunger 20 through a motor drive circuit which includes motor 104, motor amplifier 106, tachometer 108, potentiometer 110, a rectifier 112, pressure sensing load cell 114, and A/D converter 116.

Motor amplifier 106 provides a Drive 1 signal to motor 104 in response to Control Voltage, Fwd/Rev, and/Brake signals from computer 100 and a speed feedback signal from tachometer 108 through rectifier 112. The outputs of tachometer 108 and potentiometer 110 are supplied to computer 100 through A/D converter 116 as Speed Monitor and Position Monitor signals. These allow computer 100 to check motor speed, motor direction, and position (volume is a calculated value).

Pressure sensor 114 senses motor current or plunger force in order to measure the pressure being applied to the radiographic contrast material within syringe body 18. This Pressure Monitor Signal is supplied through A/D converter 116 and interface 102 to computer 100.

Peristaltic pump 44 is driven under the control of computer 100 through pump motor 120, motor driver 122 and optical encoder 124. Computer 100 provides Saline (Forward) and Waste (Reverse) drive signals to motor driver 122 to operate pump motor 120 in a forward direction for saline flush and a reverse direction for waste aspiration. Optical encoder 124 provides the Speed Direction Monitor signal to interface 102 which indicates both the speed and the direction of rotation of pump motor 120.

FIG. 3A and 3B illustrate an embodiment of the control system in which valve motor 130 is used to actuate valves such as one-way valve 24 and the valve within manifold 26. In this embodiment, computer 100 controls valve motor 130 through motor driver 132, and monitors position through a Position Monitor feedback signal from potentiometer 134. In this particular embodiment, valve motor 130 is a stepper motor.

Computer 100 monitors temperature of the contrast material based upon a Temp Monitor signal from temperature sensor 140. Temperature sensor 140 is preferably positioned near syringe body 18. If the temperature being sensed by temperature sensor 140 is too high, computer 100 will disable operation motor 104 to discontinue patient injection. If the temperature is too low, computer 100 provides a/Temp Enable drive signal to heater drive 150, which energizes heater 152. In one preferred embodiment, heater 152 is a resistive film heater which is positioned within syringe holder 116 adjacent to syringe body 18.

Computer 100 also receives feedback signals from contrast bottle sensor 160, forward limit sensor 162, reverse limit sensor 164, syringe missing sensor 166, chamber open sensor 168, no contrast bubble detector 170, and air in line bubble detector 172.

Contrast bottle sensor 160 is a miniature switch located within reservoir holder 72. The state of the Contrast Bottle Present signal from sensor 160 indicates whether a reservoir 22 is in position within holder 72. If reservoir 22 is not present, computer 100 will disable the fill operation.

Forward limit and reverse limit sensors 162 and 164 sense the end limit positions of plunger 20. When plunger 20 reaches its forward limit position, no further forward movement of plunger 20 is permitted. Similarly, when reverse limit sensor 164 indicates that plunger 20 has reached its reverse limit position, no further reverse movements are permitted.

Syringe missing sensor 166 is a miniature switch or infrared emitter/detector which indicates when syringe body 18 is not in position within syringe holder 16. If syringe body 18 is not in position, all movement functions are disabled except that plunger 20 can move to its reverse limit position (i.e., return to zero).

Chamber open sensor 168 is a miniature switch or infrared emitter/detector which senses when door 70 of syringe holder 16 is open. When the signal from sensor 168 indicates that door 70 is open, all movement functions are disabled. Only when door 70 is closed and locked may any movement be allowed. When door 70 is indicated as closed and sensor 166 indicates the syringe body 18 is in position, other normal functions of the system 10 can proceed.

Bubble detector 170 is positioned between reservoir 22 and top port 78, and is preferably an infrared emitter/detector which senses air bubbles. If an air bubble is sensed in the flow path between reservoir 22 and top port 78 during a fill operation, the fill operation is disabled until a new reservoir is connected.

Bubble detector 172 is positioned to sense air bubbles in high pressure line 28. It is preferably an infrared emitter/detector type of bubble detector. Any air bubble which is sensed in high pressure line 28 results in the disabling of all fluid push out functions, whether the fluid is saline solution from peristaltic pump 44 or contrast material from syringe body 18.

The control system of FIGS. 3A and 3B also includes the capability to provide a control signal to x-ray equipment through relay 180 which is controlled by computer 100. In addition, computer 100 receives data from blood pressure transducer 38 and from an electrocardiograph (ECG) system, which is separate from injector system 10. The Pressure and ECG signals are received through signal conditioners and A/D converter 190, and are transferred to computer 100. The ECG signal is used by computer 100 in one preferred embodiment, to synchronize operation of motor 104 (and thus the Patient Inject operation) with heart beats.

Blood flow to the heart occurs predominantly in diastole (when the heart is between contractions). Continuous injection of contrast material results in spillage of the contrast material into the aorta during systole (during contraction). By injecting primarily during diastole, contrast dosage can be reduced without impairing the completeness of the contrast injection into the coronary artery.

In a preferred embodiment, the injection of radiographic contrast material is synchronized to the coronary artery blood flow. The time periods of systole and diastole are determined using an electrocardiographic (ECG) electrical signal, arterial blood pressure waveform analysis, or other timing based on the heart rate. By controlling speed of motor 104, speed and therefore movement of plunger 20, the injection of contrast material is interrupted during the period of systole, which reduces or stops contrast injection during this time. In combination with remote control 14, the operator can vary the rate of contrast injection into the coronary artery while computer 100 automatically pulses the contrast injection to the cardiac cycle.

The inertial forces of the moving contrast material and expansion of the containers and tubing holding the contrast material and transmitting it to the patient can cause a phase lag between movement of plunger 20 within syringe body 18 and movement of contrast material out of catheter 30 into the patient. To adjust to the phase lag between the plunger 20 movement and contrast expulsion into the patient, a variable time offset can be entered through control panel 54 such that the timing of the cardiac cycle can be offset by a selected time. Since the magnitude of the phase lag may be dependent on the frequency of the heart rate, an algorithm within computer 100 continuously and automatically adjusts the magnitude of the time offset, based on the instantaneous heart rate during the injection of contrast material.

FIG. 4 shows one embodiment of control panel 54 which illustrates the front panel control switches 56 and display 58 of one embodiment of the present invention. Front panel control switches 56 include Set Up/Fill/End switch 200, Purge switch 202, Aspirate switch 204, Saline switch 206, Enable OK switch 208, Injection Volume Limit switches 210a and 210b, Injection Flow Rate Limit switches 212a and 212b, Injection Pressure Limit switches 214a and 214b, Rise Time switches 216,a and 216b OK switch 218, Injection Range Toggle switch 220, Large Injection OK switch 222, and Stop switch 224.

Set Up/Fill/End switch 200 is a momentary push button switch. When it is first activated, the user will be notified to place syringe 18 in syringe holder 16. When syringe 18 has been placed in syringe holder 16 (which is indicated to computer 100 by sensor 166), the user will be instructed to close and lock the chamber (i.e., to close door 70). Display 58 then indicates to the operator that contrast reservoir 22 should be connected. Once contrast reservoir 22 has been put in place, the operator is requested to depress OK switch 218, at which time plunger 20 will retract at a set rate (preferably corresponding to a flow rate of 10 ml per second) to the maximum syringe volume. If the real speed (as indicated by feedback to computer 100 from A/D converter 116) is greater than the set speed, system 10 will stop.

Once plunger 20 is at its rearward most position, motor 104 is actuated to move plunger 20 forward to purge all air bubbles. Pressure sensor 114 provides an indication of when one-way valve 24 is closed and pressure is beginning to build up within syringe body 18. Once the purge is completed, the total volume injected and the number of injections counter is reset.

The actuation of switch 200 also allows for Ml retraction and disengagement of plunger 20 from syringe body 18.

Purge switch 202 is a protected momentary push button switch. When activated, Purge switch 202 causes plunger 20 to move forward to expel air through top port 78. The forward movement of plunger 20 is limited and stopped when a predetermined pressure within syringe 18 is reached. This is sensed by pressure sensor 114. The purge operation which is initiated by Purge switch 202 will expel air within syringe 20. The user may also use Purge switch 202 to purge fluid through patient port 84 by depressing and holding Purge switch 202 continuously on.

Aspirate switch 204 is a momentary push button switch which causes computer 100 to activate pump motor 120 of peristaltic pump 44. Pump motor 120 is operated to aspirate catheter 30 at a set speed, with the aspirated fluid being collected in waste bag 52. All other motion functions are disengaged during aspiration. If the real speed of motor 120 is greater than a set speed, computer 100 will stop motor 120.

Saline switch 206 is an alternate action switch. Pump motor 120 is activated in response to Saline switch 206 being pushed on, and saline solution from bag 50 is introduced into manifold 26 and catheter 30 at a set speed. If Saline switch 206 is not pushed a second time to stop the flow of saline solution within 10 seconds, computer 100 automatically stops pump motor 120. If a time-out is reached, Saline switch 206 must be reset to its original state prior to initiating any further actions.

Enable OK switch 208 is a momentary push button switch. After the system has detected a disabling function at the end of an injection other than a limit, Enable OK switch 208 must be activated prior to activating OK switch 218 and initiating any further function.

Injection Volume Limit keys 210*a* and 210*b* are pushed to either increase or decrease the maximum injection volume that the system will inject during any one injection. Key 210*a* causes an increase in the maximum volume value, and key 210*b* causes a decrease. Once the maximum injection volume limit has been set, if the measured volume reaches the set value, computer 100 will stop motor 104 and will not restart until OK switch 218 has been depressed. If a large injection (i.e., greater than 10 ml) has been selected, OK switch 218 and Large Injection OK switch 220 must both be reset prior to initiating the large injection.

Injection Flow Rate Limit keys 212*a* and 212*b* allow the physician to select the maximum flow rate that the system can reach during any one injection. If the measured rate (which is determined by the feedback signals from tachometer 108 and potentiometer 110) reaches the set value, computer 100 will control motor 104 to limit the flow rate to the set value.

Injection Pressure Limit keys 214*a* and 214*b* allow the physician to select the maximum pressure that the system can reach during any one injection. If the measured pressure, as determined by pressure sensor 114, reaches the set value, computer 100 will control motor 104 to limit the pressure to the injection pressure limit. The injection rate will also be limited as a result.

Rise Time keys 216*a* and 216*b* allow the physician to select the rise time that the system will allow while changing flow rate during any one injection. Computer 100 controls motor 104 to limit the rise time to the set value.

In alternative embodiments, keys 210*a*-210*b*, 212*a*-212*b*, 214*a*-214*b*, and 216*a*-216*b* can be replaced by other devices for selecting numerical values. These include selector dials, numerical keypads, and touch screens.

OK switch 218 is a momentary push button switch which resets functions and hardware sensors. In response to OK switch 218 being activated, computer 100 controls display 58 to ask the operator to acknowledge that the correct function has been selected. Activation of OK switch 218 causes the status to be set to Ready.

Injection Range switch 220 is a toggle switch. Depending on whether switch 220 is in the "small" or "large" position, it selects either a high or a low injection volume range for the next injection.

Large Injection OK switch 222 is a momentary push button switch. When the large injection range has been selected by injection range switch 220, the Large Injection OK button 222 must be activated to enable OK switch 218. OK switch 218 must be activated prior to each injection. On large volume injections, the user is required to verify the volume selected by activating first Large Injection OK switch 222 and then OK switch 218.

Stop switch 224 is a momentary push button switch. When stop switch 224 is pushed, it disables all functions. Display 58 remains active.

Display panel 58 includes Set-Up display 250, Status display 252, Alerts display 254, Limits display 256, total number of injections display 260, total volume injection display 262, flow rate display 264, injection volume display 266, injection volume limit display 268, injection rate limit display 270, pressure limit display 272, rise time minimum display 274, large injection display 276, and real time clock display 278.

Set-Up display 250 contains a series of messages which are displayed as the operator goes through the set up procedure. The display of messages in set up display 250 are initiated by the actuation of set up switch 200 as described previously.

Status display 252 provides a flashing indication of one of several different operating conditions. In the embodiment shown in FIG. 4, these status conditions which can be displayed include "Ready", "Set-Up", "Injecting", "Filling", "Flushing", and "Aspirating".

Alerts display 254 and Limits display 256 notify the operator of conditions in which system 10 has encountered a critical control parameter and will disable operation, or has reached an upper or lower limit and will continue to function in a limited fashion, or has reached an upper or lower limit and will continue to operate.

Total number of injections display 260 displays the total number of injections (cumulative) given for the current patient case. The cumulative total volume injected during the current patient case is displayed by total volume display 262.

Displays 264 and 266 provide information on the current or last injection. Display 264 shows digital value of the real time flow rate to the patient during injection. Once the injection is completed, the value displayed on display 264 represents the peak flow rate reached during that injection. Display 266 shows the digital value of the volume injected during the most recent injection.

Display 268 displays the digital value of the maximum injection volume selected by operation of switches 210*a* and 210*b*. Similarly, display 270 shows the digital value of the maximum flow rate that the system will allow, as selected by switches 212*a* and 212*b*.

Display 272 shows the digital value of the maximum pressure that the system will allow to be developed in syringe 18. The pressure limit is selected by switches 214*a* and 214*b*.

Display 274 displays the minimum rise time that the system will allow while changing flow rate. The minimum rise time is selected through switches 216*a* and 216*b*.

Large injection display 276 provides a clear indication when the large injection scale has been selected by the operator.

Real-time clock display 278 shows the current time in hours, minutes, and seconds.

Figure 5A:
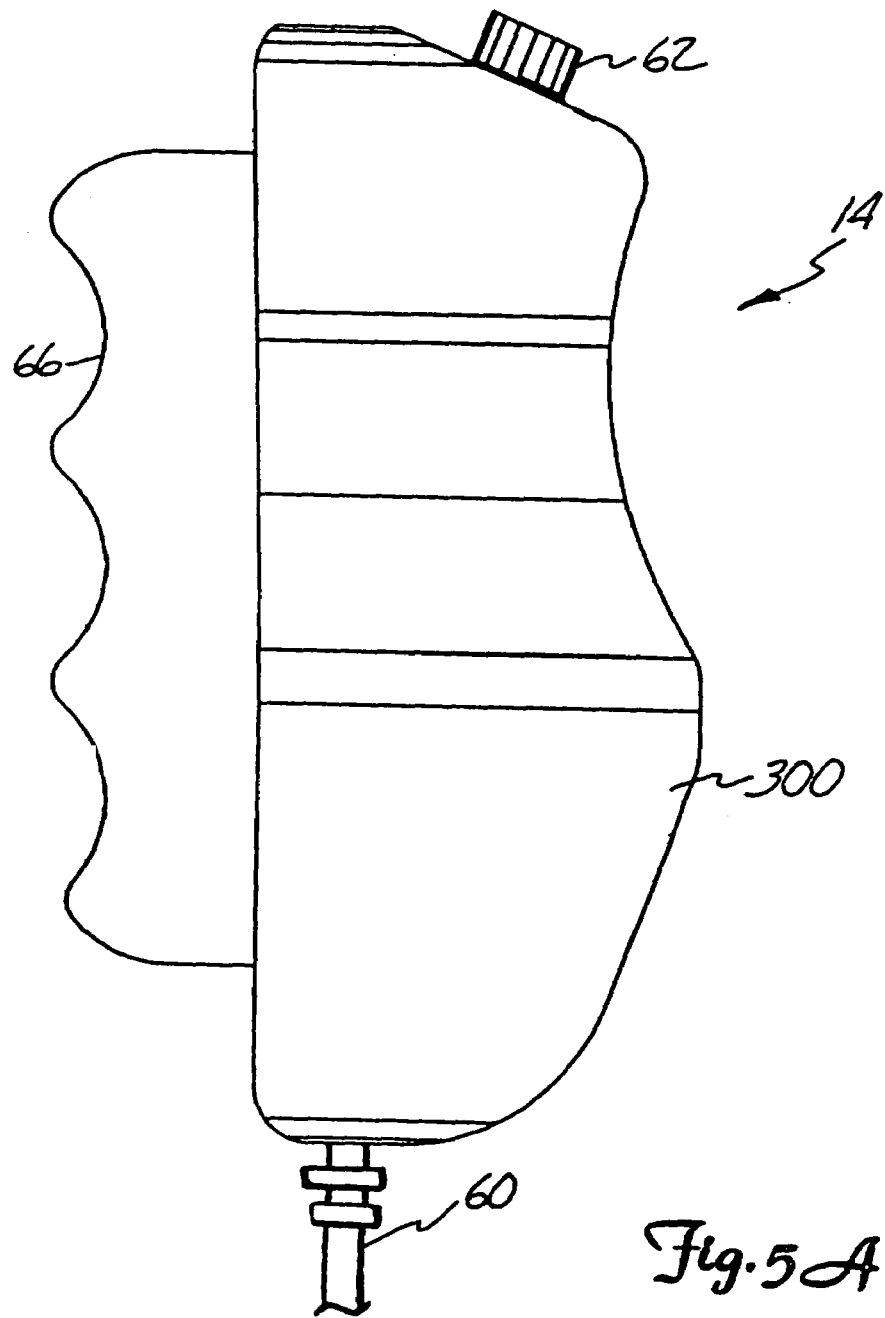
FIGS. 5A and 5B are side and partial top perspective views of the remote control of the system of FIG. 1.
Figure 5B:
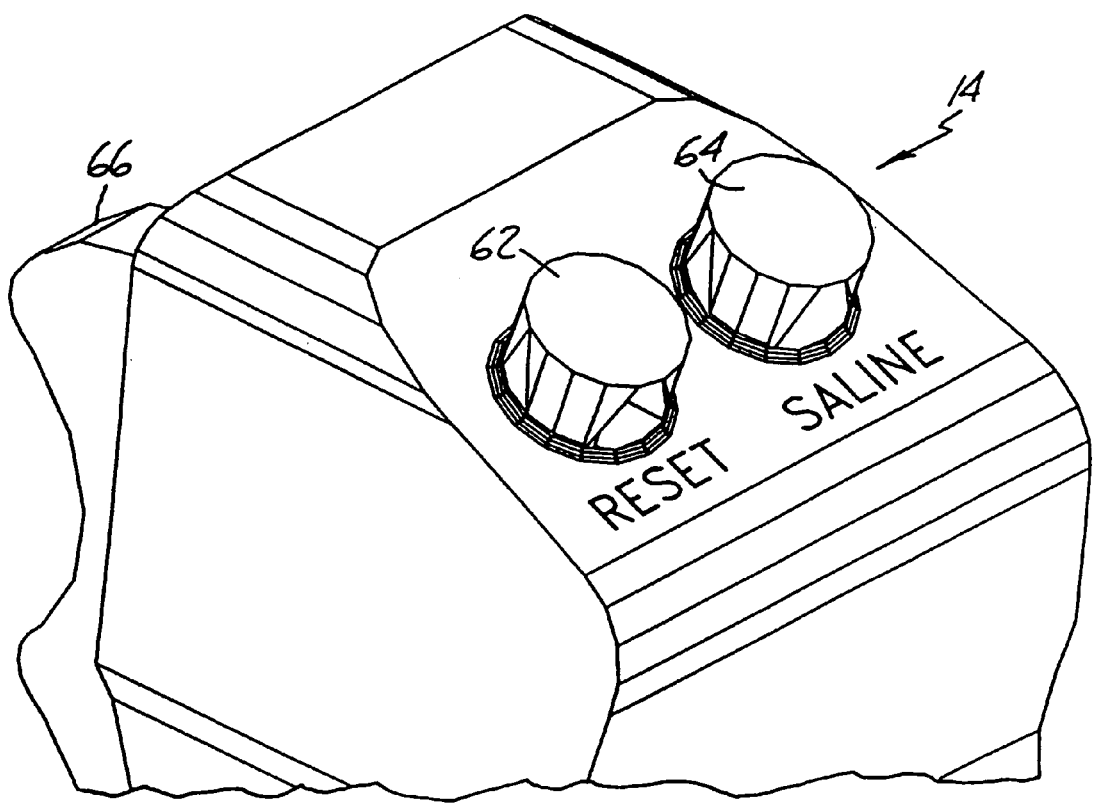
Figure 6:
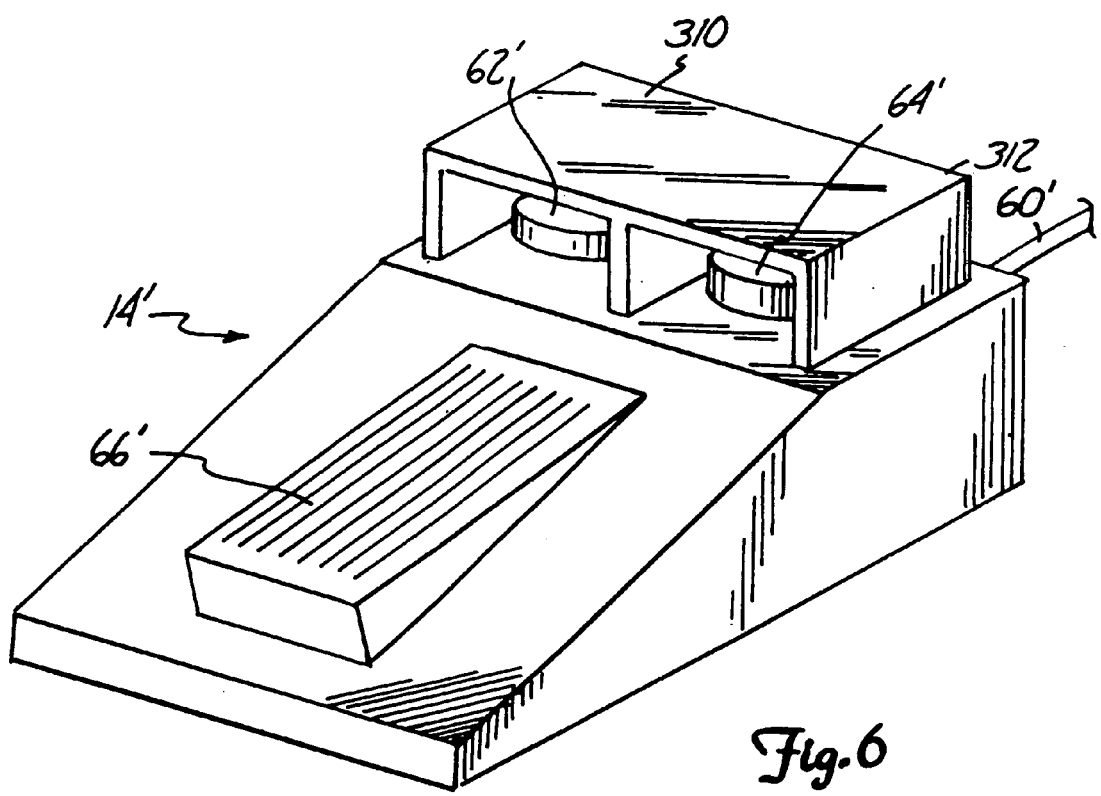
FIG. 6 is a perspective view of a foot operated remote control.

FIGS. 5A and 5B show one embodiment of a remote control 14 which includes main housing 300, which is designed to conform to the users hand. Trigger 66 is movable with respect to housing 300, and the position of trigger 66 generates a command signal which is a function of trigger position. In one embodiment, trigger 66 is linked to a potentiometer within housing 300. The command signal controls the injunction flow rate or speed. The flow rate is directly proportional to trigger position.

Reset switch 62 is a momentary push button switch whose function is identical to that of OK switch 218. Alternatively, Reset switch 62 may also be labeled "OK".

Saline switch 64 on remote control 14 is an alternate action push button switch which is pushed to turn on and pushed again to turn off. The function of Saline switch 62 is the same as that of Saline switch 206 on front panel 54.

As illustrated in another embodiment of the present invention, an alternative remote control 14' in the form of a foot pedal is used instead of the hand held remote control 14 illustrated in FIG. 1 and in FIGS. 5A and 5B. Foot pedal remote control 14' includes foot operated speed pedal or trigger 66' for providing a command signal, as well as Reset or OK switch 62' and Saline switch 64'. Covers 310 and 312 protect switches 62' and 64' so that they can only be actuated by hand and not accidentally by foot. Foot pedal remote control 14' is connected to console 12 by cable 60', but could alternatively be connected by a wireless link.

FIGS. 7A-7D and FIGS. 8A-8C illustrate the construction and operation of one way valve 24 and manifold 26 during Contrast Fill, Air Purge and Patient Injection operation.

FIGS. 7A and 8A illustrate one way or check valve 24, manifold 26, syringe body 18, and plunger 20 during a Contrast Fill operation. Inlet check valve of one way valve 24 includes weighted ball 350 which is positioned at its lower seated position within valve chamber 352 in FIGS. 7A and 7B. Contrast material is being drawn into syringe body 18 by the rearward movement of plunger 20. The contrast material flows through passages 354 around ball 350 and into upper port 78.

Manifold 26 contains spring loaded spool valve 360, which includes spool body 362, shaft 364, O-rings 366, 368 and 370, bias spring 372, and retainer 374. As shown in FIG. 7A, during the Contrast Fill operation, bias spring 372 urges spool body 362 to its right-most position toward syringe body 18. In this position, spool body 362 blocks lower port 80 of syringe body 18 while connecting transducer saline port 82 to patient port 84 through diagonal passage 376. O-rings 366 and 368 on the one hand, and O-ring 370 on the other hand, are positioned on the opposite sides of diagonal passage 376 to provide a fluid seal.

FIGS. 7B and 8B illustrate the Air Purge operation. Syringe body 18 has been filled with contrast fluid, but also contains trapped air. Plunger 20 is driven forward to force the air out of syringe body 18 through upper port 78 and through check valve 24. The force of the air may cause a slight lifting of ball 350 in check valve 20. Ball 350, however, is sufficiently heavy that the air being forced out of syringe body 18 and back toward reservoir 22 cannot lift ball 350 into its uppermost seated position where it would block the flow of air out of syringe body 18.

During the Air Purge operation, spool valve 360 is in the same position as in FIG. 7A. Diagonal passage 376 connects transducer saline port 82 with patient port 84. As a result pressure monitoring by pressure transducer 38 can be performed during the Air Purge (as well as the Contrast Fill) operation.

FIGS. 7C and 8C illustrate the state of manifold 26 and check valve 24 at the end of the Air Purge operation and at the beginning of a Patient Inject operation.

In FIG. 7C, all air has been expelled from syringe body 18. Ball 350 may float on the radiographic contrast material, so that when all air has been removed and the radiographic contrast material begins to flow out of syringe body 18 and through upper port 78 to valve chamber 352, ball 350 is moved upwards to its upper seated position. Ball 350 blocks any continued upward flow of radiographic contrast material, as is illustrated in FIGS. 7C and 8C.

In the state which is illustrated in FIG. 7C, the pressure within syringe body 18, and specifically the pressure in lower port 80 has not yet reached a level at which the bias force of spring 372 has been overcome. As a result, spool body 362 has not yet moved to the left and diagonal passage 376 continues to connect transducer saline port 82 with patient port 84.

Figure 7D:
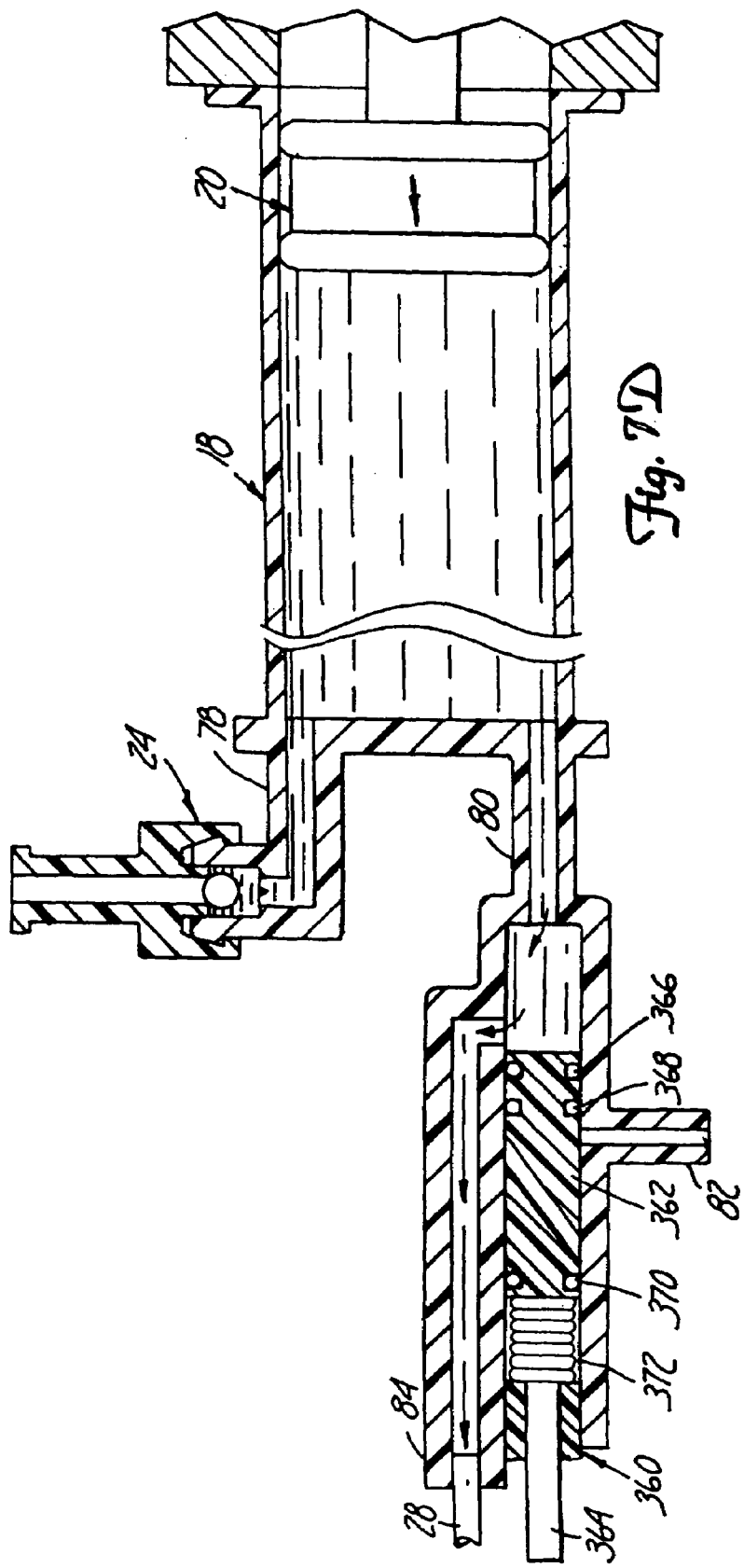

FIG. 7D illustrates the patient inject operation. Plunger 20 is moving forward, and inlet check valve 24 is closed. The pressure at lower port 80 has become sufficiently high to overcome the bias force of spring 372. Spool body 362 has been driven to the left so that lower port 80 is connected to patient port 84. At the same time spool body 362 blocks transducer/saline port 82.

By virtue of the operation of spool valve 360, the high pressure generated by movement of plunger 20 and syringe body 18 is directly connected to patient port 84, while saline port 82 and pressure transducer 38 are protected from the high pressure. The pressure to actuate may be variable and determined after manufacture by increasing or decreasing the syringe preload.

Those skilled in the art will appreciated that other configurations of the general angiographic injector system 10 can be configured. For example, the alternative syringe and mounting system portions of the referenced angiographic injector system described in copending U.S. patent application Ser. No. 08/957,228, entitled "Dual Port Syringe" filed on Oct. 24, 1997 could be employed to replace and/or modify those previously described. Further, those skilled in the art will recognize other improvements such as to the manifold portion of the assembly, as for example described in copending parent U.S. patent application Ser. No. 08/957, 801, entitled "Angiographic Injector System with Automatic High/Low Pressure Switching" filed on Oct. 24, 1997 could be employed, as well as other configurations of the remote control 14. Several alternative configurations of the remote control assembly are described in this referenced application and in copending U.S. applications Ser. No. 08/965,583, entitled "Pneumatic Controller and Method" filed on Nov. 6, 1997 and Ser. No. 29/079,023, entitled "Hand-Held Pneumatic Control Device" filed on Nov. 6, 1997, all of which are herein incorporated by reference.

Figure 9A:
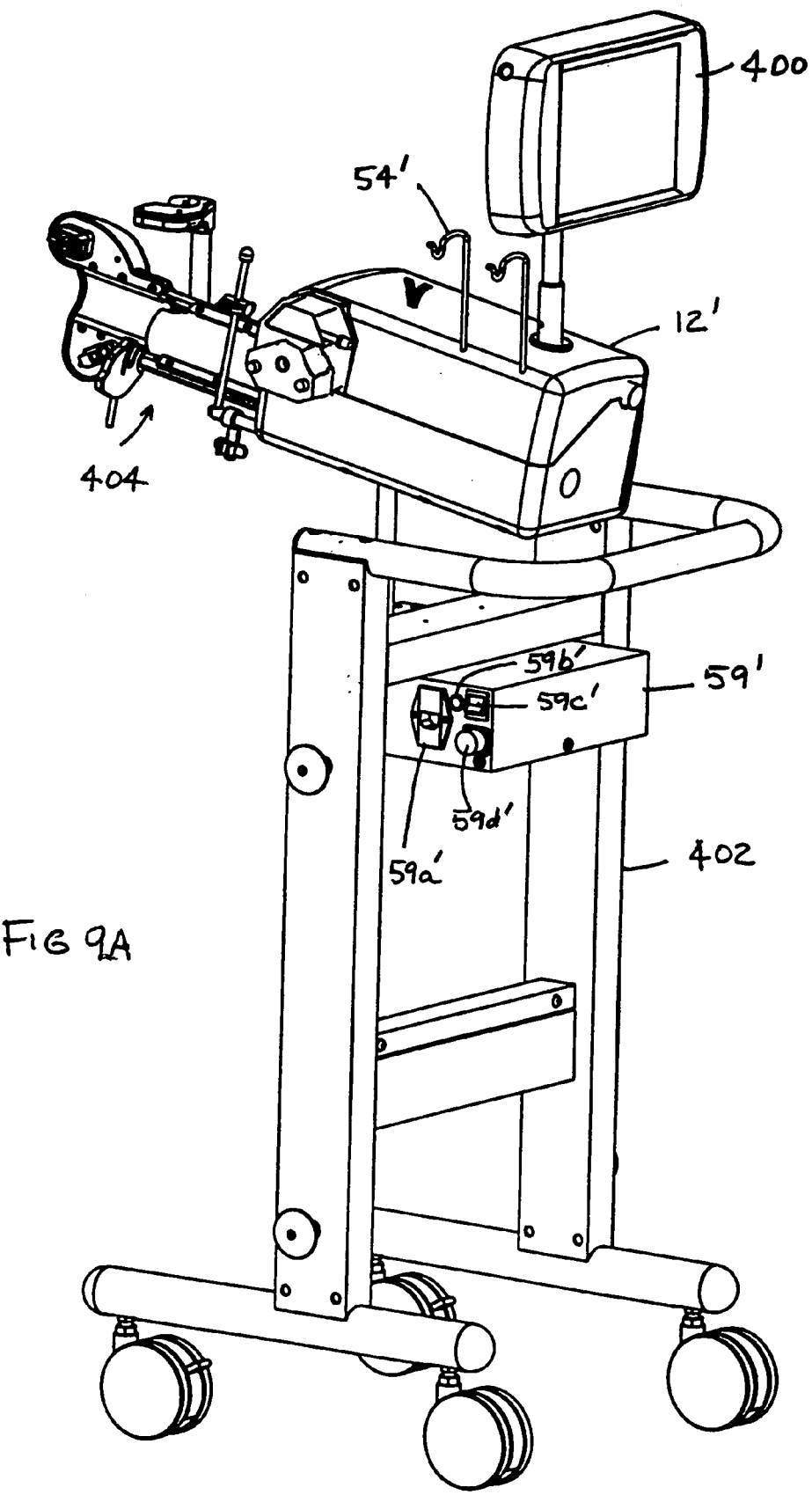

An alternative embodiment configuration of the angiographic injector system of the preceding figures is generally indicated at 10' in FIGS. 9a and 9b. In the embodiment illustrated in FIG. 9, the physical locations of some of the components of the angiographic injector system 10 have been rearranged for facilitating use of the system. For example, the user interface 54, the control switches 56 and the display 58 of the first described embodiment have been consolidated into a single control panel 400. In the second embodiment illustrated, the control panel 400 mounts to the console or injector head 12' on a swivel base that may be disconnected and reconnected by the user for optimal placement. A mechanical diagrammatic chart of the FIG. 9 configuration is illustrated in FIG. 10. Referring to FIGS. 9 and 10, the Power supply 59' circuits are illustrated as being mechanically mounted separate from the console 12'. The console and power supply are mounted to a cart, generally indicated at 402 which includes wheels for easy movement and which is preferably designed to provide stability and deter tipping when used in its intended method. The cart enables the console and power supply assemblies to be rapidly attached and detached for allowing docking of the console and power supply to a bed or other stationary device equipped with a mating connection device. Referring to FIG. 10, the hand controller 14' is illustrated as being operatively connected to the control panel 400, and the peristaltic pump assembly 44' is indicated as being mechanically mounted to the console 12'. The assembly for holding the syringe and related components that have been previously described with regard to the first embodiment of the invention are generally indicated by the functional block entitled "mounting chamber" 404. Those components previously described and referred to as "disposable" items (i.e.: the syringe, the piston within the syringe body, the contrast valve, the patient manifold, the contrast spike and the patient blood pressure port) are generally designated by the functional block 406.

Figure 11A:
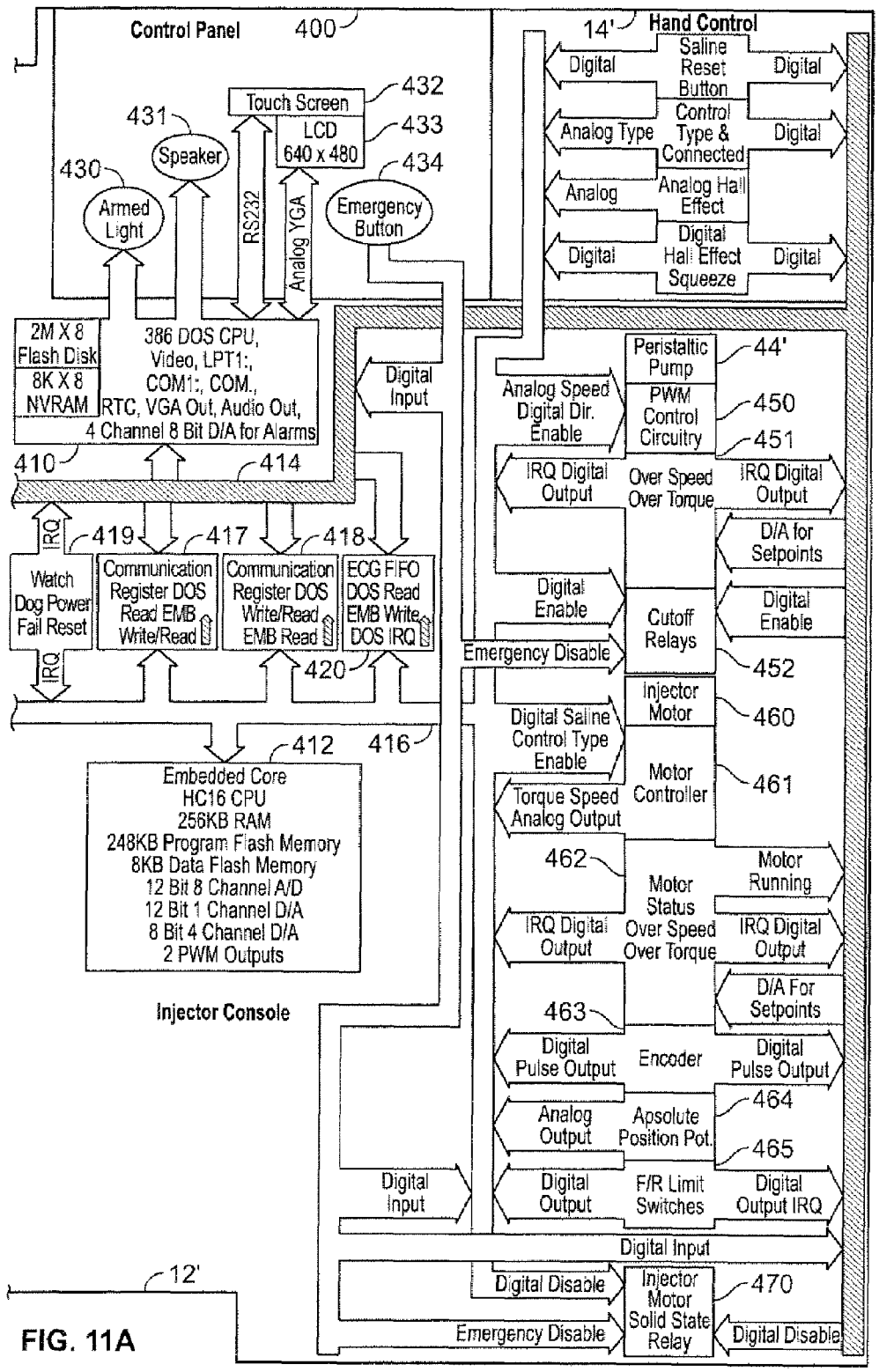
FIGS. 11A and 11B are an electrical block diagram of the control system and electrical functions of the system of FIGS. 9 and 10.
Figure 11B:
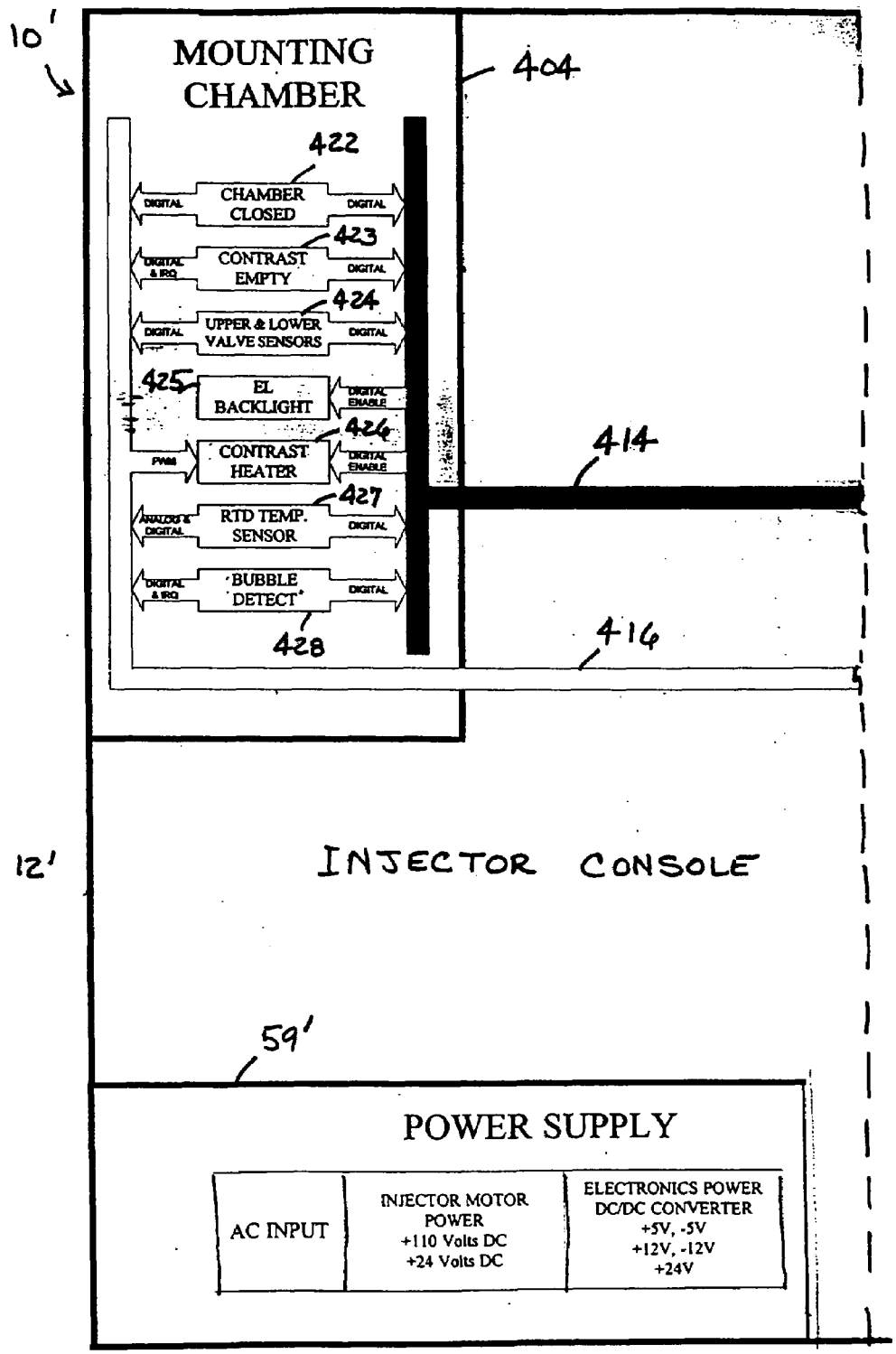

An electrical functional block diagram of a second preferred control configuration for the angiographic injector system 10' is illustrated in FIG. 11. The multiple figures (FIG. 11a and FIG. 11b) collectively comprise the electrical control network of the angiographic injector system 10'. For ease of description of the FIG. 11 network, numbers previously used for comparable electrical components of the first embodiment will not necessarily be duplicated in the description of similarly functioning electrical components of FIG. 11. Referring to FIG. 11, the control system includes two separate computer systems, each having intelligence for monitoring and controlling functions of the injector system. As with the prior embodiment, the computer system generally receives input signals from the control panel 400 and provides signals to display data, alerts, status information and operator prompts. In the preferred embodiment, the computer system comprises two micro-computers. A PC processor, generally indicated at 410 acts as the master processor of the control system, and an embedded processor, generally indicated at 412, acts as the slave processor. In general, the master processor instructs the embedded processor to perform commands, but both processors monitor the actions taken. Both processors serve as independent monitors of action, for safety. Key functions such as the injector motor movement and peristaltic motor movement are monitored by both micro-computers. In the preferred embodiment, the PC processor 410 has a 386 DOS central processing unit, and the embedded core processor 412 has an HC16 bit central processing unit. It will be appreciated that other types of microprocessors can be used within the spirit and intent of this invention.

Referring to FIG. 11, it will be noted that PC processor 410 communicates with electrical components throughout the system by means of a first communication bus 414, and the embedded core processor 412 communicates with electrical circuits throughout the system by means of a second communication bus 416. The two processors communicate with one another by means of their respective buses and a pair of communication registers generally indicated at 417 and 418. General "watch dog/power fail/reset" functions are indicated by the functional block 419, and ECG acquired information can be collected on a first-in first-out basis by the functional block 420 for processing by both microprocessors. In general, the type of communication between the various electrical functional blocks of the system and the two buses 414 and 416 as indicated by the individual signal flow paths of FIG. 11 which are associated with the respective electrical functional blocks and by the signal flow notations within those signal flow paths.

Referring to FIG. 11, the various electrical and sensing functions associated with the mounting chamber 404 include: a sensor entitled "chamber closed" (422) that indicates when the front loading chamber door used to load the disposable syringe into the mounting chamber is closed; a contrast bottle sensor indicated by "contrast empty" (423) which is located within the bottle holder and indicates whether fluid is present in the bottle; two valve sensors, indicated as "upper & lower valve sensors" (424) that are used by the computer to determine the state of the patient manifold valve and contrast valve; an electroluminescent back light, indicated by "EL backlight" (425) which facilitates manual bubble detection within the syringe and disposable items; a heating element, indicated by "contrast heater" (426) located inside the syringe holder adjacent to the syringe body; a pair of temperature sensors, indicated by "RTD Temp Sensor" (427) positioned near the syringe body for providing signals to control the contrast heater for maintaining the contrast material at a relatively constant temperature; and an air column detection sensor, indicated by "bubble detect" (428) positioned to sense air in the high pressure line which monitors fluid that is pumped to the patient for any bubbles or air columns. As indicated in FIG. 11, except for the EL backlight 425, each of the sensors in the mounting chamber communicate with both of the processors.

In general, the control panel 400 includes an arm light 430, a speaker 431, a touch screen 432, a display 433, and an emergency switch 434. The arm light 430 is lit when the injector is ready to perform an injection. The speaker 431 is an optional feature which can provide audible interface communication with the user. The display 433 is in the preferred embodiment a liquid crystal (LCD) panel which is used to display the operational state of the system. The touch screen 432 is overlayed on the LCD panel and is used by the user to control the system, as will be described in more detail hereinafter. All of the functions of the control panel communicate directly with the PC processor 410. The emergency switch 434 communicates directly with both of the communication buses 414 and 416 as well as with cutoff relays and the injector motor solid state relay hereinafter described.

The hand control functional block 14' includes the circuit functions of the remote hand control unit. As previously described, the hand controller is a device used to control the angiographic injector pump in a manner such that when actuated by a user, outputs an electrical signal which is proportional to the displacement of the hand controlled device. The controller is a passive electromechanical device that communicates with both of the microprocessors as indicated in FIG. 11. The hand controller contains a pair of sealed on-contact sensors that can remotely determine position of an object and which are used to determine the active travel distance and placement of the hand movable portion of the controller. The sensors are indicated by the two functional blocks indicated as "analog Hall effect" (440) and "digital Hall effect squeeze" (441). The saline reset function is indicated by "saline reset button" (442), and the functional block indicated as "control type and connected" (443) provides for a setting indication through the hand controller to the microprocessors as to whether the system is being used to perform a "fixed rate" or "variable rate" injection. Under the variable rate mode of operation, the operator is allowed to vary the instantaneous injection rate by means of the hand controller up to a predetermined maximum flow rate. In the fixed mode of operation, when the operator squeezes the hand controller actuator, the control system will respond by simply injecting the contrast material at the predetermined fixed rate that has been entered into the control system prior to the injection procedure.

The peristaltic pump 44' is driven under the control of the microprocessors through a pump motor and motor driver. The motor driver, generally indicated by the "PWM control circuitry" (450) provides a pulse width modulated control signal to the peristaltic pump motor. The computer provides both forward (Saline) and reverse (Waste) drive signals to the motor driver to operate the pump motor in a forward direction for a saline flush and in a reverse direction for waste aspiration. The peristaltic pump of the preferred embodiment includes an "overspeed overtorque" sensor 451 and "cutoff relays" 452. The overspeed/overtorque sensors 451 provide feedback signals to the microprocessors for accurately controlling the speed of the peristaltic pump by way of the pump drive circuits 450. The cutoff relays 452 can be activated by either of the microprocessors or by the emergency stop switch 434.

The injector motor 460 is operatively connected to move the piston or wiper within the syringe and is controlled by a "motor controller" amplifier (461). In the preferred embodiment, the motor driver 461 is an off-the-shelf servo amplifier which can be accurately controlled by means of a nested loop control configuration, hereinafter described. In general, the motor amplifier provides a drive signal to the motor in response to a control voltage. Forward, reverse and break signals come from the computer, and a speed feedback signal from an optical encoder is used to control the speed. Monitoring of the motor status is generally indicated by the functional block entitled "motor status overspeed/overtorque" (462) and an independent optical encoder sensor for sensing the motor speed and position, indicated by the "encoder" functional block (463). A potentiometer is used to provide a back-up signal to the embedded microprocessor indicating the absolute "position" of the motor. The potentiometer is indicated in the block diagram as the "absolute position pot." functional block (464). The outputs of the optical encoder and potentiometer are supplied to the processors as speed monitor and position monitor signals and allow the computers to check motor speed, motor direction and position. A pair of forward and reverse limit sensors sense the end limit positions of the syringe piston and are indicated by the functional block entitled "F/R limit switches" (465). When the piston reaches its forward limit position, no further forward movement is permitted. Similarly, when the reverse limit sensor indicates that the piston has reached its reverse limit position, no further reverse movements are permitted. The injector motor control also includes a solid state relay (470) for disabling the injector motor under command from either of the processors or the emergency switch 434.

The power supply 59' provides all electrical power to the system and includes an externally selectable voltage range switch 59a' enabling selection of connection of the power supply to either 110-120 volts AC or 220-240 volts AC. In the preferred embodiment, the line voltage operating frequency must be between 47 and 63 Hz, and the line voltage must be capable of carrying ten amps of current. The power supply further includes a power indicator light 59b' an on/off switch 59c' and a cable connector 59d' providing a connector for a cable leading to the circuits within the chassis 12'.

Figure 12:
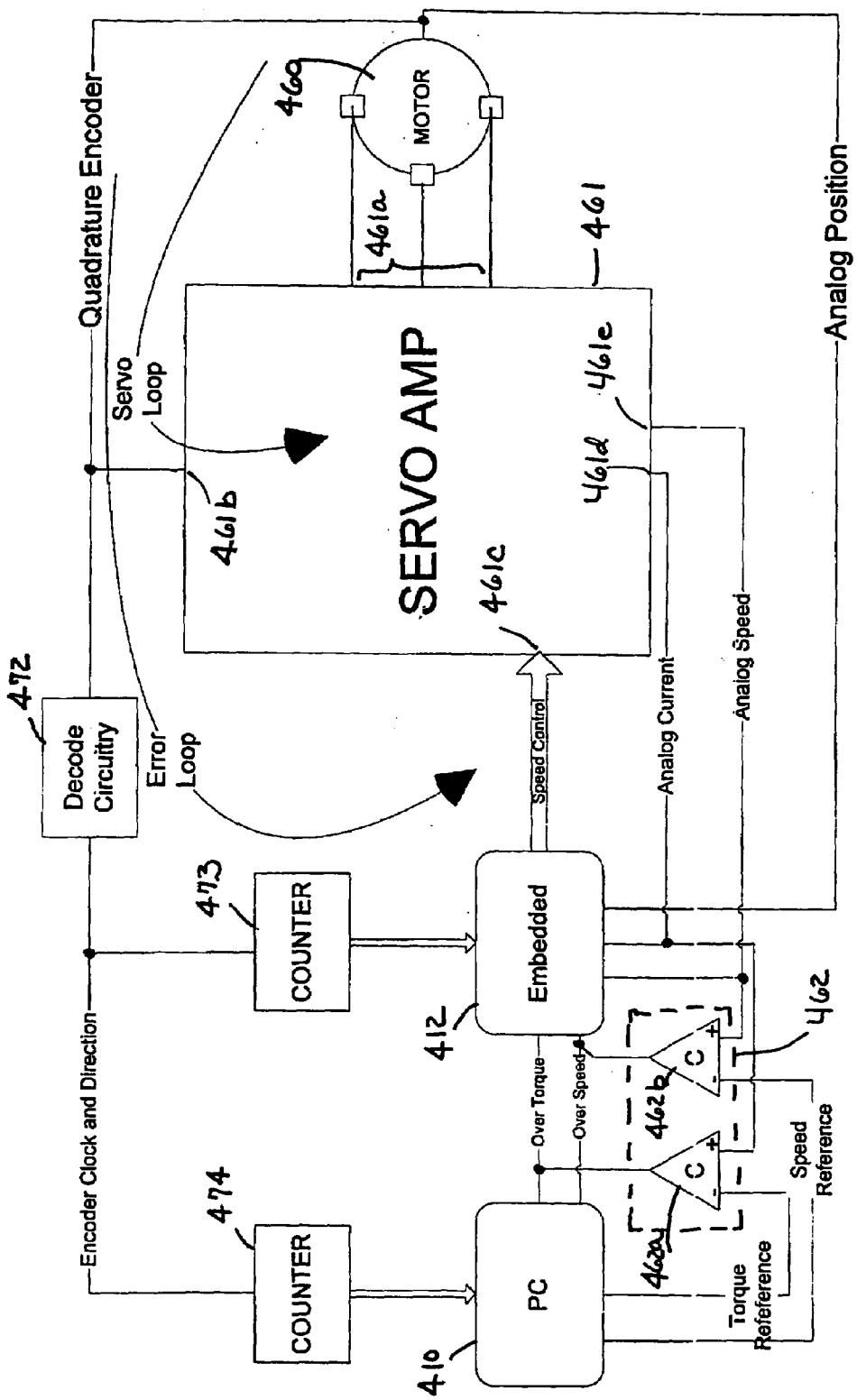
FIG. 12 is an electrical block diagram of the injector motor control portion of the control system of FIG. 11.

A more detailed electrical functional block circuit network for a preferred nested control loop configuration for control of the injector motor 460 is illustrated in FIG. 12. Referring thereto, the injector motor 460 is in the preferred embodiment, a brushless DC motor controlled by the servo amplifier network circuit 461. In the preferred embodiment, the servo amplifier network 461 is a BE30A Series PWM Brushless Servo Amplifier model BE25A20 designated to drive a brushless DC motor at a high switching frequency. In the preferred embodiment, the servo amplifier uses a quadrature encoder feedback input signal for velocity control. The servo amplifier has an output drive port generally indicated at 461a, a feedback signal input port 461b, a speed control signal input port 461c and a pair of analog output signal ports 461d and 461e respectively. The output port 461d carries a voltage signal developed within the servo amplifier that is proportional to the pressure or torque of the motor 460, and provides a signal to an output feedback line referred to as the "Analog Current" line. The output port 461e carries a voltage signal developed within the servo amplifier that is proportional to the speed of the motor 460, and provides a signal to the line indicated as "Analog Speed". An optical quadrature encoder (not illustrated in FIG. 12) is operatively connected to the output drive of the injector motor 460 (and indicated at 463 in FIG. 11), provides a pulse train feedback signal back to the feedback input port 461b of the servo amplifier 461 to provide accurate speed control of the motor 460 through the servo amplifier 461. This loop is referred to as the first loop or the "Servo Loop" in the figure. In the preferred embodiment, the servo amplifier 461 is an off-the-shelf amplifier that provides very accurate control of the speed of the injector motor 460 through this standard Servo Loop configuration and requires little further control. The quadrature encoder signal is also fed back through a signal conditioning Decode Circuit indicated at 472 to a pair of counters 473 and 474 which respectively provide cumulative count signals to the embedded processor 412 and the PC processor 410 respectively. The Analog Current and Analog Speed signals from the output ports 461d and 461e respectively of the servo amplifier 461 are directly fed as input signals to the embedded processor 412 and are respectively applied to first signal inputs of comparators 462a and 462b of the "motor status overspeed overtorque" functional block 462. The reference signal inputs for the comparators 462a and 462b are connected to receive input signals from the PC processor 410 corresponding to "torque reference" and "speed reference" input signals.

The comparators 462a and 462b respectively compare the feedback signals received from the servo amplifier 461 with the reference voltage signals received from the PC processor 410 and provide signal outputs representing "overtorque" and "overspeed" respectively to both the embedded processor 412 and the PC processor 410, as indicated in FIG. 12.

During an injection procedure, the master PC processor 410 instructs the embedded processor 412 to perform the injection. As part of this command, the embedded processor is told by the PC processor what the desired flow rate and maximum pressure allowed conditions are. Immediately prior to the PC processor issuing the injection command, it sets reference voltage values in the two comparators 462a and 462b, one being representative of the maximum flow rate the embedded processor is allowed to achieve and the other representing the maximum allowable pressure. During the injection, the "Analog Current" and the "Analog Speed" feedback signals from the servo amplifier 461 are fed back to the comparators 462a and 462b. If either of these feedback signal voltages exceed the respective reference voltages of the comparators, an appropriate output signal is provided by the triggered comparator, back to both of the processors. If either processor receives one or both signals from the comparators, that processor will cut power to the injector motor 460, immediately stopping the injection.

During an injection, the embedded processor 412 uses the digital encoder 463 to determine the current position of the ram or syringe piston. In the preferred embodiment, for each millimeter of contrast material injected 1,317 counts are received from the encoder 463. As the piston moves during an injection, the embedded processor looks at the current position of the ram or piston every ten milliseconds. The embedded processor then calculates the theoretical position of the ram based on a simple trapezoidal type move. If the current position is more than a predetermined number of millimeters different than the actual position, the injection is stopped and error is reported.

The potentiometer 464 which provides the "Analog Position" signal is used in a similar fashion, however its tolerance is higher. During ram or piston movement diagnostics the system calculates a constant that is representative of the number of ohms per millimeter of movement. During the injection, the embedded processor uses the same theoretical trapezoidal move to determine the theoretical position of the piston. As with the digital encoder process, if the current position of the ram is more than a predetermined number of ohms different than the actual analog position reading, the injection is stopped and an error is reported.

Accordingly, a nested loop control network is established wherein the primary direct Servo feedback loop control of the motor 460 is supplemented by the "Error Loop" control provided through the encoder signal which is fed back through the decoder circuitry 472 and counter 473 and embedded processor 412 back to the signal input terminal 461*c* of the servo amplifier 461. The first or "servo loop" is a standard velocity control loop that uses proportional integration; whereas the outer "error loop" is a position control loop which simply periodically checks on the servo loop control to ensure that the servo loop is accurately controlling the motor speed. The potentiometer which is operatively connected to the gear train output of the motor 460 is an absolute position sensor that simply acts as a back-up to the encoder loop. Similarly, the encoder feedback to the PC processor 410 through counter 474 acts as a redundant back-up to the primary error loop control through embedded processor 412, should the processor 412 fail to operate in its intended manner in providing speed correction signals through the secondary "error loop".

As briefly described above, the availability of multiple processors provides the capability of true multi-redundancey sensing using intelligence in both sensing circuits. In addition, the dual or multiple processor feature provides the capability for redundant control and monitoring safety features of key functions of the system such as injection motor movement and peristaltic motor movement. Both of these conditions are actively monitored by both microprocessors as described above, and as indicated in FIGS. 11 and 12. For example, an "overspeed safety circuit" for the injection motor is provided by the quadrature encoder 463 feeding signals through the decode circuitry 472 and the pair of counters 473 and 474 to the two processors. The use of two independent processors for receiving the encoder information acts as a safety circuit for sensing the flow rate, since both the embedded and PC processors count pulses to determine the injection flow rate. As stated above, the individual counts are accumulated over a specified time interval and the average speed is computed. The safety feature is provided by the fact that either processor may independently shut down the injector motor based on its own decision making capability, in the event of an overspeed condition. Such redundant sensing path dual processor control allows for safety monitoring in the event of a single component failure.

Similarly, an "over volume safety circuit" is provided by the same hardware used to provide the overspeed safety circuit. The pulses provided through counters 473 and 474 from the encoder to the embedded and PC processors allow both processors to independently count pulses to determine injection volume. Either processor may independent shut down the injector motor in the event of an overvolume condition.

A further dual safety feature, which does not require multiple processors, is provided by the "analog position" signal received from the potentiometer 464 which allows the embedded processor to check the volume by reading the change in the analog voltage output from the potentiometer. By providing the potentiometer as a back-up for the quadrature encoder, further dual redundancy safety is provided for sensing the injection volume.

Dual redundant motor safety circuits are provided as previously described for the injector motor "over current" and "overspeed" conditions. These circuits were previously described with respect to comparators 462*a* and 462*b*. The comparator 462*a* uses the "analog current" feedback signal from the servo amplifier 461 to provide dual input signals to both the embedded and PC processors to provide dual processor current measurement safety circuit sensing. Similarly, comparator 462*b* applies dual input signals to both of the processors as the result of the "analog speed" signal from the servo amplifier 461 to provide dual redundant sensing of the injector motor speed.

Figure 13:
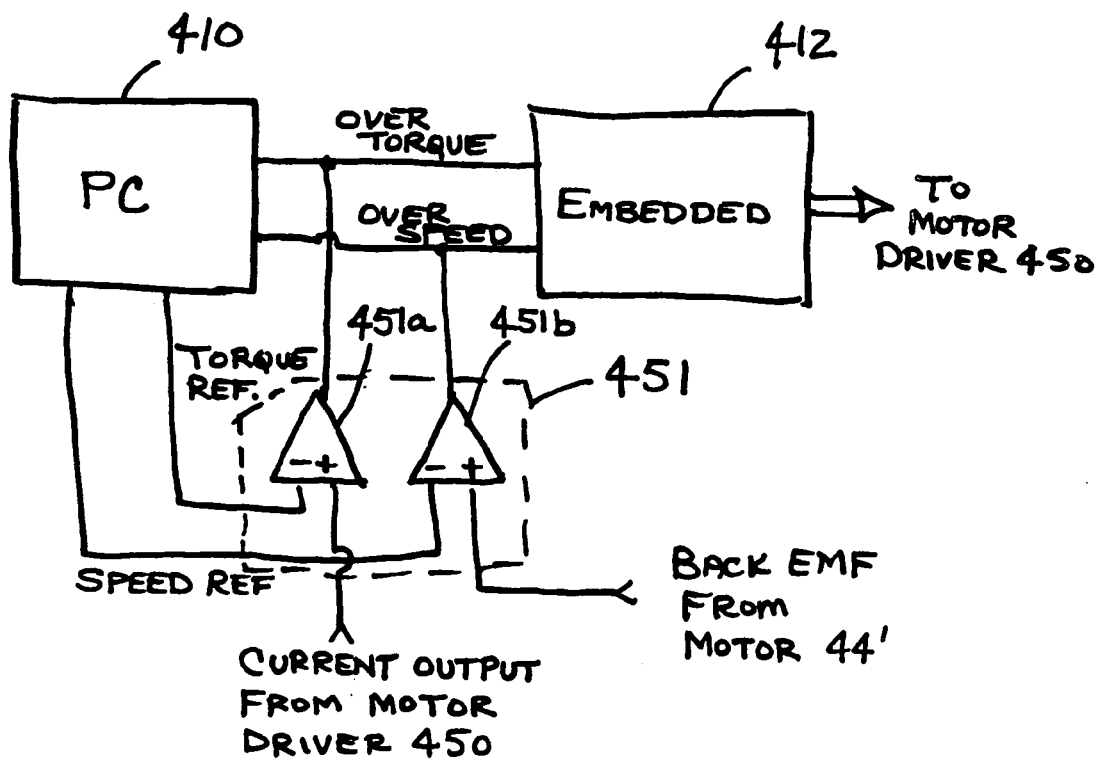
FIG. 13 is an electrical block diagram of the safety circuits associated with the peristaltic pump motor control portion of the control system of FIG. 11.

Similar safety circuits are provided for control of the peristaltic pump 44'. As indicated in FIG. 11, the peristaltic pump also includes an overspeed/overtorque network 451. In the preferred embodiment, the peristaltic pump 44' is not a brushless motor like the injection motor, and receives a pulse width modulated input signal from the PWM control circuitry 450. Pump motor 44' develops a back EMF that can be sensed and used as a feedback signal along with the output current from the motor driver circuit 450. An electrical block diagram representation of the peristaltic pump safety circuits is illustrated in more detail in FIG. 13. Referring thereto, the PC and embedded processors are indicated at 410 and 412 respectively. The safety circuit illustrated in FIG. 13 is virtually identical to that used for sensing the speed and current of the injector motor. A pair of comparators 451*a* and 451*b* of the overspeed/overtorque network 451 are used in manner similar to the comparators 462*a* and 462*b* previously described with respect to the safety circuits of the injector motor. The comparator 451*a* provides an overtorque output signal to both of the processors, and the comparator 451*b* provides an overspeed input signal to both of the processors. Comparator 451 receives a torque reference voltage signal from the PC processor 410 and the comparator 451*b* receives a speed reference voltage signal from the processor 410. The comparator 451*a* monitors a current output signal from motor driver network 450 and provides an output signal whenever the monitored current output signal exceeds the torque reference signal provided from processor 410. The comparator 451*b* monitors a back EMF signal from =motor 44' and provides an output signal whenever the back EMF signal exceeds the speed reference voltage signal applied by processor 410. The embedded processor 412 provides the primary drive control signal to the motor driver 450.

In the embodiment of the invention illustrated in FIG. 9, all operator/user interface with the system is performed through the control panel, except for turning on the power supply and activation of the emergency stop switch. Communication with the processor or processors of the system is performed through switches on the touch screen 432 overlying the display 433. The computer generates various screens on the display, with appropriate simulated switch indicators that align with touch pads on the touch screen, which enable the operator to communicate with the microprocessor(s) through the touch screen. When power is initialized to the system, the control panel display will communicate to the user that the system is performing self diagnostic tests. Following the diagnostic tests, the display will illustrate various set-up windows providing a series of instructions for the operator that will guide the operator through the step-by-step set-up procedure, generally including syringe loading, locking and filling, disposable connections, and flushing.

Sample screens that are generated by the PC processor and which are displayed to the user for the power-up, and self diagnostic functions are illustrated in FIGS. 14-17. Referring thereto, the initial Power-up screen is illustrated in FIG. 14. This screen remains visible while the system runs in an internal diagnostic check to make sure all functions are working properly. The system will then automatically begin set-up. The screen of FIG. 15 will appear as the syringe ram moves to a back position, after which the screen of FIG. 16 will be displayed which instructs the operator how to load the syringe assembly. Upon completion of the syringe loading sequence, the operator pushes the "Done" pad on the touch screen of FIG. 16. The system is now ready to begin the "set-up" procedure, and displays the screen of FIG. 17 while the syringe ram is moved forward.

The "set-up" instructions begin with the screen of FIG. 18. Referring thereto, the operator is instructed in a step-by-step manner as to how to load the tubing assembly portion of the system. When the operator has completed the steps identified in FIG. 18, he activates the touch screen by pushing the "Done" switch, and proceeds to the steps indicated on the screen of FIG. 19. The screen of FIG. 19 includes flushing operations of the pressure dome, manifold and fluid lines. When these steps have been completed and the "Done" switch has been activated, the set-up instruction screen of FIG. 20 will be displayed. Screen 20 provides instructions for attaching the pressure transducer and pump assemblies of the system. Upon completion of the FIG. 20 screen items and activation of the "Done" switch, the set-up instructions of the screen of FIG. 21 will be displayed. The steps of FIG. 21 complete the set-up instructions, and when the operator activates the "Done" switch of the FIG. 21 screen, the system is ready to fill the syringe. It will be noted that during all of the set-up steps included on the screens of FIGS. 18-21, the operator has the option of reverting to a prior screen by pushing the "Back" switch area on the screen.

Upon completion of the set-up instructions, before the system proceeds with filling of the syringe, the operator must activate the "OK" switch of the screen of FIG. 22. Upon activation of the "OK" switch, the system will proceed through an automated filling and purging operation. As the syringe piston is withdrawn to the rear of the syringe, drawing contrast material into the syringe, the screen of FIG. 23 will be displayed. Then, as the piston reverses direction and begins moving forward, air will be purged out of the upper port of the syringe, during which time the screen of FIG. 24 will be displayed. The syringe piston automatically stops before the lower valve within the patient manifold moves. Following the syringe purge operation, the screen of FIG. 25 will be displayed, providing instructions to the operator as to how to proceed with the purging of the line from the syringes lower port to the system's high pressure line. In order to purge the line, the operator must press and hold the "Purge" switch of the FIG. 25 screen and visually observe the purging process as air and bubbles are pushed out of the line between the syringe and the patient manifold, and from the front/nose of the patient manifold and out into the high pressure line. When this procedure has been completed, the operator releases the "Purge" switch and activates the "Done" switch of the FIG. 25 screen. When the operator is engaging the "Purge" switch, the screen of FIG. 26 will be displayed. When the operator releases contact with the "Purge" switch, the screen of FIG. 25 will reappear. After the "Done" switch of FIG. 25 has been activated, the display screen of FIG. 27 will be displayed.

Figure 29:
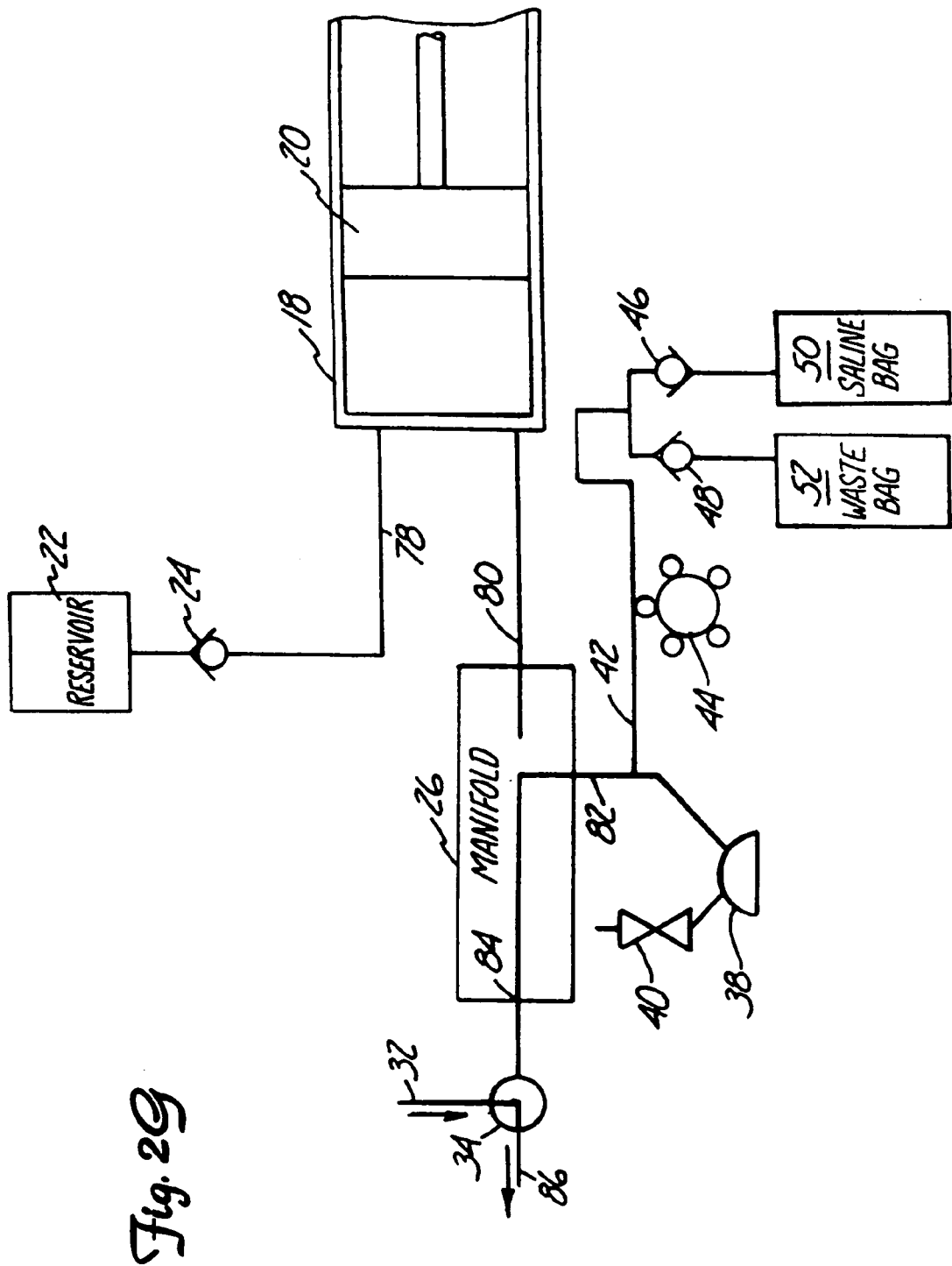
FIG. 29 is an illustration of a Final Start-Up screen of the display of the system of FIG. 11.

The FIG. 27 process steps relate to the final saline flush procedure. When the operator engages the "Flush" switch of the FIG. 27 screen, the system will flush the line from the saline bag to the stopcock, assuring that no air bubbles are present in the line. As long as the operator continues to engage the "Flush" switch of the FIG. 27 screen, the screen of FIG. 28 will be displayed. Upon completion of the final saline flush procedure, the operator will release the "Flush" switch and engage the "Done" switch of the screen of FIG. 27, which will cause the display screen of FIG. 29 to be displayed. The FIG. 29 screen is the final start-up screen. Following completion of the instructions of the FIG. 29 screen, the operator activates the "Done" switch of the display, completing the start-up procedure, and the system is now ready for connection to a catheter.

Upon successful completion of the start-up procedure described above, the system displays the MAIN screen, generally indicated in FIG. 30. The MAIN display screen of the control panel of a preferred configuration thereof is divided into sections as illustrated in FIG. 30. It will be appreciated that all of the formatting for the display screen is provided by and under control of the PC microprocessor 410. Referring to FIG. 30, there are four "function keys" vertically aligned along the right side of the screen and designated as "Inject" (500); "Saline" (501); "Aspirate" (502); and "Purge" (503). The icons for these four function soft keys are aligned with appropriate switch pads of the touch screen 432 so that an operator can press selected ones of the function keys and bring up the status window for the chosen function. The Status window is indicated at 505, and an Indicator window is located at 506. The Status window is used to display system messages and to provide feedback to the user on the state of system operations. The Status indicator window 506 displays key system sensors when they are active.

Three "Injection Type" or "Select Injection" keys indicated as LCA (left coronary artery) 508; RCA (right coronary artery) 509; and LV/Ao (left ventricle/aorta) 510 are positioned above the function keys and provide operator input as to the type of injection procedure that will be performed. The injection type can be changed by simply pressing one of these three type buttons. When a new type is selected, the default parameter values for the selected type are calculated and displayed in the parameter keys. In the preferred embodiment (as hereinafter described in more detail) the injection parameters are calculated based on actual values such as weight of the patient to be treated. A verbal indication of the selected injection key is indicated at the very top of the display screen. In the sample screen indicated in FIG. 30, the LCA key has been selected and its associated indication "LEFT CORONARY" is displayed at the top of the screen.

The following parameters can be changed by pressing the icon of the desired parameter while the Injection Status window is open, or during the set-up procedure: Flow Rate; Injection Volume; Injection Pressure; and "Rise Time". The injection parameter/limit keys are located along the top of the display screen.

A "Flow Rate" window 512 displays the greatest flow rate obtainable if the hand remote controller is completely depressed. The units for flow rate are ml/sec. An "Injection Volume" panel 513 displays the total volume limit that can be injected during a single injection. The units for this parameter are ml. An "Injection Pressure" window 512 displays the maximum pressure within the syringe allowed during an injection. If this pressure is reached, a warning light will come on and the injection flow rate will be limited to the indicated pressure. The units for pressure are psi. A "Rise Time" window 515 displays the maximum rise time allowed during an injection. The units for rise time are seconds.

The system has the unique ability to either automatically or manually refill the syringe, as described in copending patent application Ser. No. 08/946,243, entitled Angiographic Injector System with Automatic High/Low Pressure Switching filed on Oct. 7, 1997. The "Refill" key is located in the lowermost portion of the display screen comprises the "Options" portion of the display screen. The Refill key, generally indicated at 517 can be reset at any time during a case or procedure by simply pressing the desired icon.

A second Option key generally indicated as the "Rate Type" key is located at 518 which permits selection of the injection procedure as either a "Fixed" rate or a "Variable" rate which can be controlled in real time by the remote hand controller 14'.

Figure 31:
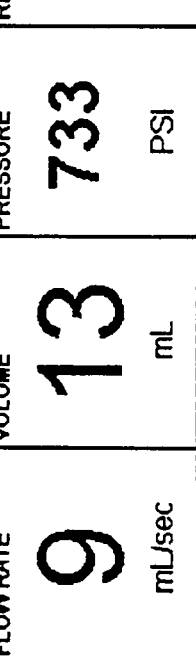
FIG. 31 is an illustration of tahe MAIN display screen of FIG. 30 illustrating operation in an injecting mode.

The processor provides real-time information to the user on the instantaneous conditions existing during an injection procedure. These conditions are displayed in the Status window 505 as indicated on the sample screen of FIG. 31. The display panel also displays the results of the last injection in a "Last Injection" window 520. The last injection results include the "total volume" and the "maximum flow rate" of the last injection performed. The display panel also indicates the cumulative total of contrast material that has been injected in a patient for the current case, indicated in the "Contrast Total" display window 522. The Last Injection and Contrast Total display windows are located near the lower left portion of the display screen. The Contrast Total display provides important information to have instantaneously available during the injection procedure, since a case procedure may involve numerous filling procedures of the syringe. Further, such filling procedures may represent either total or only partial filling of the syringe. Prior techniques depended upon the operator/user for maintaining a log of the total amount of contrast material that had been administered to a patient over the course of successive injections. Failure to maintain an accurate cumulative total for the amount of contrast material injected can result in overdose of injected material to the patient.

In the preferred embodiment, a display window/key indicated as a "Patient's Weight" is indicated at 524. In the preferred embodiment, this display window displays the weight of the current patient. Selection of this key will allow the user to enter a patient's weight in kilograms into the system. The patient weight is used to calculate injection values and limits (hereinafter described in more detail).

The final key on the display panel is the "End Case" key 526 located near the lower right portion of the display panel. Activation of this key will prompt the user through the proper steps before shut-down of the system or before starting a new case.

The Emergency button or switch 434 (FIG. 11) is physically located on the upper right hand portion of the control panel. This is the only functional switch (besides the Power Supply switches) which is not located on the display screen. The Emergency switch disables any on-going function and displays a message in the status window that the emergency button is engaged. The emergency button or switch is an alternate action type of switch. When engaged, the button is lit. To disengage the switch the user must press the button again.

Figures 32, 33:
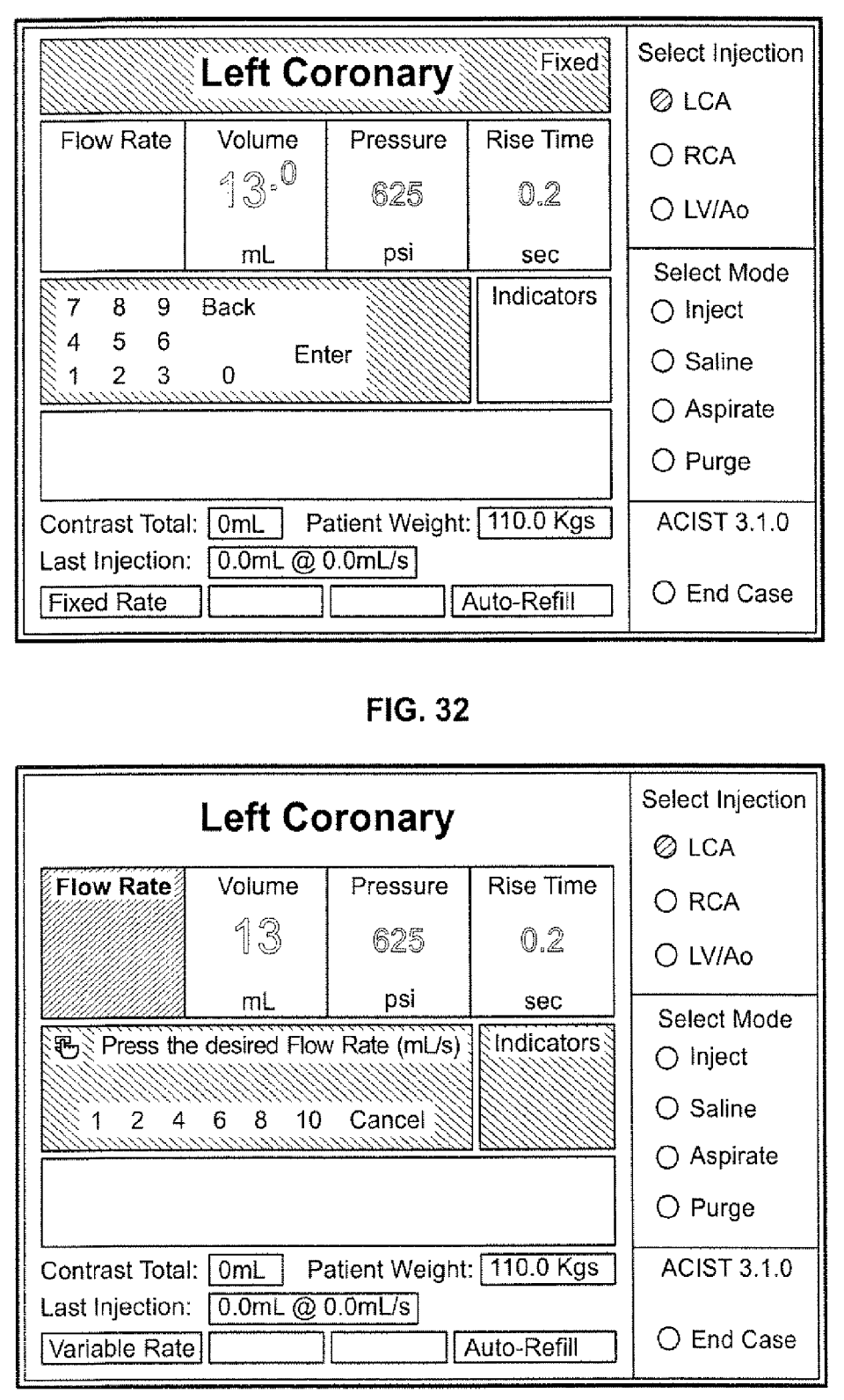

The injection limits can be changed by pressing the key (512-515) of the desired parameter. If the injection (key 518) is set to a "Fixed" mode, a keypad will be presented to the user in the status window. This condition is illustrated in FIG. 32. A new value can now be entered. This new value will be checked by the processor to see if it within an acceptable range for the type of ejections elected. If the entered value is out of the acceptable range, a message will be displayed indicating this fact to the user. If the "Cancel" key is pressed, the previously set value will remain set. If the injection option (key 518) is set to the "variable" mode, a choice of six different values are displayed in the status window for the user to select. A sample display window corresponding to this situation is illustrated in FIG. 33. If the "Cancel" key is pressed, the previously set value will remain set.

An Injection is initiated by pressing the "Inject" button or key 500. If the LV/Ao (large injection button), is selected, the user will be asked to confirm this. The LV/Ao injection procedure represents the largest volume use of contrast material; whereas the RCA injection procedure uses the least amount of contrast material. The user is then asked by prompt on the display if it is okay to "Arm" the injection. The user must press the "OK" key in the status window. At this point, if there is not enough contrast in the syringe to perform the requested injection, the system will prompt for a refill. The refill will be automatic or manual, depending on the status of the "Refill" option key 517. When the volume level is correct, the user will be prompted to activate the hand controller 14' for initiating the injection procedure.

If the volume injected is less than 10% of the volume limit, the number of injections will not increase and the hand controller will remain armed. A "large" injection requires the user to press "Large OK" again before another injection is permitted. The user exit the inject function by pressing any key on the screen.

The Saline Flush function, initiated by activation of the "Saline" key 501, pulls saline from the saline bag and flushes the disposable and line connections. When this function is initiated, the "Saline Flush" status window will be displayed with a "Flush" key and a "Done" key. Pressing the "Flush" key will flush the disposable with saline for up to 10 seconds or until the user stops pressing the key. Pressing the "Done" button in the window will end the flush process and return the user to the "MAIN" screen.

The Aspirate function draws line fluid back into the waste bag from the catheter through the disposable. It may be used to remove bubbles if they are detected in the line. The aspirate function is initiated by selecting the "Aspirate" button or key 502 on the display panel. The "Aspirate" status window will be displayed on the screen. Pressing the "Aspirate" key will pull line fluid back through the disposable into the waste bag as long as the "Aspirate" key is depressed, for up to 10 seconds. Pressing the "Done" button will return the user to the "MAIN" screen.

The manual purge function is used to flush air from the disposable. There are two choices when purging, comprising the Syringe Purge and the Line Purge. Syringe Purge involves purging air out of the syringe and will be stopped when air has been purged from the syringe and the fluid pushes the syringe check valve closed. Line Purge purges air from the syringe to the stopcock through the patient manifold. This method will send contrast material through the disposable and will disengage the bubble detection device. This purge is done at system start-up in order to clear air out of the interconnect of the syringe to the patient manifold and the front on the patient manifold valve. During a procedure, Line Purge may also be used when an air bubble remains within the disposal after the aspirator flush procedures have been tried. To access the "Purge" function, the "Purge" key 503 is selected from the "MAIN" screen. The "Purge" status window will be displayed. Three options are presented on the screen: "Syringe", "Cancel", and "Line". Selecting "Cancel" will return to the "MAIN" screen. If "Line" is selected, the user is warned to disconnect the patient. The user must acknowledge this by pressing the "okay" key. At this point, or if "Syringe" has been selected, a "Purge" key and "Done" key are displayed in the window. The "Purge" key is a press and hold key which will initiate and continue the purging through the line or syringe until the user releases the key, for up to 10 seconds. The purge will stop automatically if the air is completely purged out and the contrast valve is successfully closed. If the user stops the purge before the valve closes, a message will indicate that the purge is not complete. Pressing the "Done" key or any other key on the screen will exit the purge function. A sample screen for a manual purge function is illustrated in FIG. 34.

If the automatic refill option is chosen by means of the key 517, the syringe will automatically refill to 110 ml. if there is not enough contrast media within the syringe for the desired injection volume limits. This will occur automatically at the time of injection. If manual refill is chosen, the "Refill" status window will be displayed. A "Purge" key, a "Done" key, and a "Refill" key are active in this window. Pressing and holding down the "Refill" key will draw the plunger back, filling the syringe. The current amount of contrast media in the syringe is displayed as it fills. When the "Refill" button is released, the refilling operation discontinues. Pressing the "Purge" key will purge air and fluid out of the syringe as long as the "Purge" key is depressed. Pressing the "Done" button will send the user back to the "MAIN" screen. If there is still not enough contrast in the syringe to satisfy the injection value of limits, the "Refill" status window will re-open at the time of injection. A sample screen for the manual refill operation is illustrated in FIG. 35.

To end a case, the "End Case" button 526 is activated. A "Cancel" key and an "End" key are displayed in the status box. If the "Cancel" key is selected, the user is returned to the "MAIN" screen. If the "End" key is selected, the end case sequence begins. When the high pressure line is disconnected and the contrast container is removed from the receptacle, the "No Contrast" indicator will appear. If the "Done" button is then depressed or selected, the plunger is automatically withdrawn from the syringe body and the syringe can be removed from the system by unlocking and opening the chamber.

Prior systems have not provided automated determination of default injection parameters that are directly related to values or characteristics of the patient to be treated. Such characteristics might include such things as weight, age, wellness of the person, vascular robustness, catheter size and the like. For example, prior systems have included memory recall features for stored injection parameter values that may have been stored by a physician for a particular patient or for a particular procedure wherein the stored parameters represent the typical injection parameter choices of that physician. The present invention provides an automated method for determining suggested default injection parameter values just prior to an injection procedure, which injection parameter values are directly related to values or conditions of the patient to be treated. In a preferred embodiment implementation of this method, the injection parameter default values are calculated using the "weight" of the patient. As stated above, however, other unique patient factors could be used in creating the default value calculations. For a preferred embodiment determination of the default injection parameters based on the patient's weight, three different sets of formulas or algorithms have been used, corresponding to the three different types of injections that can be performed by the system (i.e., LCA, RCA or LV/Ao). For the LCA (Left Coronary procedure), the equations used for determining the four injection parameter default values are:

$$LCA \text{ Flow Rate Limit} = 3.5 Ln(\text{weight}) - 7.6 \qquad \text{Equation 1}$$

$$LCA \text{ Volume Limit} = 5.17 Ln(\text{weight}) - 11 \qquad \text{Equation 2}$$

$$LCA \text{ Rise Time} = (\text{flow rate} + 10)/100 \qquad \text{Equation 3}$$

$$LCA \text{ Pressure Limit} = (\text{flow rate} + 20)25 \qquad \text{Equation 4}$$

Table 1 provides a listing of calculated default injection parameter values determined by Equations 1-4 for selected patient weights.

TABLE 1

Left Coronary Default Parameters

| Weight (kg) | Flow Rate (max) (ml/sec) | Volume (max) (ml) | Rise Time (max) (sec) | Pressure Limit (p.s.l.) |
|---|---|---|---|---|
| 10 | 0 | 1 | 0.1 | 511 |
| 20 | 3 | 4 | 0.1 | 572 |
| 30 | 4 | 7 | 0.1 | 608 |
| 40 | 5 | 8 | 0.2 | 633 |
| 50 | 6 | 9 | 0.2 | 652 |
| 60 | 7 | 10 | 0.2 | 668 |
| 70 | 7 | 11 | 0.2 | 682 |
| 80 | 8 | 12 | 0.2 | 693 |
| 90 | 8 | 12 | 0.2 | 704 |
| 100 | 9 | 13 | 0.2 | 713 |
| 110 | 9 | 13 | 0.2 | 721 |
| 120 | 9 | 14 | 0.2 | 729 |
| 130 | 9 | 14 | 0.2 | 736 |

The default injection parameters for a RCA (Right Coronary procedure) are, in the preferred embodiment, determined by Equations 5-8:

$$RCA \text{ Flow Rate Limit} = 2.1 Ln(\text{weight}) - 4.8 \qquad \text{Equation 5}$$

$$RCA \text{ Volume Limit} = 2.7 Ln(\text{weight}) - 6 \qquad \text{Equation 6}$$

$$RCA \text{ Rise Time} = (\text{flow rate} + 10)/100 \qquad \text{Equation 7}$$

$$RCA \text{ Pressure Limit} = (\text{flow rate} + 15)25 \qquad \text{Equation 8}$$

Table 2 provides a listing of values of the four injection parameter default values determined by Equations 5-8 for selected patient weights.

TABLE 2

Right Coronary Default Parameters

| Weight (kg) | Flow Rate (max) (ml/sec) | Volume (max) (ml) | Rise Time (max) (sec) | Pressure Limit (p.s.l.) |
|---|---|---|---|---|
| 10 | 0 | 0 | 0.1 | 376 |
| 20 | 1 | 2 | 0.1 | 412 |
| 30 | 2 | 3 | 0.1 | 434 |
| 40 | 3 | 4 | 0.1 | 449 |
| 50 | 3 | 5 | 0.1 | 460 |
| 60 | 4 | 5 | 0.1 | 470 |
| 70 | 4 | 5 | 0.1 | 478 |
| 80 | 4 | 6 | 0.1 | 485 |

TABLE 2-continued

Right Coronary Default Parameters

| Weight (kg) | Flow Rate (max) (ml/sec) | Volume (max) (ml) | Rise Time (max) (sec) | Pressure Limit (p.s.l.) |
|---|---|---|---|---|
| 90 | 5 | 6 | 0.1 | 491 |
| 100 | 5 | 6 | 0.1 | 497 |
| 110 | 5 | 7 | 0.2 | 502 |
| 120 | 5 | 7 | 0.2 | 506 |
| 130 | 5 | 7 | 0.2 | 511 |

Default injection parameter values for the LV/Ao injection selection (Left Ventricle/Aorta procedure), for the preferred embodiment, are calculated according to Equations 9-12.

$$LV/Ao \text{ Flow Rate Limit} = 7Ln(\text{weight}) - 16 \quad \text{Equation 9}$$

$$LV/Ao \text{ Volume Limit} = 22Ln(\text{weight}) - 46 \quad \text{Equation 10}$$

$$LV/Ao \text{ Rise Time} = (\text{flow rate} + 10)/100 \quad \text{Equation 11}$$

$$LV/Ao \text{ Pressure Limit} = 60 \text{ (flow rate)} + 200 \quad \text{Equation 12}$$

Table 3 illustrates default injection parameter values determined by Equations 9-12 for selected patient weights.

TABLE 3

Left Ventricle/Aorta Default Parameters

| Weight (kg) | Flow Rate (max) (ml/sec) | Volume (max) (ml) | Rise Time (max) (sec) | Pressure Limit (p.s.l.) |
|---|---|---|---|---|
| 10 | 0 | 5 | 0.1 | 207 |
| 20 | 5 | 20 | 0.1 | 498 |
| 30 | 8 | 29 | 0.2 | 669 |
| 40 | 10 | 35 | 0.2 | 789 |
| 50 | 11 | 40 | 0.2 | 883 |
| 60 | 13 | 44 | 0.2 | 960 |
| 70 | 14 | 47 | 0.2 | 1024 |
| 80 | 15 | 50 | 0.2 | 1080 |
| 90 | 15 | 53 | 0.3 | 1130 |
| 100 | 16 | 55 | 0.3 | 1174 |
| 110 | 17 | 57 | 0.3 | 1214 |
| 120 | 18 | 59 | 0.3 | 1251 |
| 130 | 18 | 61 | 0.3 | 1284 |

Figure 36A:
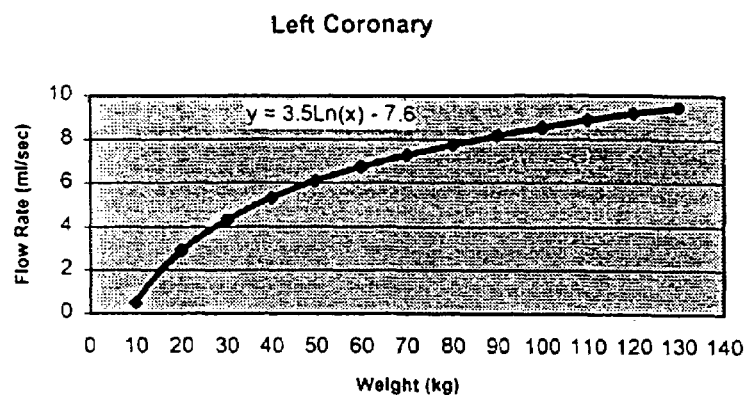
FIGS. 36A-C illustrate comparative graphs for default injection parameter values for Flow Rate Limits determined by algorithms of this invention relating to patient weight.
Figure 36B:
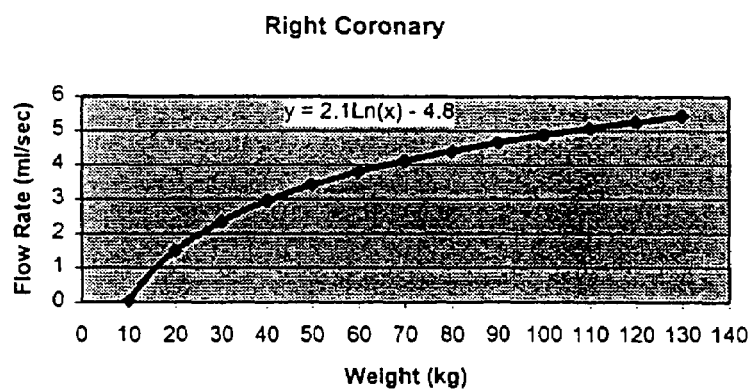
Figure 36C:
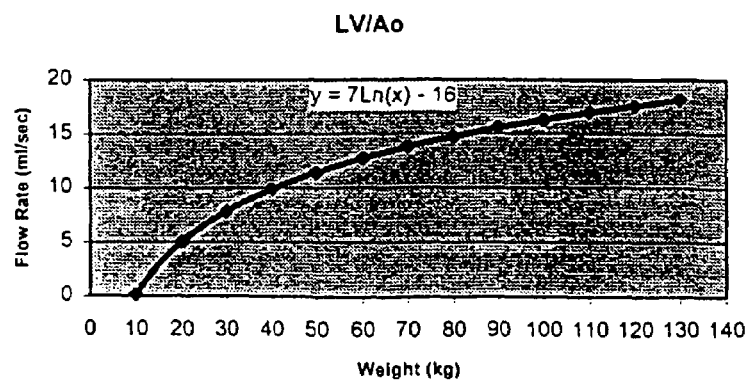

FIG. 36 illustrates comparative graphs for the default injection parameter values for Flow Rate Limits determined according to Equations 1, 5 and 9 respectively for the Left Coronary, the Right Coronary and the Left Ventricle/Aorta functions for patient weights from 10-130 kg.

Figure 37A:
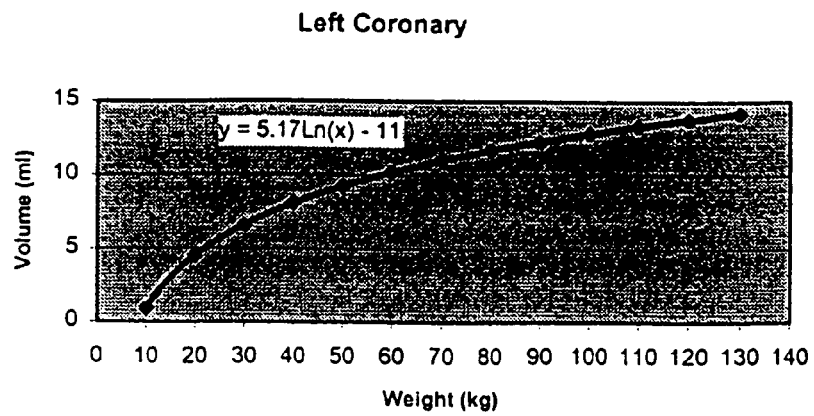
FIGS. 37A-C illustrate comparative graphs for default injection parameter values for Volume Limits determined by algorithms of this invention relating to patient weight.
Figure 37B:
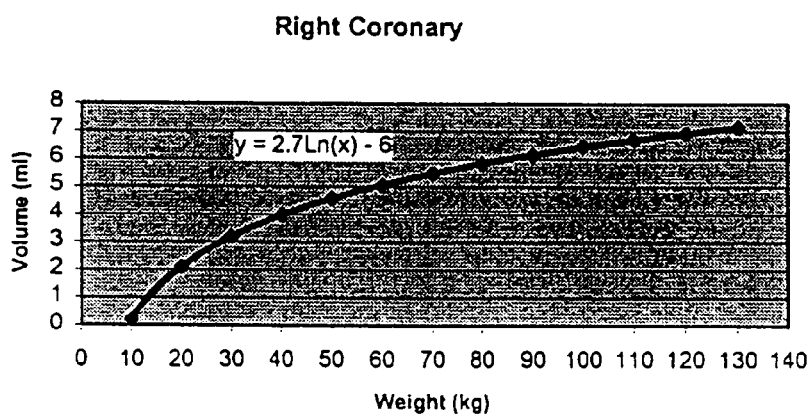
Figure 37C:
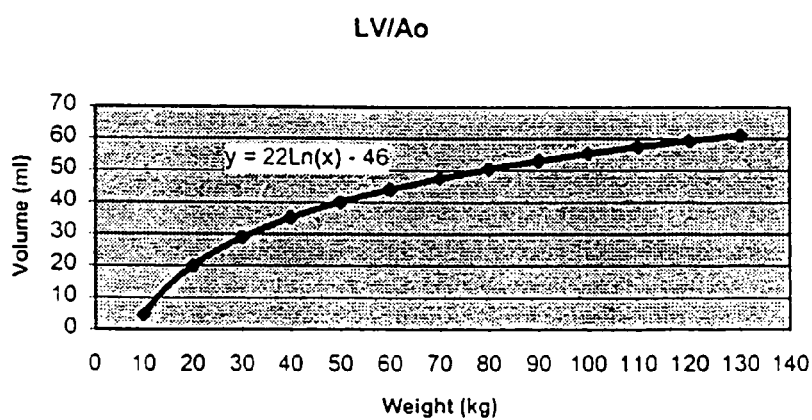

FIG. 37 illustrates comparative graphs of the Volume Limit default injection parameter calculated according to Equations 2, 6 and 10 for the Left Coronary, the Right Coronary and the Left Ventricle/Aorta selections respectively for patient weights ranging from 10-130 kg.

It will be appreciated that the automated determination of default injection parameter values based on the patient's unique characteristics (such as weight), minimizes guess factors associated with selection of proper default parameters for a particular patient, provides a method of determining the default parameters which accommodates changes in the patient's condition between injection procedures and eliminates the requirement for supplemental charts and graphs upon which the physician or operator administering the injection procedure might have to otherwise rely in order to select or determine proper injection parameter default values.

Figure 38:
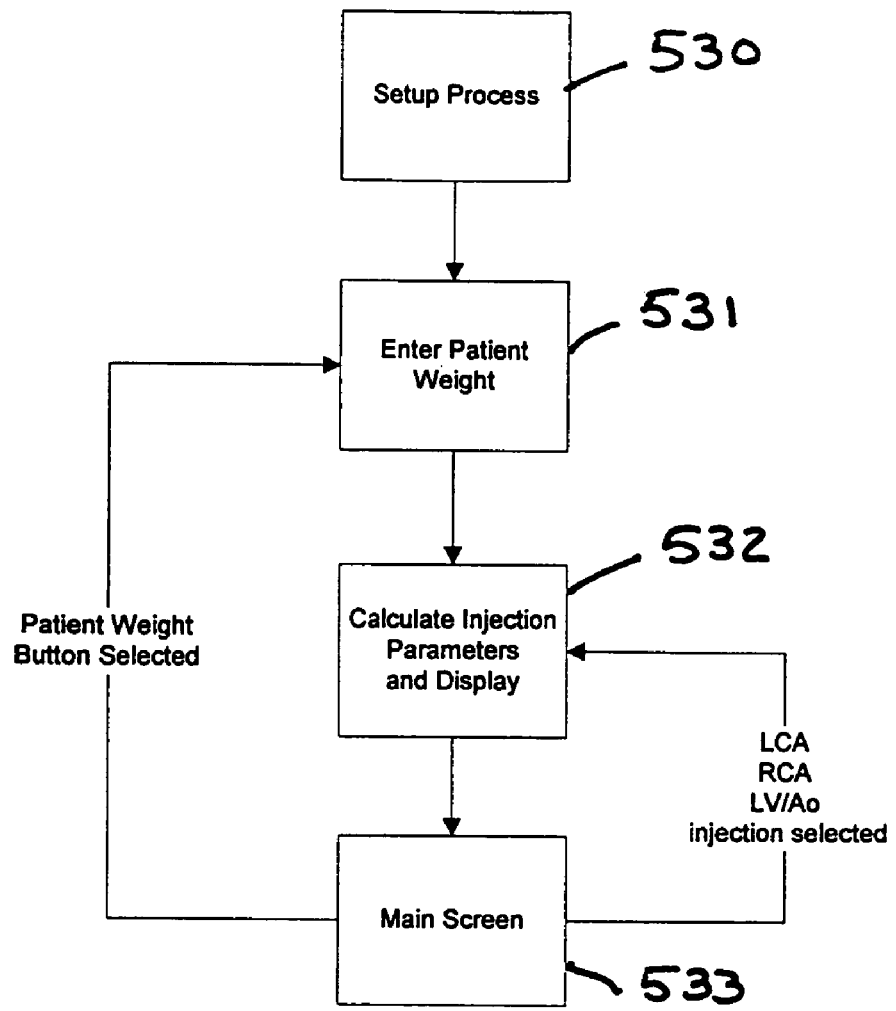
FIG. 38 is a diagrammatic flow chart illustrating the process used to determine the patient related default injection parameters of FIGS. 36 and 37.

Accordingly, in order to determine a set of default injection parameter values for a particular injection procedure, the user need simply select one of the three injection selectors provided by selection buttons 508-510 and to enter the patient's weight in kilograms in the patient weight window 524. A flow chart of this process is illustrated in FIG. 38. Referring thereto, after the initial set-up process which includes an initial selection of the type of injection to be performed (block 530) the operator enters the patient's weight (block 531). The microprocessor automatically determines the default injection parameters by using the appropriate algorithms therefor (block 532) according to the selected injection procedure (i.e., LCA, RCA or LV/Ao) and according to the patient weight entered into the system through the display panel. The calculated default injection parameter values are then displayed on the MAIN screen (block 533) to complete the process. The operator has the option of changing the determined values, but for most applications no changes to the default values will be required.

It will be appreciated that while preferred embodiment descriptions and applications of the invention have been disclosed, other modifications of the invention not specifically disclosed or referred to herein will be apparent to those skilled in the art in light of the foregoing description. This description is intended to provide specific examples of preferred embodiments, structures, methods, algorithms and applications clearly disclosing the present invention and its operative principles. Accordingly, the invention is not limited to any particular embodiment or configuration or component parts thereof. All alternatives, modifications and variations of the present invention which fall within the spirit and broad scope of the appended claims are covered.

We claim:

1. A medical fluid injection system, comprising:
  a device for injecting a medical fluid into a patient;
  a drive means operatively connected with the device for causing the device to inject the medical fluid;
  a first computer configured to receive at least a first fluid injection setting; and
  a second computer configured to receive a command to perform an injection from the first computer and operatively connected with the drive means so as to control an injection,
  wherein the first and second computers each have an independent communication link to at least one sensor for monitoring at least one safety parameter throughout the injection process, such that either or both of the first and second computers control the device according to the monitoring of the at least one safety parameter.

2. The injection system of claim 1, wherein the first computer is configured to receive the first fluid injection setting via a user interface.

3. The injection system of claim 1, wherein the device further includes at least one compare circuit separate from the first and second computers which is set with a predetermined level of the at least one safety parameter with a command from the first computer; and wherein the compare circuit is configured to monitor the at least one safety parameter and to provide a signal to either or both of the first and second computers when the at least one safety parameter is outside the predetermined level.

4. The injection system of claim 1, wherein at least one of the first and second computers is a PC-type computer.

5. The injection system of claim 1, wherein at least one of the first and second computers is an embedded processor.

6. The injection system of any of claims 1, 2 or 3, wherein the first fluid injection setting is a desired injection flow rate.

7. The injection system of either of claims 1, 2 or 3, wherein the at least one safety parameter is an injection flow rate.

8. The injection system of either of claims 1, 2 or 3, wherein the at least one safety parameter is a fluid pressure.

9. The injection system of claim 1, wherein either or both of the first and second computers are configured to control a servo amplifier according to the monitoring of the at least one safety parameter.

10. The injection system of either of claims 1, 2 or 3, wherein at least one of the first and second computers is configured to receive a second fluid injection setting from a remote control.

11. A method of controlling a medical fluid injection apparatus, comprising:
   providing an injection apparatus with a fluid delivery mechanism for injecting a medical fluid;
   providing at least a first fluid injection setting to at least a first computer of the fluid delivery system;
   controlling a medical fluid injection from the fluid delivery mechanism with at least a second computer operatively connected with the fluid delivery mechanism and configured to receive from the first computer a command to perform an injection;
   monitoring throughout the injection process at least one safety parameter of the medical fluid injection with both the first and second computers; and
   controlling the medical fluid injection with either or both of the first and second computers according to the monitoring of at least one safety parameter.

12. The method of claim 11, wherein the first computer is configured to receive the first fluid injection setting via a user interface.

13. The method of claim 11, including the steps of:
   providing at least one compare circuit separate from the first and second computers;
   setting in the compare circuit a predetermined level of the safety parameter with a command from the first computer;
   using the compare circuit to monitor the safety parameter and to provide a signal to either or both of the first and second computers when the safety parameter is outside the predetermined level.

14. The method of claim 11, wherein at least one of the first and second computers is a PC-type computer.

15. The method of claim 11, wherein at least one of the first and second computers is an embedded processor.

16. The method of either of claims 11, 12 or 13, wherein the first fluid injection setting is a desired injection flow rate.

17. The method of claim 13, wherein the at least one safety parameter is an injection flow rate.

18. The method of claim 13, wherein the at least one safety parameter is a fluid pressure.

19. The method of either of claims 11, 12 or 13, wherein at least one of the first and second computers is configured to receive a second fluid injection setting from a remote control.

20. The method of claim 11, wherein either or both of the first and second computers are configured to control a servo amplifier according to the monitoring of the at least one safety parameter.

* * * * *